(12) United States Patent
Parikh et al.

(10) Patent No.: US 7,132,122 B2
(45) Date of Patent: *Nov. 7, 2006

(54) DIRECT MICRO-PATTERNING OF LIPID BILAYERS USING UV LIGHT AND SELECTED USES THEREOF

(75) Inventors: Atul Navinchandra Parikh, Davis, CA (US); Chanel Kitmon Yee, Davis, CA (US); Meri Lynn Amweg, Winston-Salem, NC (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/698,995

(22) Filed: Oct. 30, 2003

(65) Prior Publication Data

US 2004/0180147 A1 Sep. 16, 2004

Related U.S. Application Data

(60) Provisional application No. 60/422,902, filed on Oct. 30, 2002, provisional application No. 60/423,327, filed on Oct. 31, 2002, provisional application No. 60/469,928, filed on May 12, 2003, provisional application No. 60/496,256, filed on Aug. 18, 2003.

(51) Int. Cl.
*B05D 3/06* (2006.01)
*C12Q 1/70* (2006.01)
*C03C 25/26* (2006.01)

(52) U.S. Cl. .................. 427/2.13; 427/2.14; 427/2.31; 427/553; 427/555; 427/558; 216/65; 216/66; 435/5

(58) Field of Classification Search ............ 427/2.1, 427/2.13, 2.14, 2.31, 508, 510, 512, 553, 427/555, 558; 216/65, 66; 435/5
See application file for complete search history.

(56) References Cited

U.S. PATENT DOCUMENTS

| | | | |
|---|---|---|---|
| 5,217,455 A * | 6/1993 | Tan ........................... | 606/9 |
| 5,310,648 A * | 5/1994 | Arnold et al. ............... | 435/5 |
| 5,521,702 A * | 5/1996 | Salamon et al. ............ | 356/244 |
| 6,080,423 A * | 6/2000 | Charych et al. ............ | 424/450 |
| 6,228,326 B1 | 5/2001 | Boxer et al. | |
| 6,846,654 B1 * | 1/2005 | Blackburn et al. .......... | 435/7.1 |
| 2002/0094544 A1 | 7/2002 | Fang et al. | |
| 2005/0244487 A1 * | 11/2005 | Sansinena et al. .......... | 424/450 |

OTHER PUBLICATIONS

S.P. Pappas, ed., UV Curing: Science and Technology, Technology marketing corp., Stamford, Conn., USA, 1978 (no month), excerpts p. 96-96, 102-111 & 124-125.*
Anderson et al. (2000) "Concentration of MHC Class II Molecules in Lipid Rafts Facilitates Antigen Presentation." *Nature Innunology* 1 (2): 156-162, Aug.
Anderson et al. (2002) "A Role for Lipid Shells in Targeting Proteins to Caveolae, Rafts, and Other Lipid Domains." *Science* 296: 1821-1825, Jun.

(Continued)

*Primary Examiner*—Marianne Padgett
(74) *Attorney, Agent, or Firm*—Paul Littlepage; Quine Intellectual Property Law Group, LLC

(57) ABSTRACT

This invention provides novel methods for creation of patterned lipid bilayer membranes as well as methods for refunctionalization of such patterned membranes with selected components. Such components optionally comprise, e.g., lipid bilayer membranes (which optionally comprise specific proteins), proteins, non-biologic moieties, etc.

42 Claims, 31 Drawing Sheets
(24 of 31 Drawing Sheet(s) Filed in Color)

OTHER PUBLICATIONS

Axelrod et al. (1976) "Mobility Measurement by Analysis of Fluorescence Photobleaching Recovery Kinetics." *Biophysical Journal* 16:1055-1069, vol. 16, no month 1976.

Bayerl and Bloom (1990) "Physical properties of single phospholipid bilayers adsorbed to micro glass beads." *Biophysical Journal* 58:357-362, Aug.

Bayley and Cremer (2001) "Stochastic sensors inspired by biology." *Nature* 413:226-230, Sep.

Boxer (2000) "Molecular transport and organization in supported lipid membranes." *Current Opinion in Chemical Biology* 4:704-709, no month.

Cremer et al. (1999) "Creating Spatially Addressed Arrays of Planar Supported Fluid Phospholipid Membranes." *Journal of American Chemistry Society* 121:8130-8131, Aug.

Cremer et al. (1999) "Formation and Spreading of Lipid Bilayers on Planar Glass Supports." *Journal of Physical Chemistry B* vol. 103, No. (13):2554-2559, no month.

Dietrich et al. (2001) "Lipid Rafts Reconstituted in Model Membranes." *Biophysical Journal* 80:1417-1428, Mar.

Eiserich et al. (1998) "Formation of nitric oxide-derived inflammatory oxidants by myeloperoxidase in neutrophils." *Nature* 391:393-397, Jan. 22, 1998.

Eiserich et al. (2002) "Myeloperoxidase, a Leukocyte-Derived Vascular NO Oxidase." *Science* 296:2391-2394, Jun. 28, 2002.

Fang et al. (2002) "Membrane Protein Microarrays." *Journal of American Chemistry Society* 124(11): 2394-2395, no month.

Fishman et al. (1993) "Gangliosides as Receptors for Bacterial Enterotoxins." *Advances Lipid Research* 25:165-187, vol. 25, no month.

Fodor et al. (1991) "Light-Directed, Spatially Addressable Parallel Chemical Synthesis." *Science* 251:767-773, Feb. 16, 1991.

Frisbie et al. (1994) "Functional Group Imaging by Chemical Force Microscopy." *Science* 265:2071-2074, Sep.

Grakoui et al. (1999) "The Immunological Synapse: A Molecular Machine Controlling T Cell Activation." *Science* 285: 221-227, Jul. 9,1999.

Groves et al. (1995) "Electric Field-Induced Concentration Gradients in Planar Supported Bilayers." *Biophysical Journal* 69:1972-1975, Nov.

Groves et al. (1997) "Micropatterning Fluid Lipid Bilayers on Solid Supports." *Science* 275:651-653, Jan. 31, 1997.

Groves et al. (1998) "Substrate-Membrane Interactions: Mechanism for Imposing Patterns on a Fluid Bilayers Membrane." *Langmuir* 14(12): 3347-3350, May.

Groves et al. (2001) "Control of Cell Adhesion and Growth with Micropatterned Support Lipid Membranes." *Langmuir* 17 (17):5129-5133, Jul.

Groves and Boxer. (2002) "Micropattern Formation in Supported Lipid Membranes." *Accounts of Chemical Research* 35:149-157, vol. 35, No. 3 Mar.

Hovis and Boxer (2001) "Patterning and Composition Arrays of Supported Lipid Bilayers by Microcontact Printing." *Langmuir* 17(11):3400-3405, Apr.

Hovis and Boxer (2000) "Patterning Barriers to Lateral Diffusion in Supported Lipid Bilayer Membranes by Blotting and Stamping." *Langmuir* 16(3):894-897, Jan. 4, 2000.

Kalb et al. (1992) "Formation of supported planar bilayers by fusion of vesicles to supported phospholipid monolayers." *Biochimica et Biophysica Acta* 1103:307-316, no month.

Kung et al. (2000) "Printing via Photolithography on Micropartitioned Fluid Lipid Membranes." *Advanced Materials* 12(10): 731-734, no month.

Kung et al. (2000) "Patterning Hybrid Surfaces of Proteins and Supported Lipid Bilayers." *Langmuir* vol. 16 No. (17): pp. 6773-6776, Jul. 29, 2000.

Lum et al. (2002) "Dynamic Regulation of LFA-1 Activation and Neutrophil Arrest on Intercellular Adhesion Molecule 1 (ICAM-1) in Shear Flow." *The Journal of Biological Chemistry* 277:20660-20670, Apr. 2, 2002 and Jun. 7, 2002.

Mayer et al. (1986) "Vesicles of variable sizes produced by a rapid extrusion procedure." *Biochimica et Biophysica Acta* 858:161-168, no month (after Feb. 10).

McConnell et al. (1986) "Supported planar membranes in studies of cell-cell recognition on the immune system." *Biochimica et Biophysica Acta* 864:95-106, no month.

Morigaki et al. (2001) "Patterning Solid-Supported Lipid Bilayer Membranes by Lithographic Polymerization of a Diacetylene Lipid." *Angew Chem Int. Ed.* 40:172-174, no month.

Nissen et al. (2001) "Interface dynamics of Lipid Membrane Spreading on Solid Surfaces." *Physical Review Letters* 86:1904-1907. vol. 86, No. 9 Feb. 26, 2001.

Overney et al. (1994) "Force Microscopy Study of Friction and Elastic Compliance of Phase-Seperated Organic Thin Films." *Langmuir* 10:1281-1288. vol. 10, No. 4, no month.

Parikh et al. (1999) "Infrared Spectroscopic Characterization of Lipid-Alkylslloxane Hybrid Bilayer Membranes at Oxide Substrates." *Langmuir* 15:5369-5381, Jul.

Plant (1993) "Self-Assembled Phospholipik/Alkanethiol Biomimetic Bilayers on Gold." *Langmuir* 9:2764-2767, no month, but after Aug. 23, 1993.

Rosenberger et al. (2000) "Microbial Pathogenesis: Lipid Rafts as Pathogen Portals." *Current Biology* 10: R823-R825, no month.

Sackmann (1996) "Supported Membranes: Scientific and Practical Applications." *Science* 271:43-48, Jan. 5, 1996.

Sackmann (2000) "Supported Membranes on Soft Polymer Custions: Fabrication, Characterization and Applications." *Trends in Biotechnology* 18:58-64, Feb.

Salome et al. (1998) "Characterization of Membrane Domains by Frap Experiments at Varitable Observation Areas." *Eur Biophys Journal* 27:391-402. no month, but after Jan. 19, 1998.

Sandre et al. (1999) "Dynamics of Transient Pores in Stretched Vesicles." *Proceedings of the National Academy of Sciences USA* 96:10591-10596, Sep.

Simmons and Ikonen (1997) "Functional Rafts in Cell Membranes." *Nature* 387:569-572, Jun.

Singh and Keller (1991) "Atomic Force Microscopy of Supported Planar membrane Bilayers." *Biophysical Journal* 60:1401-1410, Dec.

Sinner and Knoll. (2000) "Functional Tethered Membranes." *Current Opinion in Chemical Biology* 5(6): 705-711, no month.

Sohn et al. (2003) "Crucial Role of Local Peroxynitrite Formation in Neutrophil-induced Endothelial Cell Activation." *Cardiovascular Research* 57(3): 804-815, no month.

Soumpasis (1983) "Theoretical Analysis of Fluorescence Photobleaching Recovery Experiements." *Biophysical Journal* 41:95-97, Jan.

Ulman et al. (1997) "Micropattering Fluid Membranes." *Advanced Matter* 9(14): 1121-1123, no month.

Van Meer (2002) "The Different Hues of Lipid Rafts." *Science* 296:855-857, May 3, 2002.

Van Oudenaarden and Boxer (1999) "Brownian Ratchets: Molecular Separations in Lipid Bilayers Supported on Patterned Arrays." *Science* 285(5430):1046-1048, Aug. 13, 1999.

Wentworth et al. (2002) "Evidence for Antibody-Catalyzed Ozone Formation in Bacterial Killing and Inflammation." *Science* 298:2195-2199, Aug. 27,2002.

Curtis and Barnes, "How Cells Are Organized" Biology-5[th]Edition, Chapter 5, page 105, no month 1989.

Plant, Supported Hybrid Bilayer Membranes as Rugged Cell Membrane Mimics, Langmuir, 15: 5128-5135, no month 1999.

Tarek et al., Molecular Dynamics Simulations of Supported Phospholipid/Alkanethiol Bilayers on a Gold(111) Surface, Biophysical Journal, vol. 77:964-972, Aug. 1999.

\* cited by examiner 0 min → 60 min t = 1hr        t = 96hr

DIRECT MICRO-PATTERNING OF LIPID BILAYERS USING UV LIGHT AND SELECTED USES THEREOF

CROSS-REFERENCE TO RELATED APPLICATIONS

This application is related to, and claims priority from, Provisional U.S. Patent Application Nos. 60/422,902 filed Oct. 30, 2002; 60/423,327, filed Oct. 31, 2002; 60/469,928, filed May 12, 2003; and 60/496,256, filed Aug. 18, 2003, the full disclosures of which are hereby incorporated herein by reference in their entirety for all purposes.

FIELD OF THE INVENTION

The current invention relates primarily to the field of construction of micro-patterned lipid bilayers and to methods of their modification and use. For example, the invention includes UV micro-patterning of lipid bilayers and optionally, e.g., refunctionalization or backfilling, and uses of such resulting micro-patterned lipid bilayers.

BACKGROUND OF THE INVENTION

The construction and use of various types of biological micro-arrays has greatly expanded in recent years. For example, use of DNA micro-arrays has facilitated such procedures as analysis of gene expression, sequencing, genomic analysis, etc., through increases in throughput and the like. Additionally, some types of protein micro-arrays that include, e.g., antibodies, can be synthesized and used for antigen screening, etc. However, construction of micro-arrays involving membranes (e.g., lipid bilayers) has lagged behind development of other types of micro-arrays. Additionally, construction of more finely tuned and robust protein arrays, especially those involving membrane-bound or membrane-associated proteins, has also proven problematic.

A welcome addition to the art would be a convenient, stable method of creating micro-arrays of lipid bilayers and of creating micro-arrays of lipid bilayers comprising such additions as proteins (especially membrane bound proteins), non-biological moieties, etc. The present invention provides these and other benefits which will be apparent upon examination of the following.

SUMMARY OF THE INVENTION

In various embodiments, the invention provides methods, systems, and kits for construction of patterned lipid bilayer arrays and uses thereof, as well as the resulting patterned lipid bilayer membranes, systems, kits, and arrays.

In some embodiments, the invention comprises a method of constructing one or more patterned lipid bilayer by providing at least a first lipid bilayer, providing one or more source of UV light (optionally a number of different UV light sources of, optionally, different wavelengths, etc.), providing one or more patterned UV-opaque mask (comprising one or more UV-transparent area at one or more specific location in the UV mask) between the source of UV light and the at least first lipid bilayer, and, exposing the lipid bilayer to the UV light through the one or more patterned UV-opaque mask. Such embodiments thereby construct a patterned lipid bilayer comprising one or more non-lipid area which corresponds (e.g., in location, arrangement, etc.) to the one or more UV-transparent area in the UV mask. In such embodiments, the first lipid bilayer optionally comprises, e.g., a supported lipid bilayer, a tethered lipid bilayer, a polymer-cushioned lipid bilayer, a lipid bilayer comprising proteins in a proteo-lipidic mixture, or a hybrid lipid bilayer comprising an outer lipid layer and an inner self-assembled monolayer. Such first lipid bilayer is optionally a planar lipid bilayer, or is optionally a non-planar lipid bilayer. Some embodiments can optionally include, e.g., those in which the non-planar lipid bilayer comprises, e.g., a spherical lipid bilayer such as on a cell or liposome, a cylindrical lipid bilayer, or a selected three-dimensional lipid bilayer. In other words, the surface shape or topography of the bilayers to be patterned is not typically limiting upon the current invention. Also, the first lipid bilayer optionally comprises a bilayer supported on a planar substrate or a bilayer supported on a non-planar substrate. Additionally, in some such embodiments, the lipid bilayer comprises a first lipid layer and at least a second lipid layer. Such first and second (or "top" and "bottom") lipid layers can optionally comprise substantially similar lipid profiles ("profile" herein corresponding to, e.g., number and/or type of lipids in the bilayers), identical lipid profiles, or different lipid profiles. Furthermore, either the first or second lipid layer in the lipid bilayer can optionally comprise a synthetic lipid layer. The source of UV light in such embodiments optionally comprises an adjustable source of UV light, which can be, e.g., a tungsten-halogen lamp, a xenon-arc lamp, a mercury lamp, an excimer laser, or other similar UV source which produces the appropriate wavelength light (i.e., typically from between about 184 nm to about 257 nm, or, e.g., 184.9 nm, 253.7 nm). The patterned UV-opaque mask within such embodiments optionally comprises a plurality of UV-transparent areas. Again, it will be appreciated that such UV-transparent areas in the mask will thus lead to corresponding lipid-free areas in the underlying lipid bilayer membrane. Thus, discussion of "density" and "sizes" of UV-transparent areas in the mask are also applicable to the lipid-bilayer membrane itself (e.g., resulting in such corresponding densities, sizes, etc. of lipid-free areas in the lipid bilayer membranes). In such embodiments, the patterned UV-opaque mask can comprise one or more UV-transparent area, which transparent areas optionally comprise any desired size (e.g., in diameter, etc.) which fits within the dimensions of the UV-opaque mask. Also, such UV-transparent areas are optionally contiguous with one another (as optionally are the UV-opaque areas which correspond to the unaffected lipid bilayer membrane areas in the underlying membrane). For example, in some embodiments herein, the UV-transparent areas range in size (e.g., in at least one dimension of length or width) from 5 millimeters to about 0.1 micrometers or less, or optionally from about 2 millimeters to about 0.5 micrometers or less; from about 1 millimeter to about 1 micrometer or less; from about 500 micrometers to about 5 micrometers or less; from about 250 micrometers to about 10 micrometers or less; from about 100 micrometers to about 15 micrometers or less; or from about 75 micrometers to about 25 micrometers or less. In other embodiments the size of such UV-transparent areas comprises around 200–300 nanometers. Additionally, the shape of such UV-transparent areas can also be of any desirable conformation which fits within the dimensions of the UV-opaque mask. For example, some embodiments herein comprise UV-transparent areas comprising, e.g., geometric patterns, squares, lines, circles, grids, letters, etc. Also, in some such embodiments, the patterned UV-opaque mask comprises any number and/or conformation/arrangement of UV-transparent areas which fits within the dimensions of the UV-opaque mask. Thus, in some embodiments, the density of micro-patterned areas (e.g., corresponding to emptied areas within a bilayer or islands of bilayer surrounded by emptied areas in a primary bilayer) comprises, e.g., from about 144 micro-patterned areas to about 2200 or more micro-patterned areas per square centimeter. The distance between the UV-transparent areas in the UV-opaque masks herein can optionally comprise a range of possible distances (again, varying upon, e.g., the number and sizes of the UV-transparent areas and the size of the UV-opaque mask). For example, in some embodiments herein, the distance between two or more UV-transparent areas comprises from about 2 micrometers to about 3 millimeters or more. Such UV-opaque masks are also of myriad possible sizes, and typically are of the same size (in dimensions as the lipid bilayer membrane to be patterned). For example, some embodiments herein comprise masks of about 5 centimeters by 5 centimeters or 2.5 centimeters by 7.5 centimeters or the like (e.g., 2 cm by 2 cm, 1 cm by 1 cm, 0.5 cm by 0.5 cm, 0.25 cm by 0.25 cm, 0.1 cm by 0.1 cm, 0.01 cm by 0.01 cm, or even smaller, as well as differing, dimensions). Such embodiments also optionally comprise any micro-patterned bilayers as are constructed through such methods.

In other aspects, the current invention comprises a method of constructing one or more modified lipid bilayer by: providing at least a first primary lipid bilayer, providing one or more source of UV light, providing one or more patterned UV-opaque mask (which has one or more UV-transparent area at one or more specific locations) between the source of UV light and the primary lipid bilayer, exposing the primary lipid bilayer to the UV light through the patterned UV-opaque mask (thus, constructing a patterned lipid bilayer comprising one or more non-lipid area that corresponds to the one or more UV-transparent area in the UV mask), providing at least a first secondary lipid bilayer, and contacting the one or more patterned lipid bilayer with the secondary lipid bilayer, which then localizes within the one or more non-lipid area in the patterned lipid bilayer. In some such embodiments, the UV mask comprises a plurality of UV masks and the secondary lipid bilayer comprises a plurality of secondary lipid bilayers. Additionally, each member of the plurality of UV masks optionally comprises a different pattern and each member of the plurality of secondary lipid bilayers optionally comprises a different secondary lipid bilayer. Embodiments such as this one optionally further comprise repeating the steps for creation of the modified lipid bilayer for substantially all members of the plurality of UV masks and/or for substantially all members of the plurality of secondary lipid bilayers. Such embodiments thereby create modified lipid bilayers containing a plurality of different secondary lipid bilayers, optionally at different locations within the primary lipid bilayer (i.e., such sites corresponding to the UV-transparent areas of the plurality of masks). In such methods, the first primary lipid bilayer optionally comprises, e.g., a supported lipid bilayer, a tethered lipid bilayer, a polymer-cushioned lipid bilayer, a lipid bilayer comprising proteins in a proteolipidic mixture, or a hybrid lipid bilayer comprising an outer lipid layer and/or an inner self-assembled monolayer. Additionally, the first primary lipid bilayer optionally comprises a planar lipid bilayer or a non-planar lipid bilayer. Such non-planar lipid bilayers can optionally comprise, e.g., a spherical lipid bilayer such as a cell or liposome, a cylindrical lipid bilayer, a selected three-dimensional lipid bilayer, etc. Also, such first lipid bilayer can optionally comprise a bilayer supported on a planar substrate or a bilayer supported on a non-planar substrate. In yet other such embodiments, the first primary lipid bilayer optionally comprises a first lipid layer and at least a second lipid layer. Such first and second layers can optionally comprise substantially similar lipid profiles, identical lipid profiles, or different lipid profiles. Such layers can also optionally comprise one or more synthetic lipid layer(s). In such embodiments, the one or more source of UV light can optionally comprise an adjustable source of UV light (e.g., a tungsten-halogen lamp, a xenon-arc lamp, a mercury lamp, an excimer laser, or other similar source which produces light in the proper UV wavelength, such as optionally from between about 184 nm to about 257 nm, or about 184.9 nm and about 253.7 nm). In such embodiments, the patterned UV-opaque mask can comprise one or more UV-transparent area, which transparent areas optionally comprise any desired size (e.g., in diameter, etc.) which fits within the dimensions of the UV-opaque mask. For example, in some embodiments herein, the UV-transparent areas range in size (e.g., in at least one dimension of length or width) from 5 millimeters to about 0.1 micrometers or less, or optionally from about 2 millimeters to about 0.5 micrometers or less; from about 1 millimeter to about 1 micrometer or less; from about 500 micrometers to about 5 micrometers or less; from about 250 micrometers to about 10 micrometers or less; from about 100 micrometers to about 15 micrometers or less; or from about 75 micrometers to about 25 micrometers or less. Here again, as will be apparent throughout, discussion of density, size, arrangement, contiguity, distance between, etc. of UV-transparent and UV-opaque areas in a mask corresponds to similar densities, sizes, etc. of lipid bilayer membrane areas and lipid-free areas in the underlying membrane. In other embodiments, the size of such UV-transparent areas comprises around 200–300 nanometers. Additionally, the shape of such UV-transparent areas can also be of any desirable conformation which fits within the dimensions of the UV-opaque mask. For example, some embodiments herein comprise UV-transparent areas comprising, e.g., geometric patterns, squares, lines, circles, grids, letters, etc. Also, in some such embodiments, the patterned UV-opaque mask comprises any number and/or conformation/arrangement of UV-transparent areas which fits within the dimensions of the UV-opaque mask. The one or more lipid-free areas (and additionally and/or alternatively the one or more lipid bilayer membrane areas) are optionally contiguous with one another. Thus, in some embodiments, the density of micro-patterned areas (e.g., emptied areas within a bilayer or islands of bilayer surrounded by emptied areas) comprises, e.g., from about 144 micro-patterned areas to about 2,200 or more micropatterned areas per square centimeter. The distance between the UV-transparent areas in the UV-opaque masks herein can optionally comprise a range of possible distances (again, varying upon, e.g., the number and sizes of the UV-transparent areas and the size of the UV-opaque mask). For example, in some embodiments herein, the distance between two or more UV-transparent areas comprises from about 2 micrometers to about 3 millimeters or more. Such UV-opaque masks are also of myriad possible sizes, and typically are of the same size (in dimensions as the lipid bilayer membrane to be patterned). For example, some embodiments herein comprise masks of about 5 centimeters by 5 centimeters or 2.5 centimeters by 7.5 centimeters or the like (e.g., 2 cm by 2 cm, 1 cm by 1 cm, 0.5 cm by 0.5 cm, 0.25 cm by 0.25 cm, 0.1 cm by 0.1 cm, 0.01 cm by 0.01 cm, or even smaller, as well as differing, dimensions). The secondary lipid bilayer(s) involved in such embodiments can optionally comprise one or more of, e.g.: a lipid raft, a lipid-coated bead, a liposome, a lipid vesicle, a polymerizable lipid, or a proteo-liposome. Furthermore, the secondary lipid bilayer and the primary lipid bilayer can comprise, e.g.: substantially similar lipid bilayers, identical lipid bilayers, or different lipid bilayers (e.g., wherein the secondary lipid bilayer comprises a different lipid profile than the lipid profile of the primary lipid bilayer, or wherein the secondary lipid bilayer comprises a different amount of proteins than primary lipid bilayer, or wherein the secondary lipid bilayer comprises a different type of proteins than the primary lipid bilayer, or wherein the secondary lipid bilayer comprises a different lipid diffusion coefficient than the primary lipid bilayer, or wherein the secondary lipid bilayer comprises a different amount of cholesterol than the primary lipid bilayer, etc.). Such embodiments also comprise any micro-patterned bilayers as are constructed through such methods.

In yet other embodiments herein, the invention comprises a method of constructing one or more chimeric lipid bilayer by: providing at least a first lipid bilayer, providing one or more source of a UV light, providing one or more patterned UV-opaque mask (comprising one or more UV-transparent area at one or more specific location in the mask) between the source of UV light and lipid bilayer, exposing the lipid bilayer to the UV light through the one or more patterned UV-opaque mask (thus, constructing at least one patterned lipid bilayer comprising one or more non-lipid area corresponding to the one or more UV-transparent area in the mask), providing at least a first secondary or refunctionalized material, and contacting the one or more patterned lipid bilayer with the secondary material, which localizes within the one or more non-lipid area in the patterned lipid bilayer. In some such embodiments, the UV mask comprises a plurality of UV masks (each optionally comprising a different pattern) and the secondary material comprises a plurality of secondary materials (each optionally comprising a different secondary material) and the method involves repeating the patterning/chimera forming steps for substantially all members of the plurality of secondary materials. Thus, one or more chimeric lipid bilayer containing a plurality of different secondary materials is created. In such embodiments, the primary lipid bilayer optionally comprises, e.g., a supported lipid bilayer, a tethered lipid bilayer, a polymer-cushioned lipid bilayer, a lipid bilayer comprising proteins in a proteo-lipidic mixture, a hybrid lipid bilayer comprising an outer lipid layer and an inner self-assembled monolayer, a planar lipid bilayer, or a non-planar lipid bilayer. Such first primary lipid bilayer also optionally comprises, e.g., a spherical lipid bilayer such as a cell or liposome, a cylindrical lipid bilayer, a selected three-dimensional lipid bilayer, etc. Additionally, the first lipid bilayer can optionally comprise a bilayer supported on a planar or a non-planar substrate. Also in such embodiments, the first primary lipid bilayer can comprise a first lipid layer and at least a second lipid layer. Such layers can optionally comprise such things as: substantially similar lipid profiles, identical lipid profiles, or different lipid profiles. Such lipid layers can also optionally comprise a synthetic lipid layer. Furthermore, in such embodiments, the source of UV light optionally comprises an adjustable source of UV light, e.g., a tungsten-halogen lamp, a xenon-arc lamp, an excimer laser, a mercury lamp, and/or other similar UV source which produces light at the appropriate wavelength (e.g., from between about 184 nm to about 257 nm, or 184.9 nm and 253.7 nm). In such embodiments, the patterned UV-opaque mask can comprise one or more UV-transparent area, which transparent areas optionally comprise any desired size (e.g., in diameter, etc.) which fits within the dimensions of the UV-opaque mask. For example, in some embodiments herein, the UV-transparent areas range in size (e.g., in at least one dimension of length or width) from 5 millimeters to about 0.1 micrometers or less, or from about 2 millimeters to about 0.5 micrometers or less; from about 1 millimeter to about 1 micrometers or less; from about 500 micrometers to about 5 micrometers or less; from about 250 micrometers to about 10 micrometers or less; from about 100 micrometers to about 15 micrometers or less; or from about 75 micrometers to about 25 micrometers or less. In other embodiments, the size of such UV-transparent areas comprises around 200–300 nanometers. Additionally, the shape of such UV-transparent areas can also be of any desirable conformation which fits within the dimensions of the UV-opaque mask. For example, some embodiments herein comprise UV-transparent areas comprising, e.g., squares, lines, circles, grids, letters, etc. Such transparent areas and/or opaque areas (again, as explained above, such will also correspond to and include the resulting lipid and lipid-free areas in the patterned membrane) can optionally comprise contiguous transparent areas and/or contiguous opaque areas. Also, in some such embodiments, the patterned UV-opaque mask comprises any number and/or conformation/arrangement of UV-transparent areas which fits within the dimensions of the UV-opaque mask. Thus, in some embodiments, the density of micro-patterned areas (e.g., emptied areas within a bilayer or islands of bilayer surrounded by emptied areas) comprises, e.g., from about 144 micro-patterned areas to about 2200 or more micro-patterned areas per square centimeter. The distance between the UV-transparent areas in the UV-opaque masks herein can optionally comprise a range of possible distances (again, varying upon, e.g., the number and sizes of the UV-transparent areas and the size of the UV-opaque mask). For example, in some embodiments herein, the distance between two or more UV-transparent areas comprises from about 10 micrometers to about 3 millimeters or more. Such UV-opaque masks are also of myriad possible sizes, and typically are of the same size (in dimensions as the lipid bilayer membrane to be patterned). For example, some embodiments herein comprise masks of about 5 centimeters by 5 centimeters or 2.5 centimeters by 7.5 centimeters or the like. Some other embodiments herein comprise masks of about 5 centimeters by 5 centimeters or 2.5 centimeters by 7.5 centimeters or the like (e.g., 2 cm by 2 cm, 1 cm by 1 cm, 0.5 cm by 0.5 cm, 0.25 cm by 0.25 cm, 0.1 cm by 0.1 cm, 0.01 cm by 0.01 cm, or even smaller, as well as differing, dimensions). Also in such embodiments, the refunctionalization material or component can optionally comprise one or more of: a cell, a protein, a glass bead, a latex bead, a bilayer coated bead, a membrane compatible amphiphilic polymer, a nanocrystal, a colloid, a quantum-dot material, a metal, a metal bead, a polymerizable precursor molecule or the like. In yet other embodiments, the refunctionalization material optionally undergoes a spatially confined chemical reaction. Such reaction can include, e.g., an electrochemical metal reduction, a polymerization, a protein-ligand reaction, a cell-capture, etc. Such embodiments also comprise any patterned chimeric bilayers as are constructed through such methods.

In other aspects, the current invention comprises a system or kit for construction of one or more patterned lipid bilayer membrane. Such system or kit comprises: one or more source of an adjustable UV light, a source of one or more primary lipid bilayer membrane, one or more UV-opaque mask (comprising one or more UV transparent area) that is positioned between the UV light and the primary lipid bilayer membrane and one or more module for controllably positioning the lipid bilayer in relation to the UV opaque mask and the UV light. Other embodiments comprise a system or kit for construction of one or more modified or chimeric lipid bilayer membrane. Such system or kit comprises: one or more source of adjustable UV light, a source of one or more primary lipid bilayer membrane, one or more source of one or more refunctionalization component, one or more UV-opaque mask that comprises one or more UV transparent area and that is positioned between the UV light and the primary lipid bilayer membrane, and one or more module for controllably positioning the lipid bilayer membrane in relation to the UV opaque mask and the UV light. The refunctionalization component(s) in such systems/kits can optionally comprise, e.g., one or more secondary lipid bilayer membrane or one or more non-lipid bilayer membrane material (e.g., a cell, a protein, a glass bead, a latex bead, a bilayer coated bead, a membrane compatible amphiphilic polymer, a nanocrystal, a colloid, a quantum-dot material, a metal, a metal bead, a polymerizable precursor molecule or the like). In other embodiments, the systems or kits optionally comprise one or more source of one or more lipid bilayer membrane buffer (e.g., water, PBS, etc.). Also, in other embodiments, the systems/kits optionally comprise a timer device which selectably controls the UV light (e.g., controls the duration of the UV light). Additionally, other optional embodiments comprise one or more device for controllably positioning the UV mask in relation to the UV light and the lipid bilayer membrane. Yet other embodiments comprise one or more packaging materials, instructions for using the systems/kits to produce one or more patterned lipid bilayer membrane, modified lipid bilayer membrane, or chimeric lipid bilayer membrane, or one or more containers for holding one or more component of the system/kit. Other embodiments also optionally comprise controllable incubation devices and the like appropriate for refunctionalization or any refunctionalization component into the micro-patterned array.

In yet other aspects, the current invention comprises a system or kit for making one or more patterned, modified, or chimeric lipid bilayer membrane. Such systems/kits for constructing a patterned, modified, or chimeric lipid bilayer membrane typically and optionally comprise: one or more lipid bilayer membrane; one or more UV-opaque mask (which mask comprises one or more UV transparent area) and instructions for constructing a patterned lipid bilayer by selectively exposing the lipid bilayer to UV light passing through the mask. Additionally such systems or kits optionally comprise, e.g., one or more adjustable UV light, one or more timer device (which, e.g., selectably controls the UV light), one or more packaging materials, one or more container for holding one or more component of the system/kit, one or more lipid bilayer membrane buffer, and one or more module for controllably positioning the UV mask in relation to the UV light and the lipid bilayer membrane.

While it will be appreciated that the current invention comprises myriad embodiments of systems/kits/micro-patterned bilayers, etc. (and specific examples herein should not be construed as limiting), certain examples include, e.g., systems/kits comprising environmental monitoring systems or kits for detecting or classifying one or more environmental moiety. In such exemplary system/kits the one or more refunctionalization component (and/or a component of the primary bilayer membrane) typically binds to or otherwise indicates the presence of the one or more environmental moiety (which optionally comprises one or more of, e.g., a bacteria, a bacterial toxin, a virus, a prion, a fungus, a fungal toxin, a chemical agent, etc.). Examples of such environmental moieties optionally include one or more of, or portions (e.g., such as surface antigens/markers) of, e.g., *Bacillus anthracis, Clostridium botulinum, Clostridium botulinum* toxin, *Yersinia pestis, Variola* major, *Francisella tularensis*, Hemorrhagic fever, a Filovirus, an Arenoviruses, Ebola virus, Marburg virus, Lassa virus, Machupo virus, a Hanta virus, *Coxiella burnetii*, a brucellosis causing bacterium, epsilon toxin of *Clostridium perfringens*, a *Salmonella* species, *Escherichia coli* 0157:H7, *Shigella, Burkholderia mallei, Burkholderia pseudomallei, Chlamydia psittaci*, ricin toxin, Staphylococcal enterotoxin B, *Rickettsia prowazekii*, a viral encephalitis virus, an alphavirus, Venezuelan equine encephalitis virus, Eastern equine encephalitis virus, Western equine encephalitis virus, a flavivirus, St. Louis encephalitis virus, *Vibrio cholerae, Vibrio cholerae* toxin, *Cryptosporidium parvum*, Nipah virus, distilled mustard, Lewisite, mustard gas, nitrogen mustard, phosgene oxime, ethyldicholoarsine, Lewisite 1 (L-1), Lewisite 1 (L-2), Lewisite 1 (L-3), methyldichloroarsine, mustard/Lewisite, phenodichloroarsine, sesqui mustard, arsine, cyanogen chloride, hydrogen chloride, hydrogen cyanide, chlorine, diphosgene, cyanide, nitrogen oxide, perfluorori-sobutylene, phosgene, red phosphorous, sulfur trioxide-chlorosulfonic acid, teflon and perfluororisobutylene, titanium tetrachloride, zinc oxide, Agent 15, BZ, canniboids, fentanyls, LSD, phenothiazines, cyclohexyl sarin, GE, sarin, soman, tabun, VE, VG, V-gas, VM, VX, bromobenzylcyanide, chloroacetophenone, chloropicrin, CN in benzene and carbon tetrachloride, CN in chloroform, CN and chloropicrin in chloroform, CR, CS, adamsite, diphenylchloroarsine, diphenylcyanoarsine, or a fusarium toxin. The refunctionalization component in such system/kits optionally comprises: an antibody against the environmental moiety, a specific protein which selectively binds to or otherwise indicates the presence the environmental moiety, a specific membrane protein which selectively binds to or otherwise indicates the presence the environmental moiety, a specific membrane lipid which selectively binds to or otherwise indicates the presence the environmental moiety, or a specific chemical element or compound which binds to or otherwise indicates the presence of the environmental moiety. As explained in more detail below, such system/kits are optionally used for, e.g., detection of environmental pollution, food-borne contamination, accidental or intentional release of pathogenic agents and/or potentially harmful chemicals, etc.

Other exemplary system/kits of the current invention include those comprising diagnostic systems or kits for detecting or identifying one or more pathogen in an organism. In such system/kits the one or more refunctionalization component (and/or a component of the primary bilayer membrane) binds to or otherwise indicates a presence of the one or more pathogen or of one or more pathogen-related moiety (e.g., one or more of: a bacteria, a virus, a prion, a fungus, an infectious parasite, etc.). In such systems/kits, the one or more pathogen-related moiety can optionally comprise one or more of, e.g., an antibody of the organism against the one or more pathogen, a non-organism byproduct of the one or more pathogen, or a moiety produced by the organism in response to the one or more pathogen, etc.

Yet another exemplary system/kit of the invention comprises a system or kit for detecting or identifying one or more nucleic acid sequence in one or more genome, wherein the refunctionalization component (and/or a component of the primary bilayer membrane) binds to or otherwise indicates the presence of the one or more nucleic acid sequence. Such one or more nucleic acid sequence optionally can indicate a presence of one or more disease (e.g., a congenital disease) in an organism which comprises the one or more genome. Additionally, the one or more nucleic acid sequence optionally comprises a plurality of nucleic acid sequences and binding of the one or more nucleic acid sequence thus optionally identifies one or more organism comprising the one or more genome of the one or more nucleic acid.

Still other exemplary system/kits of the invention comprise drug profiling systems or kits for detecting or identifying one or more drug, or the prior presence of such, within an organism. In such options, the refunctionalization component (and/or a component of the primary bilayer membrane) binds to or otherwise indicates a presence (or prior presence) of the one or more drug within the organism. Such systems/kits can optionally be tuned to detect the presence/prior presence of one or more of any desired drug product (e.g., as in illegal narcotics, legally prescribed pharmaceuticals, etc.). For example, such systems/kits can optionally detect, e.g., one or more of: a cannaboid, cocaine, a barbiturate, methaqualone, sopor, parest, quaalude, mecquin, a benzodiazepine, chloral hydrate, phencyclidine, LSD, mescaline, peyote, psilocybin, DMY, DET, psilocyn, an amphetamine, an amphetamine derivative, heroin, codeine, morphine, an opiate, meperidine, hydromorphone, methadone, methamphetamines, phenmetrazine, etc. In typical embodiments such detection is performed on a human subject (but other organisms are also optionally screened for drug presence). Such systems/kits also optionally further comprise wherein the presence or prior presence of the one or more drug is detected or identified through profiling or examination of one or more of: blood, saliva, hair, skin, or mucus of the organism.

Another exemplary system/kit of the invention comprises a system or kit for identifying the effect or efficacy of one or more putative therapeutic or preventative drug on one or more organism (e.g., a drug screening system/kit). In such situations, the one or more refunctionalization component (and/or a component of the primary bilayer membrane) binds to or otherwise indicates the effect or efficacy of the putative drug. The secondary component optionally comprises one or more moiety from the organism that is capable of interacting with one or more infectious agent or one or more product of one or more infectious agent. Thus, the one or more putative drug optionally binds to or alters the one or more infectious agent. Alternatively, the one or more putative drug binds to or alters the one or more moiety of the organism (which moiety would interact with the infectious agent).

In some systems/kits herein, the one or more refunctionalization component comprises one or more secondary lipid bilayer membrane, one or more non-lipid bilayer material, or one or more of: a cell, a protein, a glass bead, a latex bead, a bilayer coated bead, a membrane compatible amphiphilic polymer, a nanocrystal, a colloid, a quantum-dot material, a metal, a metal bead, or a polymerizable precursor molecule.

In yet other aspects, the current invention comprises a controllably patterned lipid bilayer which comprises multiple lipid-free areas within a lipid bilayer membrane (i.e., at least two stable lipid-free areas within a lipid bilayer membrane, thus, forming a micro-pattern). Such embodiments also optionally include wherein the lipid bilayer comprises, e.g.: a supported lipid bilayer (typically), a tethered lipid bilayer, a polymer-cushioned lipid bilayer, a lipid bilayer comprising proteins in a proteo-lipidic mixture, and a hybrid lipid bilayer comprising an outer lipid layer and an inner self-assembled monolayer. In such patterned bilayers, the lipid-free areas are not separated from the lipid bilayer by any physical barrier such as a metal/ink/polymer/etc. wall or deposit left either intentionally or unintentionally, e.g., as a result of stamp patterning, etc. between the lipid-free and non-lipid-free areas. In some such embodiments, the density of the lipid-free areas comprises from about 144 lipid-free areas per square centimeter of lipid bilayer to about 2200 or more lipid-free areas per square centimeter of lipid bilayer. Other embodiments comprise from about 200 to about 1500 lipid-free areas, or from about 500 to about 1000 lipid-free areas per square centimeter of lipid bilayer. Additionally, in some embodiments, the arrangement of lipid/lipid-free areas within the lipid bilayer membrane comprises islands of lipid bilayer areas surrounded by lipid-free areas. In such case, the density can optionally be considered as density of lipid areas per square centimeter.

Other aspects of the invention comprise a modified lipid bilayer comprised of a primary lipid bilayer and one or more secondary lipid bilayer wherein the areas of secondary lipid bilayer are controllably localized within specific regions of the primary lipid bilayer. Such aspects also include typical embodiments wherein the one or more region/area of the secondary lipid bilayer is not separated by any physical barriers from the primary lipid bilayer regions. The embodiments can include instances of multiple regions/areas of secondary lipid bilayers wherein the regions/areas are of the same secondary lipid bilayer type. However, such embodiments also include wherein the primary lipid bilayer comprises multiple secondary lipid bilayer regions/areas of which there are multiple types (i.e., a first type of secondary lipid bilayer, a second type of secondary lipid bilayer, etc.). Such embodiments also optionally include wherein the primary lipid bilayer comprises, e.g., a supported lipid bilayer, a tethered lipid bilayer, a polymer-cushioned lipid bilayer, a lipid bilayer comprising proteins in a proteo-lipidic mixture, and a hybrid lipid bilayer comprising an outer lipid layer and an inner self-assembled monolayer. The one or more secondary lipid bilayers can optionally comprise such compositions as: lipid rafts, lipid vesicles, lipid-coated beads, liposomes, polymerizable lipids, and proteo-liposomes. Additionally, the secondary lipid bilayer and the primary lipid bilayer can optionally comprise: substantially similar lipid bilayers, identical lipid bilayers, or different bilayers. If they comprise different types of bilayers then they can optionally comprise: different lipid profiles, different amounts of proteins, different types of proteins, different amounts of cholesterol, or different diffusion coefficients. In some embodiments, the areas/regions of secondary lipid bilayers are stably localized within the primary lipid bilayer, while in other embodiments, the secondary lipid bilayers can diffuse out into/with the primary lipid bilayer over varying time courses (e.g., some secondary lipid bilayers can diffuse at greater rates than others (if they do so at all)). Also, in some embodiments, the secondary lipid bilayer comprises a plurality of lipid bilayers, e.g., in a plurality of regions or areas upon the primary lipid membrane. The density of such secondary lipid bilayers in the primary lipid bilayer can be from about 144 or less secondary areas to about 2200 or more, from about 200 to about 1500 or more, or from about 500 to about 100 or more secondary areas per square centimeter of primary lipid bilayer. Additionally, as explained previously, in some embodiments, the arrangement of lipid/lipid-free areas within the lipid bilayer. membrane comprises islands of lipid bilayer areas surrounded by lipid-free areas (e.g., instead of "holes" of lipid-free areas surrounded by lipid membranes). In such cases, the density, etc. can optionally be considered as density of lipid areas per square centimeter.

In other aspects, the current invention comprises a chimeric lipid bilayer with a primary lipid bilayer and one or more refunctionalization material that is controllably localized within the primary lipid bilayer. Such embodiments also include wherein the primary lipid bilayer and the refunctionalization material are not separated by any physical barrier. Such primary lipid bilayers can optionally be: supported lipid bilayers, tethered lipid bilayers, polymer-cushioned lipid bilayers, lipid bilayers with proteins in a proteo-lipidic mixture, or hybrid lipid bilayers of an outer lipid layer and an inner self-assembled monolayer. Furthermore, the refunctionalization material in such chimeric lipid bilayers can optionally comprise, e.g., a cell, a protein, a glass bead, a metal bead, a latex bead, a bilayer coated bead, a membrane compatible amphiphilic polymer, a nanocrystal, a colloid, a quantum-dot material, a metal, a metal bead, or a polymerizable precursor molecule. In some embodiments, the refunctionalization material can comprise a plurality of different refunctionalization materials (or even a plurality of multiple instances of the same type of refunctionalization material). In some embodiments, the density of occurrences of the refunctionalization material in the primary lipid bilayer can be from about 144 regions/areas of refunctionalization material to about 2200 or more regions/areas of refunctionalization material per square centimeter of primary lipid bilayer. Other instances include densities of, e.g., from 200 to about 2000 refunctionalization regions/areas, about 500 to about 1500, or about 700 to about 1200 refunctionalization regions/areas per square centimeter of primary lipid bilayer.

In some embodiments herein, the lipid bilayers of the invention (e.g., a modified and/or chimeric lipid bilayer), comprise micro-arrays for detecting or classifying, e.g., one or more environmental moiety. In such micro-arrays the one or more refunctionalization component binds to or otherwise indicates the presence of the one or more environmental moiety (e.g., one or more of: a bacteria, a bacterial toxin, a virus, a prion, a fungus, a fungal toxin, or a chemical agent). Such lipid bilayer optionally detects or classifies such environmental moieties (including sub-parts such as antigens and/or surface markers) as, e.g., one or more of: *Bacillus anthracis, Clostridium botulinum, Clostridium botulinum* toxin, *Yersinia pestis, Variola* major, *Francisella tularensis*, Hemorrhagic fever, a Filovirus, an Arenoviruses, Ebola virus, Marburg virus, Lassa virus, Machupo virus, a Hanta virus, *Coxiella burnetii*, a brucellosis causing bacterium, epsilon toxin of *Clostridium perfringens*, a *Salmonella* species, *Escherichia coli* 0157:H7, *Shigella, Burkholderia mallei, Burkholderia pseudomallei, Chlamydia psittaci*, ricin toxin, Staphylococcal enterotoxin B, *Rickettsia prowazekii*, a viral encephalitis virus, an alphavirus, Venezuelan equine encephalitis virus, Eastern equine encephalitis virus, Western equine encephalitis virus, a flavivirus, St. Louis encephalitis virus, *Vibrio cholerae, Vibrio cholerae* toxin, *Cryptosporidium parvum*, Nipah virus, distilled mustard, Lewisite, mustard gas, nitrogen mustard, phosgene oxime, ethyldicholoarsine, Lewisite 1 (L-1), Lewisite 1 (L-2), Lewisite 1 (L-3), methyldichloroarsine, mustard/Lewisite, phenodichloroarsine, sesqui mustard, arsine, cyanogen chloride, hydrogen chloride, hydrogen cyanide, chlorine, diphosgene, cyanide, nitrogen oxide, perfluororisobutylene, phosgene, red phosphorous, sulfur trioxide-chlorosulfonic acid, teflon and perfluororisobutylene, titanium tetrachloride, zinc oxide, Agent 15, BZ, canniboids, fentanyls, LSD, phenothiazines, cyclohexyl sarin, GE, sarin, soman, tabun, VE, VG, V-gas, VM, VX, bromobenzylcyanide, chloroacetophenone, chloropicrin, CN in benzene and carbon tetrachloride, CN in chloroform, CN and chloropicrin in chloroform, CR, CS, adamsite, diphenylchloroarsine, diphenylcyanoarsine, or a fusarium toxin. In such lipid bilayer micro-arrays, the refunctionalization component optionally comprises, e.g., an antibody against the environmental moiety, a specific protein which selectively binds to or otherwise indicates the presence of the environmental moiety, a specific membrane protein which selectively binds to or otherwise indicates the presence of the environmental moiety, a specific membrane lipid which selectively binds to or otherwise indicates the presence of the environmental moiety, or a specific chemical element or compound which binds to or otherwise indicates the presence of the environmental moiety. Furthermore, the invention optionally comprises a kit for detecting or classifying the one or more environmental moiety. The kits comprise such lipid bilayer micro-arrays and one or more of a container for containing the lipid bilayer, packaging material, or instructions for using the lipid bilayer for environmental monitoring.

In additional embodiments, the invention comprises lipid bilayers of the invention (e.g., a modified and/or chimeric lipid bilayer), comprising micro-arrays for detecting or identifying one or more pathogen in an organism. In such instances, the one or more refunctionalization component binds to, or otherwise indicates, a presence of the one or more pathogen (e.g., one or more of: a bacteria, a virus, a prion, a fungus, or an infectious parasite) or of one or more pathogen-related moiety (e.g., one or more of: an antibody of the organism against the one or more pathogen, a non-organism byproduct of the one or more pathogen, or a moiety produced by the organism in response to the one or more pathogen). Furthermore, the invention optionally comprises a kit for detecting or identifying one or more pathogen in an organism. The kits comprise such lipid bilayer micro-arrays and one or more of a container for containing the lipid bilayer, packaging material, or instructions for using the lipid bilayer for detecting/identifying pathogens.

In yet other embodiments herein, the lipid bilayers of the invention (e.g., a modified and/or chimeric lipid bilayer), comprise micro-arrays for detecting or identifying one or more nucleic acid sequence in one or more genome. In such situations, the refunctionalization component binds to or otherwise indicates the presence of the one or more nucleic acid sequence (e.g., one which indicates a presence of disease(s), such as a congenital disease, in an organism). The nucleic acid sequence involved with such micro-arrays can optionally comprises a plurality of nucleic acid sequences. For such lipid bilayer micro-arrays, binding of the one or more nucleic acid sequence can optionally identify one or more organism comprising the one or more genome of the one or more nucleic acid. Furthermore, the invention optionally comprises a kit for detecting or identifying one or more nucleic acid. The kits comprise such lipid bilayer micro-arrays and one or more of a container for containing the lipid bilayer, packaging material, or instructions for using the lipid bilayer for detecting/identifying the one or more nucleic acid.

In other embodiments herein, the lipid bilayers of the invention (e.g., a modified and/or chimeric lipid bilayer), comprises micro-arrays for detecting or identifying one or more drug within one or more organism. In such micro-arrays, the one or more refunctionalization component optionally binds to, or otherwise indicates, a presence (or prior presence) of the one or more drug (e.g., an illegal controlled substance, a legally prescribed pharmaceutical, a cannaboid, cocaine, a barbiturate, methaqualone, sopor, parest, quaalude, mecquin, a benzodiazepine, chloral hydrate, phencyclidine, LSD, mescaline, peyote, psilocybin, DMY, DET, psilocyn, an amphetamine, an amphetamine derivative, heroin, codeine, morphine, an opiate, meperidine, hydromorphone, methadone, methamphetamines, phenmetrazine, etc.) within the organism (e.g., a human). In such micro-arrays the presence or prior presence of the one or more drug is optionally detected or identified through profiling of one or more of: blood, saliva, hair, skin, or mucus of the one or more organism. Furthermore, the invention optionally comprises a kit for detecting or identifying the one or more drug within the organism. The kits comprise such lipid bilayer micro-arrays and one or more of: a container for containing the lipid bilayer, packaging material, or instructions for using the lipid bilayer for detecting or identifying the one or more drug.

In yet other embodiments herein, the lipid bilayers of the invention (e.g., a modified and/or chimeric lipid bilayer), comprises micro-arrays for identifying the effect or efficacy of one or more putative therapeutic or preventative drug on an organism. With such micro-arrays the one or more refunctionalization component binds to, or otherwise indicates, the effect or efficacy of the putative drug. The refunctionalization component can optionally comprise a moiety from the organism that is capable of interacting with one or more infectious agent or one or more product of such infectious agent. Additionally, the lipid bilayer of the micro-arrays can be structured wherein the one or more putative drug binds to or alters the one or more infectious agent, or wherein the one or more putative drug binds to or alters the moiety of the organism. Furthermore, the invention optionally comprises a kit for identifying the effect or efficacy of one or more therapeutic or preventative drug on an organism. The kits comprise such lipid bilayer micro-arrays and one or more of a container for containing the lipid bilayer, packaging material, or instructions for identifying the effect or efficacy of the one or more drug.

These and other objects and features of the invention will become more fully apparent when the following detailed description is read in conjunction with the accompanying figures and claims.

BRIEF DESCRIPTION OF THE DRAWINGS

The patent or application file contains at least one drawing executed in color. Copies of this patent or patent application with color drawing(s) will be provided by the Patent and Trademark Office upon request and payment of the necessary fee.

DETAILED DESCRIPTION

Figure 1A:
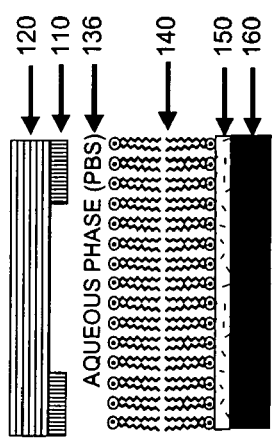
FIG. 1: Displays schematic diagrams illustrating basic patterning of a bilayer lipid membrane via UV exposure through a physical mask.

The present invention comprises methods for generating myriad micro-patterned bilayer membranes. The invention is especially designed to generate micro-patterned bilayer membranes comprising controllably localized proteins (thus creating protein arrays) or other controllably localized moieties (thus creating, e.g., polymeric arrays, arrays of non-biological catalysts, etc.). The arrays made according to the invention are optionally used in any of a variety of processes, e.g., drug screening, protein expression screening, and the like (see below). The current invention allows real-time patterning of lipid bilayer membranes and is applicable to all known substrate types (e.g., glass, silicon, polymer, gold, mica, etc.) when lipid bilayers are supported on such.

In typical embodiments herein, a physical mask is placed over a bilayer membrane which is subsequently exposed to ozone generating UV light. Pattern(s) on or in the physical mask selectively regulate which areas of the membrane below are exposed to the UV light. The areas of the membrane exposed to the UV light (i.e., those areas not blocked by the mask) are struck by the light (typically in the 184–257 nm range) with an ensuing production of ozone, thus, effectively removing the lipids (and any proteins) in those areas. Such "emptied" areas created by the UV stabilize following slight lateral expansion (and optionally self-sealing of the lipid bilayer membrane through a membrane-water interface via hydrophilic effects), thus creating a micro-patterned bilayer membrane. Thus, in some embodiments of the invention a patterned bilayer membrane or patterned membrane is created which is made up of a primary bilayer membrane background that has a "pattern" of emptied areas or holes within it. Furthermore, as explained below, the voids can be refilled by, e.g., targeted rupture of secondary lipid vesicles which then establish contiguity with the existing membrane, thereby providing a synthetic means for probing 2D reaction-diffusion processes, manipulating membrane compositions, and creating functional microdomains in well-defined patterns. The approach is generally compatible with solid-state lithographic methods developed for dry-state DNA and peptide arrays, but is applicable for the aqueous phase and fluid bilayers. It will be appreciated that the current invention uses deep UV light to directly pattern bilayers. Unlike other previous methodology, the current invention does not involve exogenous materials or chemical modification of lipids in order to create patterning of the bilayers herein. The current method relies instead on highly localized photochemical degradation in the UV exposed areas. See below. The patterning herein is direct etching of lipids that are exposed to the deep UV. Such etching provides a means to puncture holes in bilayers and to create large area patterns.

In some embodiments of the invention, such patterned or micro-patterned bilayer membranes are refunctionalization (i.e., the emptied holes are refilled or backfilled) to introduce, e.g., additional bilayer membranes, proteins, non-biological moieties, etc. (or combinations thereof). The micro-patterned lipid bilayer membranes created through the methods herein are also features of the invention. Typically, when refunctionalization is done with a bilayer or membrane, etc., the resulting membrane herein is termed a "modified membrane" or "modified bilayer," etc. As will be explained in greater detail below, such modified membranes can, depending upon the refunctionalization bilayer used, retain the refunctionalization bilayer as discrete regions within the previously emptied holes in the primary lipid membrane. In yet other embodiments, such secondary or refunctionalization bilayer will diffuse into and with the primary background bilayer. Such diffusion can result in a homogenous spread of the prior discrete secondary bilayers into the general background bilayer, depending upon diffusion coefficients, etc. In typical embodiments herein, when a patterned bilayer is refunctionalized with a non-bilayer material, also known as a secondary material, (e.g., a bead, a free protein, etc.), such resulting refunctionalized membrane is termed a chimeric membrane or a chimeric bilayer or the like.

As will be appreciated, and as described further below, the methods of the invention are easily applicable to a wide range of planar and non-planar bilayer configurations (e.g., bilayer beads or fibers, cells, liposomes, hybrid and tethered bilayers, bilayers supported on a host of inorganic substrates, etc.). Also, as will be appreciated, the present invention presents the benefits of simple steps (sometimes a single step) in patterning and optional refunctionalization of membranes and can create patterning over a large area of a membrane (e.g., pattern features of 5–500 micron dimensions spread over a 25 by 25 inch membrane on a silicon wafer, etc.). The current invention also allows construction of high-density arrays, limited only by the diffraction limit of the patterning UV light. The high throughput patterned membranes are typically stable for extended periods of time (e.g., over months) and can be constructed to allow erasable patterning in certain embodiments (e.g., patterned holes in a membrane refunctionalized with secondary membranes which merge and diffuse into/with the primary background membrane). See below. Additionally, in many typical embodiments herein it will be greatly appreciated that the patterned membranes retain a "native" cell environment which often preserves function of proteins, etc. within the patterned membrane.

Before describing the present invention in detail, it is to be understood that this invention is not limited to particular configurations, which can, of course, vary (e.g., different arrangements of masking patterns, different bilayer compositions, etc.). It is also to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a mask" or "a micro-array" optionally includes a combination of two or more such masks or micro-arrays, and the like. It will be appreciated that while the various embodiments herein are typically labeled as micro-arrays or as micro-patterned, the patterned membranes (and the methods, etc.) herein can also comprise feature sizes larger than or small than the typical "micro" range. For example, some embodiments herein comprise feature sizes of several millimeters or of several nanometers, etc.

Unless defined otherwise, all scientific and technical terms are understood to have the same meaning as commonly used in the art to which they pertain. For the purpose of the present invention, additional specific terms are defined herein. For example, as used herein, "micro-patterning" is to be understood to include, but not be limited to, creation of a lipid bilayer membrane comprising specific stable localized areas within a general background of lipid bilayer. Such background bilayer is usually described as a primary lipid bilayer herein. The stable localized areas optionally include, but again are not limited to, such things as non-lipid areas (i.e., "holes" or "emptied" areas that do not contain lipid bilayers or lipids, etc.), as well as to such holes which are refunctionalized with other constituents, e.g., lipid bilayers (e.g., stable areas of bilayers that are different as compared to the general lipid membrane background and which optionally comprise specific proteins, etc., proteins, non-biological moieties such as nanoparticles, etc.). However, a refunctionalized bilayer is typically referred to as a modified or chimeric bilayer. It will be appreciated, however, that modified/chimeric bilayers are still patterned bilayers because such patterning had to occur (to create holes) prior to refunctionalization. Such refunctionalization bilayers are usually termed secondary lipid bilayers herein. However, micro-patterning should also be understood to include creation of islands of lipid bilayer membranes comprising specific stable localized areas within a general background of emptied areas, as well as to refunctionalization of such emptied general background areas.

Correspondingly, "refunctionalization" is to be understood to indicate the addition of a substance or moiety (i.e., a refunctionalization component or refunctionalization material) to a stable localized non-lipid area (e.g., "hole" or "emptied" area) created in a micro-patterned lipid bilayer membrane. Such refunctionalization can optionally arise from the addition of, e.g., lipid bilayers (e.g., bilayers that are different or similar or identical as compared to a general lipid membrane background and which optionally comprise specific proteins), proteins, non-biological moieties, etc. Thus, refunctionalization with lipid bilayers (i.e., secondary lipid bilayers) of various sorts herein also describes creation of a "modified" lipid bilayer membrane. Correspondingly, refunctionalization with a component other than a lipid bilayer membrane (e.g., a protein, a non-biological moiety such as a metal bead, etc.) describes creation of a "chimeric" lipid bilayer membrane. It will be appreciated that some micro-patterned membranes herein, can be both modified and chimeric. Thus, for example, some areas within a membrane are optionally refunctionalized with a secondary lipid bilayer, while other areas are optionally refunctionalized with, e.g., free protein (e.g., non-membrane bound proteins) or metal nanoparticles, etc.). As will be seen below, additional terms specific to the invention are described and defined throughout.

A number of various acronyms are used herein, especially to signify various lipids, etc. Such designations are well known to those skilled in the art and include, e.g., 1,2-dimyristoyl-sn-glycero-3-phosphocholine (DMPC); 1 1-palmitoyl-2-oleoyl-sn-glycero-3-phosphocholine (POPC); Texas Red® 1,2-dihexadeconoyl-sn-glycero-3-phosphoethanolamine triethylammonium salt (TR-DHPE); N-(7-nitrobenz-2-oxa-1,3-diazol-4-yl)-1,2-dihexadecanoyl-sn-glycero-3-phospho ethanolamine, triethylammonium salt (NBD-DHPE); N-(biotinoyl)-1,2-dihexadecanoyl-sn-gylcero-3-phosphoethanolamine, triethyl ammonium salt (biotin-DHPE); Marina Blue® 1,2-dihexadicanoyl-sn-glycero-3-phosphoethanolamine (Marina Blue®-DHPE); and Fluorescein labeled streptavidin (FITC-streptavidin). Other acronyms used herein include, e.g., monosialoganglioside (Gm1); Cholera Toxin (CT), Cholera toxin B-sub units (CTB). All purified lipids and CTB are commercially available from a number of sources, e.g., Avanti Polar Lipids (Alabaster, Ala.), Molecular Probes (Eugene, Oreg.), Sigma (St. Louis, Mo.) or Matreya (Pleasant Gap, Pa.).

Great interest exists for the creation of manipulated bilayer membranes, primarily to form particular arrangements (or libraries/arrays) of proteins within or upon the bilayer membranes. Interest also exists to create arrangements of chemically/structurally distinct membrane patches within the general structure of a membrane. For example, creation of stable patches of different types of lipid bilayer areas within a lipid bilayer background can be useful in analysis of non-protein membrane binding, etc. In general, a lipid bilayer comprises two married layers or sheets of phospholipid molecules. Such structures are practically ubiquitous in living organisms and are quite well known to those of skill in the art. In typical in vitro settings, supported bilayer lipid membranes, also referred to herein as sBLMs, are representative of a broad class of molecularly engineered, bimolecular interfacial films that are composed essentially of lipids and lipid protein mixtures. Of course, it will be appreciated that the current invention is not to be limited to supported bilayer membranes, but is applicable to other types of membranes as well (e.g., tethered membranes, lipid vesicles, etc.). Tethered lipid membranes (or tethered lipid bilayers, tethered bilayers, etc.) typically comprise bilayer membranes separated from a supporting substrate by low molecular weight spacers such as peptides or polyoxyethylene (PEG) groups. Polymer-cushioned lipid bilayers (or polymer-supported lipid bilayers) are typically separated from a supporting substrate by, e.g., carbohydrate functionalized lipopolymers, or the like, and typically have a greater distance between the bilayer and the underlying substrate than do tethered bilayers. Proteo-lipidic mixtures are mixes of proteins and various lipid moieties and hybrid lipid bilayers can comprise, e.g., one lipid layer that is from one source or is naturally occurring and another layer that is from another source or is, e.g., a self-assembled monolayer. Those of skill in the art will be familiar with these and similar constructions. As will be appreciated, the lipid profiles of bilayers herein can be substantially similar, identical or different between the two layers in a bilayer. In other words, the various constituents (e.g., the specific lipid moieties, etc.) and the various concentrations of such constituents can vary or not between the two layers of the bilayer.

The ability to pattern broad classes of biological functions at spatially defined locations over a solid surface is important for the development of general material platforms for biotechnology research. Within this framework, patterning of oligonucleotides, polypeptides, and soluble proteins (see, e.g., Fodor, S. et al., *Science*, 251:67–773 (1991)) is leading to new high-throughput approaches in a host of technologies, including massively parallel genomics, biological sensor microarrays, drug screening, and proteomics research. Recently, there is a growing interest in extending this ability to pattern functions that occur at the cell membrane level (see, e.g., Bayley, H. et al., *Nature* 413:226–230 (2001) and J. T. Groves, et al., *Acc. Chem. Res.* 35:149–157 (2002)) owing to their importance in a number of key biological mechanisms (e.g., immune response, apoptosis, bacterial infections, drug screening, etc., and their relevance to a host of biomedical and biosensing technologies. See, e.g., H. Bayley, et al., *Nature* 413:226–230 (2001); Y. Fang, et al., *J. Amer. Chem. Soc.* 124:2394–2395 (2002); C. M. Rosenberger, et al., *Curr. Biol.* 10, R823–R825 (2000); A. Grakoui et. al. , *Science* 285:221–227 (1999); H. M. McConnell, et al., *Biochim. Biophys. Acta*, 864:95–106 (1996); and, J. T. Groves, et al., *Langmuir* 17:5129–5133 (2001). Because cell membranes are supramolecular assemblies and their functions closely associated with their micro-environment, a key to patterning membrane functions is the development of patterning approaches that allow integrating membrane assemblies with a solid surface at pre-defined locations, i.e., as is demonstrated in the current invention.

Supported Lipid Bilayer Membranes

Supported membranes (or supported bilayer membranes, sBLM), in this regard, offer an attractive, synthetic means to mimic selected functions of biological membranes and to integrate with a solid surface. See, e.g., Sackmann, E., *Science* 271:43–48, (1996). They represent a class of functionalized synthetic bilayers composed essentially of two apposing monolayers of phospholipids incorporating membrane receptors at controlled concentrations. They are typically formed at the solid-liquid interface when vesicular microphases of lipids and their mixtures rupture and spread spontaneously on hydrophilic surfaces. See, e.g., E. Sackmann, *Science* 271:4348 (1996). When appropriately formed, they are essentially decoupled from the local substrate chemistry through an intervening cushion layer (e.g., hydration layer of water 10–15 angstroms thickness on silica surfaces or a hydrophilic polymer layer) and exhibit two-dimensional contiguity and fluidity reminiscent of membranes of living cells. See, e.g., T. M. Bayerl, et al., *Biophys. J.*, 58:357–362 (1990); and E. Sackmann, et al., *Trends in Biotech.* 18:58–64 (2000). Further, the constituents of supported membranes can be recognized by living cells. See, e.g., A. Grakoui et. al., *Science* 285:221–227 (1999). In this regard, by appropriate selection of membrane constituents, they can mimic many functions of a real cell membrane. See, e.g., S. G. Boxer, *Curr. Opin. Chem. Biol.* 4:704–709 (2000). A key advantage of synthetic lipid membranes is the ability to tailor their structure and chemical composition for a desired function.

sBLMs, such as those capable of use with the current invention, are typically formed at the solid-liquid interface when vesicular microphases of lipids and their mixtures rupture and spread spontaneously on hydrophilic surfaces. However, successive transfers of lipidic monolayers from an air-water interface onto solid surfaces in the Langmuir-Blodgett scheme has also proved useful in construction of supported bilayer lipid membranes. As noted above, one great benefit of sBLMs is that when appropriately formed, they exhibit two dimensional contiguity and fluidity that is reminiscent of natural biological membranes. This "naturalness" of sBLMs enables the design and incorporation of a range of specific biological functions into the membrane. For example, selective incorporation of secondary membrane constituents (e.g., the types of lipids, lipid-cholesterol and lipid-protein compositions in each layer (or leaflet) of the bilayer) and/or design of specific membrane microenvironments into a sBLM can thus mimic a natural membrane structure. As a result, sBLMs have gained considerable attention, particularly in recent years, as useful models for fundamental biophysical characterization of, e.g., membrane structure, assembly, dynamics, and function. sBLMs (especially those produced/modified through use of the current invention) also hold considerable technological promise for applications such as design of biosensors and bio-compatible materials, and as suitable platforms for drug screening and selection. To construct a supported BLM, typically, a clean hydrophilic surface (or in some optional embodiments, a hydrophobic surface) or its pattern (e.g., native oxides of silicon or fused silica) is used to provide a convenient substrate for the lipid bilayer and is exposed to a solution of lipidic and proteo-lipidic vesicles. Alternatively, sBLMs can be formed by use of Langmuir trough techniques on hydrophilic or hydrophobic substrates. See, e.g., Kalb, et al. (1992) *Biochim. Biophys. Acta* 1103:307–316; Plant, (1993) *Langmuir* 9:2764–2767, and Parikh et al. (1999) *Langmuir* 15:5369–5381. However formed, sBLMs are known to consist of a lipid bilayer that is not covalently attached to a surface, but which is cushioned off of the surface by an intervening layer of interfacial water that may be 10–20 angstroms thick. See, e.g., Cremer, et al., (1999) *J. Phys. Chem.* B103:2554–2559.

Recently, there has been a considerable interest in micro-patterning of sBLMs. Bilayer membranes in general, as well as sBLMs in particular, display lateral fluidity of components (e.g., proteins) in the membrane. Because of such flow of components in membranes, the study and utilization of components in sBLMs and other bilayer membranes can oftentimes be difficult. For example, determination of ligand interaction with a number of possible membrane-bound receptors is difficult to characterize when such receptors are laterally diffusible across the membrane. Well defined compartmentalization, localization, or micro-patterning of sBLMs (and other membranes), thus, is useful for both fundamental studies and technological relevance/application (e.g., see throughout). For example, micro-patterned bilayer membranes as of the current invention are optionally utilized in, e.g., membrane-protein micro-arrays; biosensor micro-arrays; drug screening and proteomics; host-pathogen interactions; combinatorial synthesis of new materials; study/analysis of membrane structure, dynamics and assembly (e.g., involving lipid rafts); modeling of membrane mediated biophysical processes (e.g., protein-membrane and membrane-membrane interaction); and non-linear processes in diffuse-reactive systems (e.g., crystallization). As will be appreciated, such examples are to be taken as non-limiting and not describing the only utilizations of the current invention. More specifically, the development of robust micro-patterning methodologies that afford spatial control over the structure, fluidity, and function of bilayer membranes, as in the current invention, allows creation of membrane micro-arrays on different substrates, as well as the creation of protein micro-arrays and non-biological moiety micro-arrays.

General Methods of Bilayer Manipulation

Previously, patterning of sBLMs and other membrane types, e.g., to construct protein micro-arrays, has been achieved by a variety of methods that fall into two broad categories. In the first category, a number of methods have been described that rely on the use of pre-patterned substrate surfaces that present chemical and/or topological barriers to membrane continuity. Barrier materials have been deposited using general controlled deposition techniques such as photolithography, e-beam lithography, micro-contact printing, ink-jet printing, and micro-capillary injection. Typically, such barrier materials have included patterns of various metals and metal oxides, photoresists, fibrinectin and BSA proteins, photopolymerizable lipids, topochemical scratches, and, most recently, polymerized diacetylenic lipids, but simple mechanical scratches have also been used as barriers. See, e.g., Cremer et al., (1999) *J. Amer. Chem. Soc.* 121:8130–8131; Groves, et al., (1995) *Biophys. J.* 69:1972–1975; Groves, et al., (1997) *Science* 275:651–653; Nissen, et al., (2001) *Phys. Rev. Lett.* 86:1904–1907; Kung, et al., (2000) *Langmuir* 16:6773–6776; Morigaki et al., (2001) *Angew Chem. Intl. Ed.* 40:172–174; Hovis et al., (2000) *Langmuir* 16:894–897; Hovis et al., (2001) *Langmuir* 17:3400–3405; Boxer et al., (1997) *Science* 275:651–653; U.S. patent application No. 2002/0094544A1; and U.S. Pat. No. 6,228,326. Barriers on the substrate (i.e., on the support on which the bilayer membrane exists) represent areas resistant to vesicle spreading (i.e., as occurs in several types of lipid bilayer membrane formation) and bilayer formation. Thus, such physical walls prevent communication from one area or enclosure of membrane to another.

In the second category, micro-contact printing or stamping approaches have been used to provide methods for depositing membrane micro-arrays. In such methods, a micro-pattern in a preformed bilayer is created by selective removal using blotting, or selective placement using stamping methods. Thus, a stamp or die can be used to cut out portions of a lipid bilayer (similar to a cookie cutter) or a stamp or press can be used to lay down portions of a lipid bilayer (similar to a stamp pad). Other descriptions of prior methodology for creation of micro-patterned bilayer membranes as well exampled uses of such micro-patterned bilayers (which uses are optionally also performed via the methods and micro-patterns herein) is found in, e.g., Boxer, et al., (2002) *Accounts Chem. Res.* 35(3):149–157; Hovis, et al., (2001) *Langmuir* 17(11):3400–3405; Kam, et al., (2001) *J. Biomed. Mater. Res.* 55(4):487–495; Kam, et al., (2000) *J. Am. Chem. Soc.* 122(51):12901–12902; Boxer, (2000) *Curr. Opin. Chem. Biol.* 4(6):704–709; Kung, et al., (2000) *Langmuir* 16(17):6773–6776; Hovis, et al., (2000) *Langmuir* 16(3):894–897; Kung, et al., (2000) *Adv. Mater.* 12(10): 731+; Hovis, J., et al., (2000) *Biophys. J.* 1948(Pos Part 2 Jan.); van Oudenaarden, et al., (1999) *Science* 285(5430): 1046–1048; Cremer, et al., (1999) *Langmuir* 15(11):3893–3896, Cremer et al., (1999) *J. Phys. Chem. B.* 103(13):2554–2559; Groves, et al., (1998) *Langmuir* 14(12):3347–3350; Ulman, et al., (1997) *Adv. Mater.* 9(14): 1121–1123; Fang, et al., (2002) *J. Am. Chem. Soc.* 124(11): 2394–2395; Sinner, et al., (2001) *Curr. Opin. Chem. Biol.* 5(6):705–711; and Groves, et al., (2001) *Langmuir* 17(17): 5129–5133. Such references also contain listed uses for various micro-patterned arrays (e.g., as protein arrays, libraries, etc.). Such uses are also optionally performed through the methods and/or with micro-patterned arrays as are described herein. Such references are incorporated herein for all purposes by reference in their entirety to the same extent as if each individual reference, were individually indicated to be incorporated by reference for all purposes However performed, previous methods have been lacking in several aspects. For example, with construction of barriers, etc., the substrate upon which the lipid bilayer membrane exists must be compatible with the barrier and with the method used to lay down the barrier onto the substrate. Such requirement thus limits the range of possible substrates used as well as limiting the applications to membranes which have substrates. Also, prior methods depended upon the prior deposition of exogenous materials on the substrate surface and formed single patterns. Furthermore, some previous methods such as stamping (e.g., of the "die-stamp" variety) could deposit traces of the stamp onto the supporting substrate. Also, stamping methods require optimization of the physical contact and associated contact pressure, as well as the deformability of the polymer stamps. Such methods could have problems associated with achieving contact uniformity for large-area patterning. Additionally, as opposed to the current invention, such previous methods offer less malleability in terms of control of adding different lipid bilayers or proteins to specific localizations or micro-patterns within a lipid bilayer membrane. For example, previous methods have had difficulty in specifically locating different membranes and/or proteins within specific locations of the lipid bilayer membrane. Furthermore, prior methods also typically produced feature edges that were ragged. See Hovis, supra. Such raggedness was attributed to the fingering patterns that formed at the expanding front of the bilayer. The current invention does not experience such problems. Also while some alternate procedures might allow construction of small micro-patterns, e.g., wit barriers, etc., the current invention allows construction of extremely small and geometrically precise micro-patterns on lipid bilayer membranes. See, below.

Micro-patterning of Lipid Bilayer Membranes

As explained above, the need exists for a robust stable means of creating micro-patterned lipid bilayers. The current invention presents such means. In typical embodiments of the current invention, a micro-patterned lipid bilayer is constructed by exposing, through a physical mask, a lipid bilayer to an ozone producing UV light. The mask thus blocks specific regions of the UV light and prevents it from hitting certain areas of the lipid bilayer membrane. In the areas of the membrane that are exposed to the UV, the light causes the removal of the lipid bilayer at that location, along with any proteins in that area. See, e.g., FIG. 1 for a schematic illustration of this concept. As can be seen in FIG. 1a, a physical mask comprising UV opaque areas, 110, e.g., of chrome, and UV transparent area, 120, e.g., of quartz are placed between a UV light source and a bilayer membrane, 140, to be patterned. The UV mask and the membrane are typically separated by an aqueous layer, 130, which typically comprises a buffer appropriate for the particular membrane, etc. such as PBS. Also, typical membranes are supported lipid bilayer membranes, see below, and rest upon a hydration layer, 150, and a substrate, 160, e.g., composed of silica, etc. UV light is directed through the transparent areas of the mask as represented by the downward facing arrows in 1b. The UV thus contacts lipid bilayer membrane, 140, on substrate, 160. FIG. 1c illustrates resulting hole/emptied area, 170, in the lipid bilayer membrane. The result of such masking/exposure is a lipid bilayer comprising stable empty areas (i.e., areas which do not substantially change in shape or size over time) that are localized (i.e., which are controllably placed) and wherein the lipids and any proteins in those areas have been removed, i.e., thus producing stable "holes" or "emptied" areas within the lipid bilayer membrane.

Figure 1B:
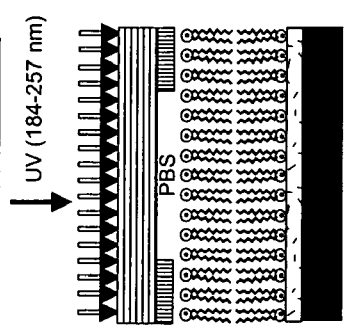
Figure 1C:
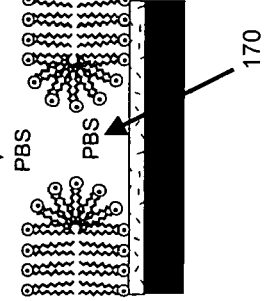

FIGS. 1a–1c show the generalized procedure for micro-patterning of a lipid bilayer. In a more specific sense, FIGS. 1a–c can be described as showing the preparation of a continuous supported bilayer lipid membrane (sBLM) on a hydrophilic silica surface. For example, a fluid bilayer of egg-phosphatidylcholine (egg-PC) or 1-Palmitoyl-2-Oleoyl-sn-Glycero-3-Phosphocholine (POPC) can be prepared by adapting previously published methods. See, e.g., Groves, et al., (1995) *Biophys. J.* 69:1972–1975. To enable fluorescence measurements, vesicles can be doped with appropriate concentrations of labeled lipids, e.g., 1 mol % 1,2-dihexadecanoyl-sn-glycero-3-phosphoethanolamine, triethylammonium salt (Texas Red-DHPE). Next, a lithographically produced mask, consisting of an array of 5–1000 μm wide square opaque (chrome) elements over a UV transparent quartz mask, can be brought in soft contact with the sBLM. Deep UV light in the 184–257 nm range (e.g., 184.9 and 253.7 nm), produced by low or medium pressure Hg lamps housed in a fused quartz envelope (10–20 mW cm$^{-2}$), can then be directed through the mask at the bilayer sample that is submerged in phosphate buffered saline (PBS) for ~120 minutes. Upon separation of the mask from the sample under the buffer, high-fidelity patterns of membrane bilayers comprising intact lipid patches in UV-protected areas and lipid-free regions in the UV-exposed areas can be obtained. It is to be appreciated that such specific example is not limiting upon the invention and that various aspects of the process are optionally varied.

Figures 2A, 2B:
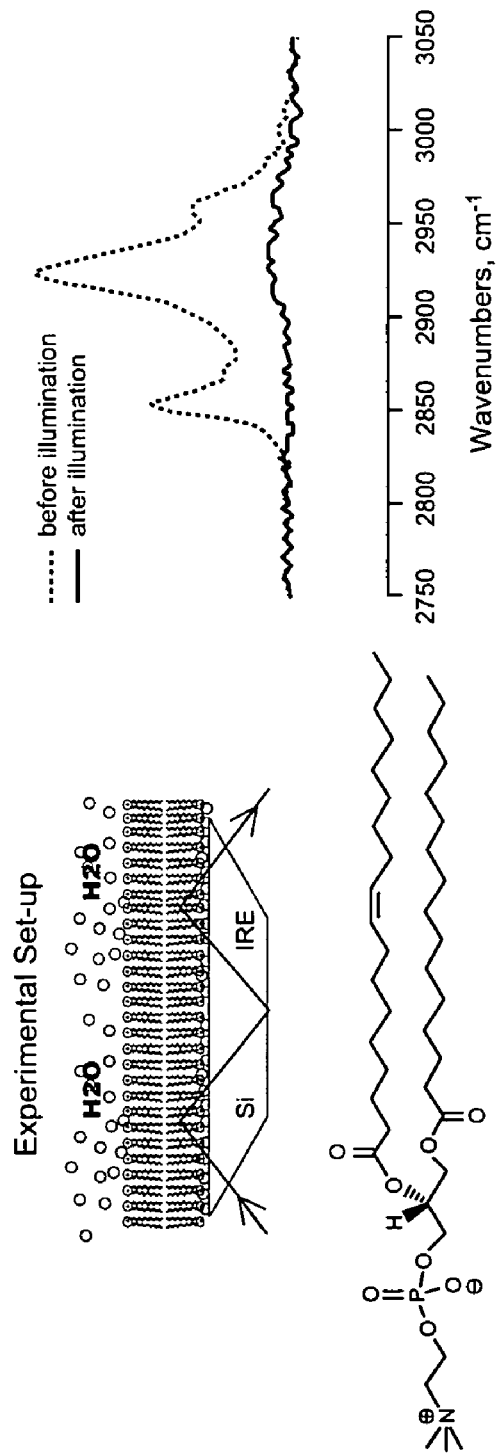
FIG. 2: Displays epifluorescence images and ATR-FTIR spectroscopy verifying that holes created in bilayer membranes by the current invention are devoid of lipids.
Figure 2C:
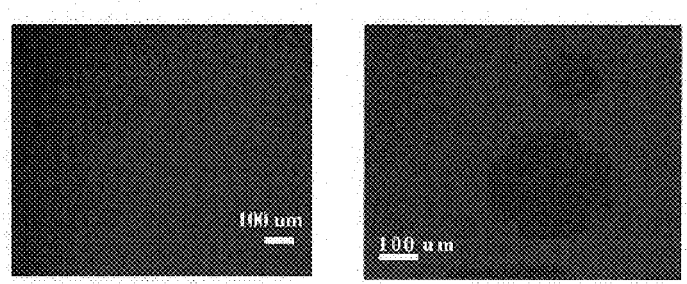
Figure 2D:
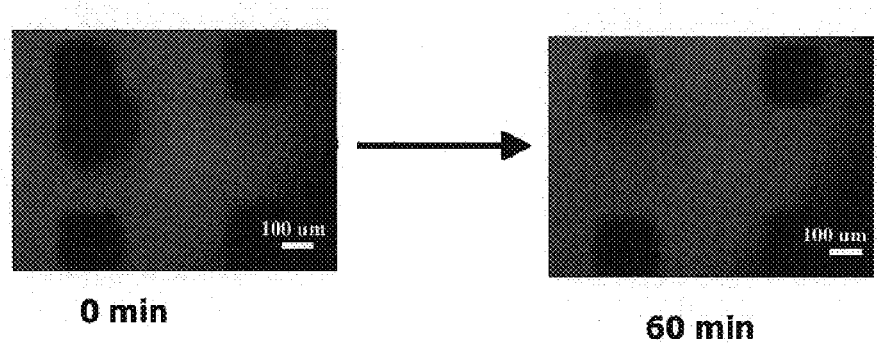

FIGS. 2a through 2d show evidence for the formation of bilayer patterns as opposed to simple bleaching of fluorescence. Optically defined transfer of a mask pattern onto a bilayer structure is evident in the epifluorescence emission seen in FIG. 2c. The data shows a high-contrast fluorescent pattern that reveals dark square regions, indicating regions devoid of fluorescence emission (i.e., corresponding to where UV illumination occurred on the membrane), separated by bright fluorescent background areas (i.e., corresponding to the protected areas of the sample surface), where the bilayer remained intact. A comparison of the attenuated total reflection Fourier transform infrared microscopy spectra, ATR-FTIR, (FIG. 2b) in the dark and bright fluorescent regions reveals the absence and the presence of the methylene C-H stretching mode absorptions (~2852 and ~2923 $cm^{-1}$) or alternatively/optionally in the acyl-chain vibrational mode regions (2750–3050 $cm^{-1}$), confirming that the dark regions correspond not to photobleached fluorophores, but are actually lipid-free regions. FIG. 2a schematically illustrates the membrane on a silicon IRE (internal reflection element) for ATR-FTIR and sample lipid molecules that would be detected. Fluorescence recovery after photobleaching (FRAP) experiments (FIG. 2d) confirmed that the lipid bilayer in the UV-protected areas retained their long-range fluidity. See, also below. The void patterns were stable under aqueous buffer solutions for weeks, indicating that the bilayer did not reconfigure significantly, and that the position of the bilayer pattern on the substrate surface remained fixed and localized. Repeated patterns with feature sizes as small as 5 µm, separated by 10 µm spacing, were visualized using epifluorescence measurements covering the entire sample surface, e.g., a 6 inch silicon wafer, and were only limited by the size of the mask or the substrate itself. The limiting patternable sizes and densities are thought to be bound only by the diffraction limit of light. Typically the sizes and shapes of the lipid-patterns were comparable replicas of that of the mask-pattern with slight, but consistent, rounding-off at the edges. Using this approach, patterns both of voids and isolated membrane islands are achievable. See below for further examples.

In various embodiments herein, several parameters can be manipulated in the production of patterned bilayer membranes. For example, the distance between the sample and the UV lamp and/or between the sample and the mask and/or between the mask and the lamp, etc. can all optionally be varied. Additionally, the UV power used and use of UV chromophores that promote photodegradation embedded in the membranes to be patterned can be manipulated. Buffer medium and temperature under which patterning is carried out can also be changed in the various embodiments herein. For example, while in many embodiments the UV mask is brought into soft contact with the bilayer to be patterned, in other embodiments the mask can be held slightly away from the bilayer. Also by reducing the sample-lamp distance patterning of bilayers can be achieved in, e.g., 10–15 minutes (as opposed to, e.g., 15–30 minutes when the distance is greater, etc.), depending on the lipid type. It will be appreciated that specific recitation of such parameters herein should not be taken as limiting unless stated to be so.

The current invention comprises myriad embodiments of controllably patterned lipid bilayers that comprise multiple lipid-free areas within a lipid bilayer membrane (i.e., at least two stable lipid-free areas within a lipid bilayer membrane, thus, forming a micro-pattern). Such embodiments also can optionally include, e.g., supported lipid bilayers, tethered lipid bilayers, polymer-cushioned lipid bilayers, lipid bilayers comprising proteins in a proteo-lipidic mixtures, and hybrid lipid bilayers comprising an outer lipid layer and an inner self-assembled monolayer. In the patterned bilayers of the invention, the lipid-free areas are not separated from the lipid bilayer by any physical barrier such as a metal/ink/polymer/etc. wall or deposit left either intentionally or unintentionally, e.g., as a result of stamp patterning, etc. between the lipid-free and non-lipid-free areas. Furthermore, the invention comprises such patterned bilayers that are refunctionalized. In other words, the empty hole areas in the patterned bilayers contain a refunctionalization component (e.g., other bilayers, proteins, non-biological components, etc.). Further elaboration/description of the bilayers of the invention are described herein.

Lipid Bilayer Compositions

The embodiments of the current invention are applicable to all lipid bilayer types, as well as optionally to other lipid membrane conformations, such as monolayers (e.g., including those wherein a single lipid layer or leaflet is bound to a substrate, or is bound to a substrate via another molecule or layer of molecules, etc.), trilayers, "stacks" of lipid bilayers such as occur by placing multiple lipid bilayers on top of one another, etc. As can be seen in FIG. 1a, and as is well known to those of skill in the art, lipid bilayers commonly comprise two sheets of phospholipid molecules which can optionally comprise diverse proteins within and/or upon the bilayer. Direct micro-patterning as described herein is optionally performed upon any number of lipid bilayer types. For example, micro-patterning (and refunctionalization, see below) is optionally done with supported lipid bilayer membranes as well as with tethered bilayer membranes, hybrid membranes (e.g., those wherein the inner leaflet of the membrane is covalently attached to a supporting surface), non-supported bilayer membranes (e.g., "free-standing" lipid bilayer architectures which are not supported by a substrate such as a silicon/glass material, etc.), membranes of cells, liposome membranes, polymer-cushioned lipid bilayers, etc.

It will be appreciated that the methods herein are also applicable to non-planar as well as planar membrane layers. For example, as used in the examples and illustrations herein, the lipid bilayer membranes are typically planar or substantially planar in nature. However, non-planar bilayers such as cell surfaces, lipid bilayer coated beads, vesicles, liposomes, etc. are optionally micro-patterned through use of the methods herein. Such non-planar bilayers are optionally micro-patterned through use of a corresponding non-planar mask (e.g., the mask is curved to mimic the surface of the bilayer) or even with a planar mask (e.g., while the mask is planar, the lipid surface is not, and the UV allowed through the mask strikes the non-planar surface similar to how it would a planar surface).

As described previously, the techniques of the invention herein are useful for all known lipid membrane types and to all known membrane mimics. Typical lipid bilayers that are used herein commonly comprise two opposed layers of lipid molecules (see above). However, other bilayers capable of use of the current invention also optionally include any other membrane-forming amphiphilic molecule (e.g., some proteins and non-lipids).

Common lipid moieties in typical bilayers such as are utilized in the current invention comprise long chain carboxylic acids (e.g., glycerides) which are esterified with fatty acid chains and a charged/polar group (e.g., a phosphate-ester). Common fatty acid chains involved in such lipids can include, e.g., acyl chains. The charged/polar head group is often a phosphate group (thus forming a phospholipid). However, the current invention is equally applicable to other configurations/components (both natural and synthetic) of lipid moieties in bilayers. For example, phosphatidylinositol, phosphatidylcholine, phosphatidylethanolamine, phosphatidic acid, phosphatidylglycerol, phosphatidylserine, sphingomyelin, etc. Bilayers comprising other common additional components (e.g., cholesterol, sphingolipids, gangliosides, membrane proteins (such as G-protein coupled receptors, ion channel proteins, proton pump proteins, glycoproteins, etc.), glycolipids, etc.) are also equally present in membranes used/constructed in the current invention. Those of skill in the art will be quite familiar with various types and components of lipid bilayers.

Figure 3:
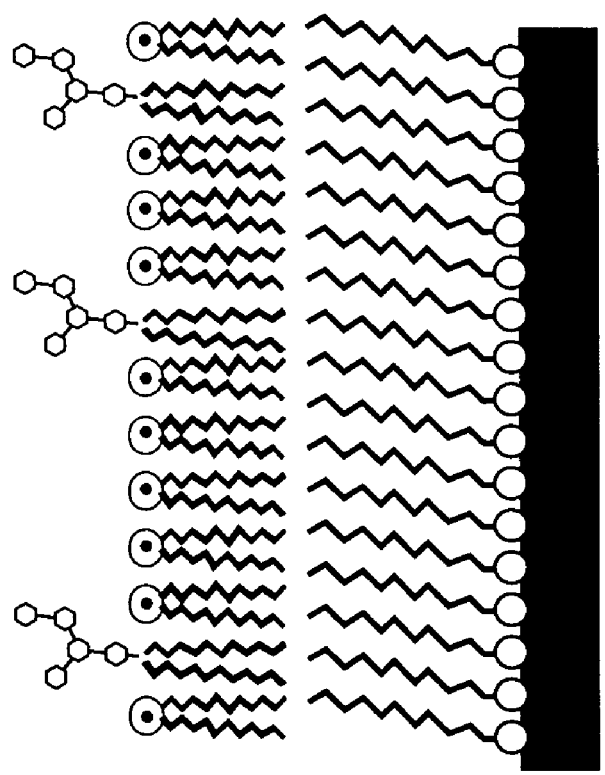
FIG. 3: Displays a schematic diagram illustrating an exemplary hybrid bilayer membrane capable of micro-patterning through use of the current invention.

The bilayers used with the invention herein are optionally derived or isolated from one or more natural source (e.g., vesicles, cells, etc.) and/or are synthetically constructed (e.g., constructed liposomes, etc.). Such isolated and/or synthetically derived components are optionally processed into, e.g., vesicles or liposomes and interfacial monolayers at an air-water interface. Such microphases are optional precursors to construction of lipid bilayers at solid surfaces using well-known methods of vesicle spreading and Langmuir-Blodgett transfers. Thus, the bilayers optionally comprise, e.g., vesicles (both in whole or in part), liposomes, monolayer membranes, lipid bilayer membranes (e.g., isolated from a cell or constructed artificially, etc.), etc. The bilayers optionally comprise any number of proteins as well. For example, typical naturally derived membranes can comprise various receptor proteins, etc. The lipid bilayers can also optionally be comprised of mixed parentage, e.g., one layer derived naturally or comprising naturally occurring molecules and the other layer synthetically created or comprising synthetically occurring molecules. For example, FIG. 3 illustrates a hybrid bilayer membrane optionally used with the current invention. In FIG. 3, inner leaflet, 300, is a covalently tethered alkylsilane monolayer, while outer leaflet, 310, is a phospholipid membrane.

UV Masking

In typical embodiments, the physical masks used to create the micro-patterned bilayers (i.e., the masks used to selectively block UV light) comprise any useful combination of UV opaque and UV transparent material(s) capable of manipulation into patterns of appropriate size and complexity. Thus, the choice of material for the mask depends upon, e.g., the specific pattern to be constructed (e.g., extremely fine openings needed, medium sized openings needed, etc.), the number of times the mask is to be used, the conditions under which the mask is to be used (e.g., the UV wavelengths, buffer conditions), etc. Typical masks can comprise a UV opaque pattern deposited upon, constructed within, or cut out of, a UV transparent base. For example, chrome patterns (UV opaque) are optionally fabricated upon a quartz template (UV transparent). Additionally, masks composed of silicon or silicon derivatives (typically UV opaque) can optionally be pierced with patterned openings to form UV transparent areas. Construction of precise nanoscale and microscale patterns upon various templates is well known to those skilled in the art and is commonly available in, e.g., computer industry applications, microfluidic technology applications, nanotechnology applications, etc. The patterns themselves are optionally produced through lithography, ablation, etching, printing (e.g., ink jet printing, laser printing, etc.), laser patterning, etc. Again, any commonly available components and methodology involving UV opaqueness/transparency and finely controllable patterning is optionally used to construct UV patterning masks used in the current invention. Specific mention of any particular methodology for UV mask construction should therefore not be taken as limiting unless specifically stated.

Figure 4A:
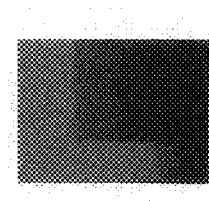
FIG. 4: Displays fluorescent images of a range of sizes and shapes of patterned holes/emptied areas in bilayer membranes corresponding to a range of sizes and shapes of UV transparent areas in the masks used.
Figure 5:
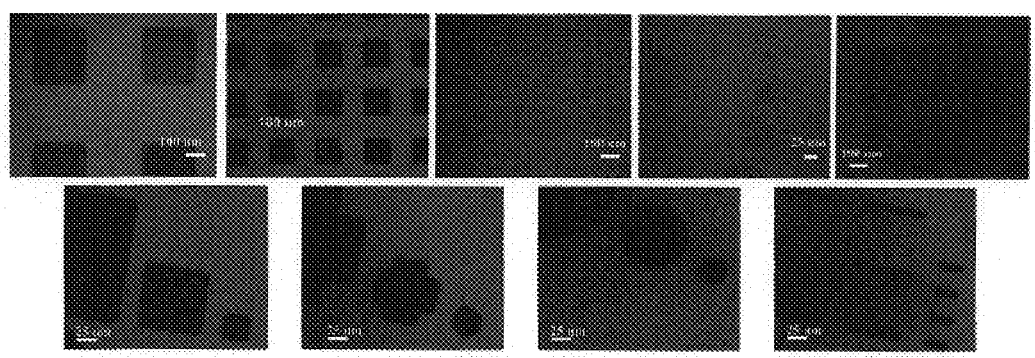
FIG. 5: Displays fluorescent images of a range of sizes and shapes of patterned holes/emptied areas in bilayer membranes corresponding to a range of sizes and shapes of UV transparent areas in the masks used.
Figure 6:
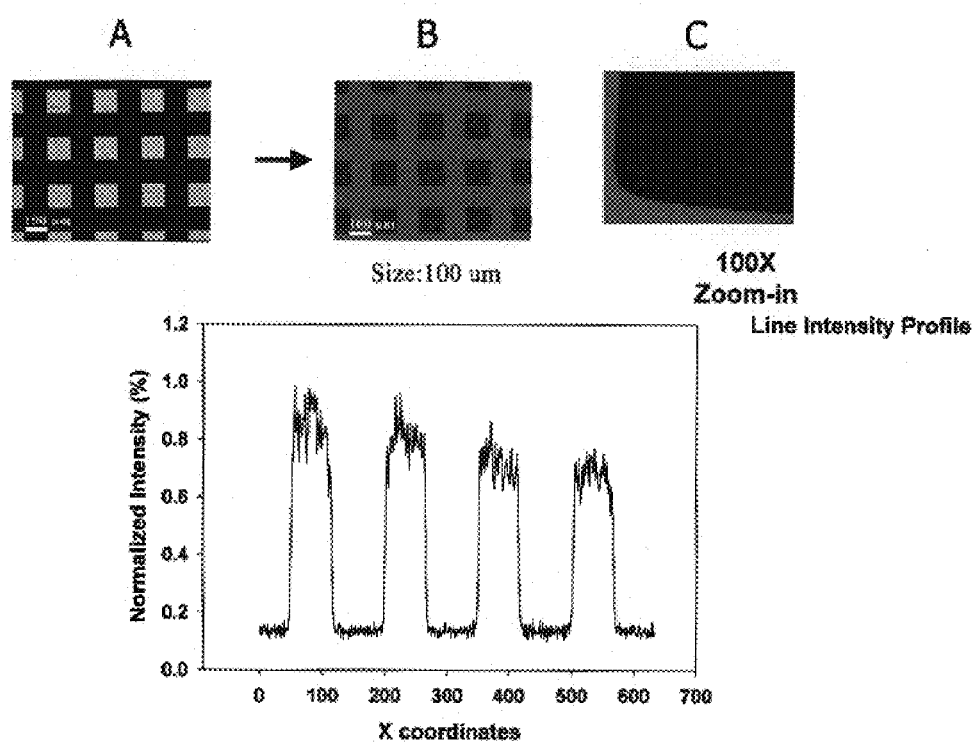
FIG. 6: Displays fluorescent images of the efficient transfer of a pattern from a mask to a bilayer and "rounding off" of pattern corners.

The UV transparent areas in the physical masks used herein are optionally of a wide range of sizes, thus producing a corresponding wide range of micro-patterned holes/emptied areas on a bilayer membrane. For example, FIG. 4a illustrates micro-patterning features of various sizes, e.g., 1000 µm, 500 µm, 250 µm, and 100 µm created by use of the current invention. However, the size and shape of the micro-patterning on a UV mask and thus the resulting micro-patterning on a lipid bilayer membrane optionally comprises a wide range of sizes. For example, FIG. 5 displays a number of possible patterning shapes, sizes, densities, and distributions that can conveniently be controlled through use of appropriate UV masks. FIG. 6 illustrates the efficient transfer of a UV mask pattern to an underlying membrane. As can be seen, the first panel in 6 shows a bright field image of a number of 100 µm square features on a quartz/chrome mask. In the panel, the white squares are quartz regions and the black regions are chrome. The second panel in 6 shows the corresponding patterned lipid bilayer which replicates the pattern features transferred from the mask. The membrane in the figure comprised 1% TR-DHPE and 99% POPC. The third panel in FIG. 6 shows a 100× magnification of the hole features in the prior panels in order to show the sharp boundary between the membrane and emptied areas and the rounding-off of the emptied areas at their corners. The fourth panel in the figure shows a comparison of the fluorescence intensity between emptied areas of the patterned membrane and non-emptied areas. In other embodiments the mask UV-transparent areas (and thus the micro-patterned holes/emptied areas) range in length and/or width from about 2 millimeters to about 0.1 micrometers. In different embodiments, the UV-transparent areas can comprise one or more dimension (e.g., length and/or width) of from about 5 millimeters to about 0.1 micrometers or less, or optionally from about 2 millimeters to about 0.5 micrometers or less; from about 1 millimeter to about 1 micrometer or less; from about 500 micrometers to about 5 micrometers or less; from about 250 micrometers to about 10 micrometers or less; from about 100 micrometers to about 15 micrometers or less; or from about 75 micrometers to about 25 micrometers or less. In other embodiments the size of such UV-transparent areas comprises around 200–300 nanometers. Additionally, the shape of such UV-transparent areas (and, again, of the resulting micro-patterning on a lipid bilayer) can also be of any desirable conformation which fits within the dimensions of a UV-opaque mask. For example, some embodiments herein comprise UV-transparent areas comprising, e.g., squares, lines, circles, grids, letters, etc. Again, see FIG. 5. The UV-masks themselves are also optionally of variable size. Typically, the masks are of a size to match the lipid bilayer to be patterned (i.e., they are of the same size). The size of common lipid bilayers to be patterned is also variable and can range e.g., from about 5 centimeters by 5 centimeters or 2.5 centimeters by 7.5 centimeters or the like. Additionally, the size of UV-masks used herein can also vary depending not only upon the size of the membrane to be patterned, but also upon, e.g., the number and size of the designs to be patterned onto the membrane, etc. The size of the masks (and also the size of the micro-patterned membranes created) can range down to, e.g., the size of two of the smallest possible openings (e.g., UV-transparent areas) in a mask surrounded by UV-opaque areas. For a non-limiting example, the width of a mask can optionally comprise the distance of two 0.01 micrometer UV-transparent areas and three 0.01 UV-opaque areas (i.e., one on each side of the transparent areas and one in-between them), or the like. The choice of material used to construct the mask and the choice of method used to produce the UV-transparent UV-opaque areas, thus influences the size dimensions of the mask produced.

It will also be appreciated that, in some different embodiments, the patterned UV-opaque mask can comprise any number and/or conformation/arrangement of UV-transparent areas which fits within the dimensions of the UV-opaque mask. Thus, in some embodiments, the density of micro-patterned areas (e.g., emptied areas within a bilayer or islands of bilayer surrounded by emptied areas) optionally comprises, e.g., from about 144 micro-patterned areas to about 2200 or more micropatterned areas per square centimeter. A factor in determining density of micro-patterning (both on a UV mask and upon a lipid bilayer) includes the distance between the UV-transparent areas in the UV-opaque masks. Such interstitial distances can optionally comprise a range of possible distances (again, varying upon, e.g., the number and sizes of the UV-transparent areas and the size of the UV-opaque mask). For example, in some embodiments herein, the distance between two or more UV-transparent areas comprises from about 2 micrometers to about 3 millimeters or more. Also, as explained in more detail below, micro-patterning of a lipid bilayer through transparent areas of a UV mask can optionally create "holes" in a lipid bilayer background or "islands" of lipid bilayer membrane in an emptied background. In such instances, the concepts of distance between features on the patterned membrane are equally applicable.

Figure 4B:
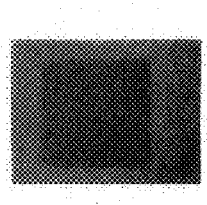
Figure 4C:
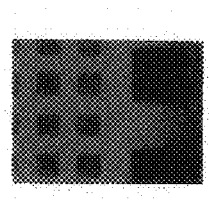

An example of the capability of the current invention to produce micro-patterning of varying size ranges is seen in FIG. 4. The micro-patterning in FIG. 4 was done by UV/ozone exposure under water using a 1% TR-DHPE/egg PC bilayer (see below) on an OTS covered glass cover-slip. OTS, or octadecyl tricholorosilane, comprises a popular long-chain self-assembled monolayer which tethers to glass and renders the resulting surface highly hydrophobic. As can be seen in FIG. 4, emptied areas in a lipid bilayer were produced through exposure of the lipid bilayer to UV through a patterned mask. The sizes of the resulting emptied areas ranged from 1000 μm×1000 μm to 500 um×500 μm, 250 μm×250 μm, and 100 μm×100 μm. Of course, such demonstrated mask sizes/patterning sizes are not to be considered limiting. In fact, the UV-transparent areas in the physical mask can optionally be sized down to a diameter corresponding to the wavelength of the UV light being used.

In typical embodiments herein, lipid bilayers, etc. are patterned through use of UV light to create holes/emptied areas within the membrane. It will be appreciated that in some embodiments herein, the UV-opaque masks are optionally utilized to create patterns comprising spatially stable "island(s)" of lipid bilayer membranes. In other words, while in some typical embodiments, the resulting pattern comprises a number of emptied holes arrayed in a lipid bilayer, in other typical embodiments, the resulting micro-pattern comprises a number of distinct isolated lipid bilayer membranes surrounded by emptied areas. The UV-opaque mask used to construct such "island" arrays, thus, is a reverse or negative image of the type of UV-opaque mask used to construct the "hole" arrays (e.g., the mask is optionally a series of UV-opaque squares surrounded by UV-transparent grids, thus, resulting in bilayer "islands" surrounded by emptied grid areas as opposed to the mask optionally comprising a series of UV-transparent squares surrounded by UV-opaque grids, thus, resulting in emptied "holes" surrounded by lipid bilayer grid areas). In the present invention blanket UV illumination was used in conjunction with a patterned mask. However, other embodiments can optionally comprise UV patterning of bilayers by using focused deep UV radiation (i.e., without an intervening mask), patterned deep UV radiation (i.e., without an intervening mask), structured illumination, etc. The UV illumination in the embodiments herein typically is directed from above the bilayer (e.g., typically 5–10 mm above the sample) and is typically in the air. Alternatively, the UV illumination can be from beneath the bilayer (e.g., typically from about a similar distance and in the air). Additionally, as explained elsewhere herein, the period of illumination during which the bilayer is exposed to the deep UV light can optionally vary. Typical embodiments herein can produce patterning within about 10 minutes of exposure or, typically within 15 minutes of exposure (independent of lipid type and fluorophore used).

In the creation of the patterned bilayers herein, as explained throughout, the methods herein can optionally be used to subject a single bilayer sample to multiple rounds or cycles of patterning and refunctionalization (i.e., backfilling) to create an array of refunctionalized structures where the refunctionalization in each round is different from the previous round. Thus, large microarrays that display different membrane (and/or different receptors, etc.) in different optically defined regions (i.e., refunctionalization areas) can be created through the current invention. The amount of time that bilayers are exposed to UV light in order to create the empty voids in the patterning process herein can depend upon the particular illumination geometry of the creation. In some embodiments, a 10 minute exposure time is sufficient to create voids within bilayers by using a medium pressure Hg lamp, a chrome/quartz mask (1 mm thick) when the sample surface is 5 mm from the UV lamp. Holes as little as 1 micrometer and separated by 2 um have been shown to be stable in the current invention. Again, the smallest possible feature size is thought to be dependent upon, e.g., the diffusivity of the oxidants and the diffraction limit of light.

Mechanisms of Bilayer Patterning

Without being necessarily bound to a particular theory or mechanism, in the micro-patterning process the first step typically comprises photochemical activation of the lipid molecules in the areas of the membrane exposed to the UV light. It is well established that the mechanism by which UV/ozone destroys the organic molecules in such areas involves a complex set of photosensitized oxidation processes. The UV patterning herein is thought to be somewhat analogous to a recently proposed bactericidal pathway in which holes in the bacterial cell wall are produced locally at the sites of antigen-antibody union by ozone and singlet molecular oxygen. See, e.g., Wentworth et al., (2003) *Science* 298:2195–2199. The simplest description of the overall process involved in the UV destruction of specific membrane areas comprises three overlapping photo-induced chemical reactions.

Figure 7:
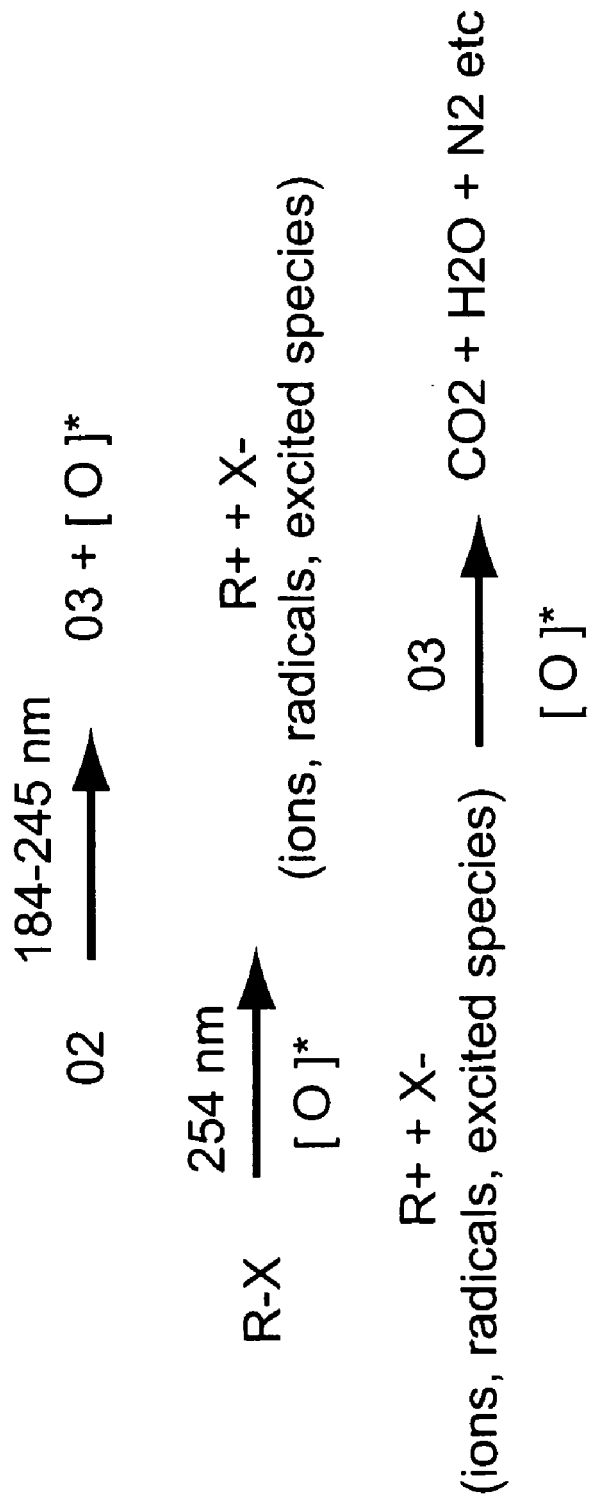
FIG. 7: Displays a schematic illustration of mechanisms in micro patterning.

First, spatially-confined photochemical degradation of lipid molecules in the UV-exposed areas is achieved through use UV light (e.g., from a low to medium-pressure Hg lamp) with a wavelength below 245.4 nm (optimally at $\lambda$=184.9 nm) which facilitates the dissociation of oxygen (from the, e.g., aqueous ambient phase in which the lipid bilayers are typically situated) to produce ozone and atomic oxygen both of which are strong oxidizing agents. Simultaneous to such dissociation, the 253.7 nm wavelength emitted by the same lamp (or, in some embodiments, by another one or more simultaneously used lamp) excites and/or dissociates the organic matrix in the thin film mesophases, optionally by ozone. Because the absorption by ozone is self-destructive, under UV light, ozone is continually being formed and destroyed. The absorption of 253.7 nm light by the organic lipids excites and/or dissociates them, thereby producing activated species, such as ions, free radicals, and excited molecules. These activated organic species are readily attacked by the atomic oxygen and ozone (synergistically) to form simpler volatile molecules, such as $CO_2$, $CO$, $H_2O$, $N_2$, etc. The simple volatile molecules escape from the surface of the membrane and dissolve into the aqueous ambient phase. Thus, in typical embodiments herein, the lipid bilayer membranes to be micro-patterned are optionally placed within appropriate aqueous solutions to allow-the proper reactions to take place. See FIG. 7 for equations illustration the reactions. Similar mechanisms are used in waste-water treatment and in cleaning semiconductor surfaces in air or vacuum. The photo-oxidation process exhibits a remarkable lateral confinement thought to be due to the short-lived nature of $^1O_2^*$ and $O_3$ and the requirement of photoexcitation of lipid molecules. Stable patterns form even when bilayers are "over" exposed to UV light for several hours, suggesting a self-limiting character of the UV photochemistry. As noted above, the process is thought to be analogous to a recently proposed role of ozone as a broadly applicable effector molecule in the immune systems. Wentworth and co-workers have suggested that short-lived ozone (and possibly other related oxidants) produced by the antibody-catalyzed water oxidation pathway at the site of antibody-antigen union punctures highly localized holes in bacterial plasma membranes, subsequently killing their antigenic targets. See Wentworth, supra. Regardless of the particular mechanism, resulting micropatterned bilayers are produced as illustrated in the nonlimiting examples herein.

The second reaction in the UV photo-activated creation of holes/emptied areas within membranes concerns the lateral confinement of such process. The photo-oxidation of the organic lipids in the process requires simultaneous presence of the UV light and the oxidative species (oxygen and ozone). As a result, any diffusion of oxidative species (e.g., oxygen or ozone) under the mask at the sample surface (i.e., at the membrane surface) does not blur the pattern definition since no UV light hits such masked areas.

The third step involves the laterally selective removal of lipidic molecules to create a high energy interface at the lipid/water interface. The fluid bilayer expansion at this edge appears to be only slight and self-limiting. The edges of the bilayer membranes around the holes/emptied areas optionally seal themselves through the spontaneous reorganization of the lipids into a hemi-micellar microphase at the substrate surface (see, e.g., FIG. 1). The laterally selective removal of lipid molecules creates an energetically unfavorable interface exposing hydrophobic lipid chains to the aqueous medium at the boundary. Relaxation of the associated line tension can occur via large-scale stretching of the remaining bilayer only if a source for additional lipids were accessible such as through suppression of undulations. See, e.g., Sandre, et al., (1999) *PNAS, USA* 19:10591–10596. It is thought that the sBLMs do not possess such accessible lipids in significant quantities required for healing such sized voids that are created herein. It appears that the borders shield the hydrophobic lipidic chains from the aqueous ambient environment through spontaneous reorganization of the lipids presumably into a closed hemi-micellar microphase.

A demonstration of micro-patterning of a bilayer membrane through use of the current invention is illustrated below. In the present illustration, optically defined patterning of a supported bilayer membrane was achieved in a single step using UV-ozone photochemistry under aqueous conditions as explained throughout. Once again, the general procedure that was used to pattern the supported bilayer membrane is schematically shown in FIG. 1. The process began with the preparation of a continuous bilayer membrane on a hydrophilic silica surface. Fluid bilayers of egg-phosphatidylcholine (Tc=° C., Avanti Polar Lipids, Alabaster, Ala.) were prepared by adopting previously published methods. To enable fluorescence measurements, vesicles were doped with an appropriate concentration of labeled lipids (e.g., TR-DHPE or BODIPY 530/550 DHPE), but other fluorescent markers could also have been used. Next, a 50–100 microliter drop of small unilamellar vesicles of the egg-phosphatidylcholine in a 150 mM phosphate saline buffer at pH 7.4–8.0 was placed on a clean culture dish. A freshly cleaned silica surface (e.g., a borosilicate cover-slip, quartz, or a silicon wafer with a native oxide over-layer) was allowed to incubate for a period of 30–45 minutes at room temperature with the vesicles. The sample surface was then rinsed with a copious amount of deionized water (at 918.0 megaohm-cm resistivity). Care was taken during the process to maintain the sample surface (i.e., of the lipid bilayer membrane to be patterned) fully submerged in an aqueous phase. The resulting bilayers were stored in pure deionized water or in a PBS buffer. The sample bilayers were characterized using fluorescence microscopy and quantitative applications of attenuated total internal reflection Fourier-transform infrared (ATR-FTIR) spectroscopy. Fluorescence recovery after photobleaching (FRAP) confirmed respectively, the formation of a uniform, continuous film, composed of a single lipid bilayer exhibiting a fluidity consistent with a lipid diffusion coefficient of about 4–6 $um^2$/second (data not shown). FRAP, a common measurement known to those of skill in the art, briefly consists of exposing a fluorescently labeled bilayer membrane to an appropriate wavelength(s) of light, thus, bleaching out the fluorescence in the exposed area (e.g., leading to a measurable non-fluorescent area of the bilayer membrane). Due to the diffusion coefficients of bilayer membranes, such bleached molecules diffuse out of the exposed area and nonbleached molecules diffuse into the exposed area, thus gradually erasing the bleached spot.

Next, a lithographically produced mask, consisting of UV-transparent features (here comprising size openings of 1 μm up to 1000 μm), was brought into direct contact with the bilayer membrane. It will be appreciated that the current invention encompasses a number of embodiments wherein the distance between the physical mask and the lipid bilayer is variable. However, in typical embodiments the UV mask is either touching the lipid membrane or, preferably, is within a few micrometers of the surface of the lipid bilayer. With increasing distance between the mask and the lipid bilayer, UV reflection and diffusion optionally "blur" the edges and parameters of the emptied areas/holes created through the invention. Of course, other embodiments include wherein the blurring effect is desired, thus, the mask and lipid bilayer are moved further apart. To prevent slippage of the mask from the sample surface in the current illustration, it was occasionally necessary to clip the mask to the sample surface using binder clips. Ozone generating UV light in the 184–257 nm range, produced by a low pressure mercury (Hg) lamp housed in a quartz envelope, was then directed through the mask at the sBLM samples submerged in the aqueous environment for 90–120 minutes. In other embodiments, the length of the time such samples are exposed to UV light optionally ranges from, e.g., from about 1 hour to 12 hours or more. Of course, in other embodiments, multiple UV sources are optionally used to produce the desired wavelengths. Additionally, the type of UV lamp utilized herein should not be construed as limiting. Thus, any UV lamp or combination of lamps, which produce the desired UV wavelengths are applicable (e.g., any, or any combination of, e.g., tungsten-halogen lamps, xenon-arc lamps, mercury lamps, excimer lasers, etc. are all equally usable). In some embodiments, the distance between a lamp and the bilayer to be patterned is to be taken into consideration. Thus, in some embodiments, the lamp(s) are placed in a soft, direct contact with the bilayers at a distance of about 10 mm from the lamp, from about 5 mm to about 15 mm from the lamp, or from about 1 mm to about 20 mm from the lamp. The process resulted in patterned bilayer membranes similar to that seen in FIG. 4.

Figure 8:
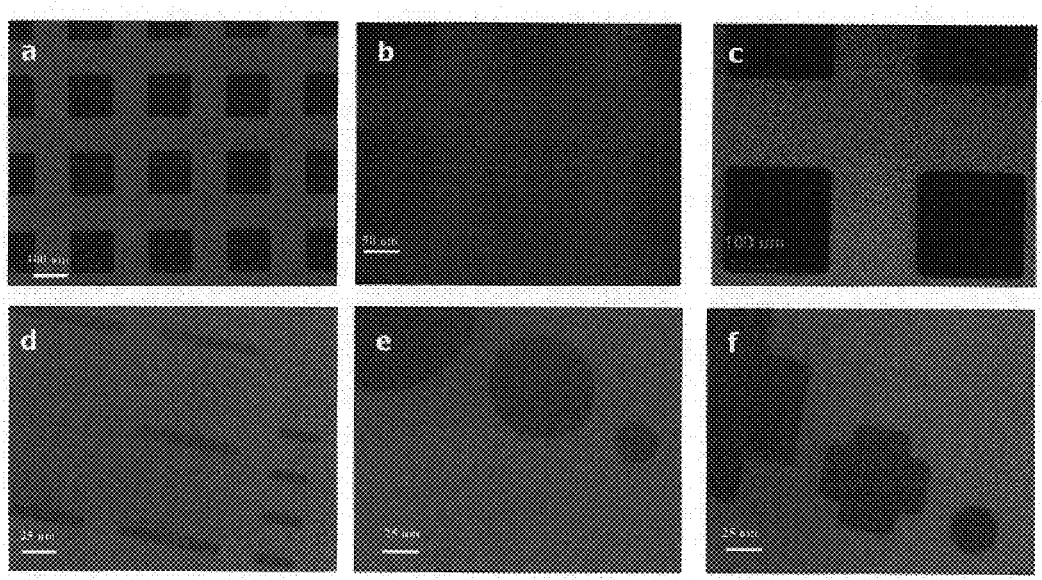
FIG. 8: Displays fluorescent images of various patterns possible in membranes and the independence of membrane patterning herein from fluorophores in the membranes and composition of the membranes.

The patterning process of membranes is independent of different fluorophores present in the membrane and of various lipid-types present in the membrane as well. For example, FIG. 8 shows patterning using various fluorophores (e.g., Texas-red, NBD, and BODIPY labeled DHPE lipids) and several phospholipids and their mixtures including DPPC, DMPC, DLPC, POPC, and egg-PC. As can be seen in FIG. 8, the pattern formation using UV illumination was independent of the nature of the fluorophores and the phase state of the lipids used. In FIG. 8, panels a and d–f are POPC membranes doped with Texas red, while panel b is DMPC doped with marina blue, and panel c is a raft bilayer membrane doped with NBD.

Figures 9A, 9B, 9C, 9D:
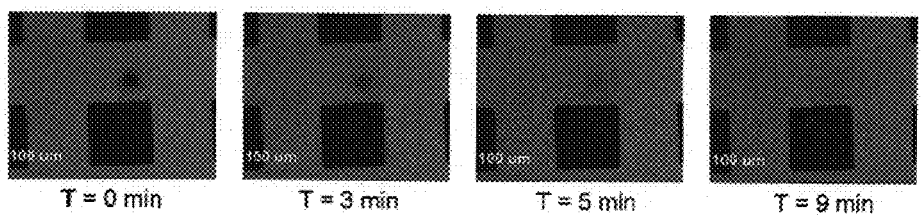
FIG. 9: Displays fluorescent images showing the fluidity of regions of a lipid bilayer membrane that are not exposed to UV light and the stability of emptied regions of a lipid bilayer membrane that are exposed to UV light.
Figure 10:
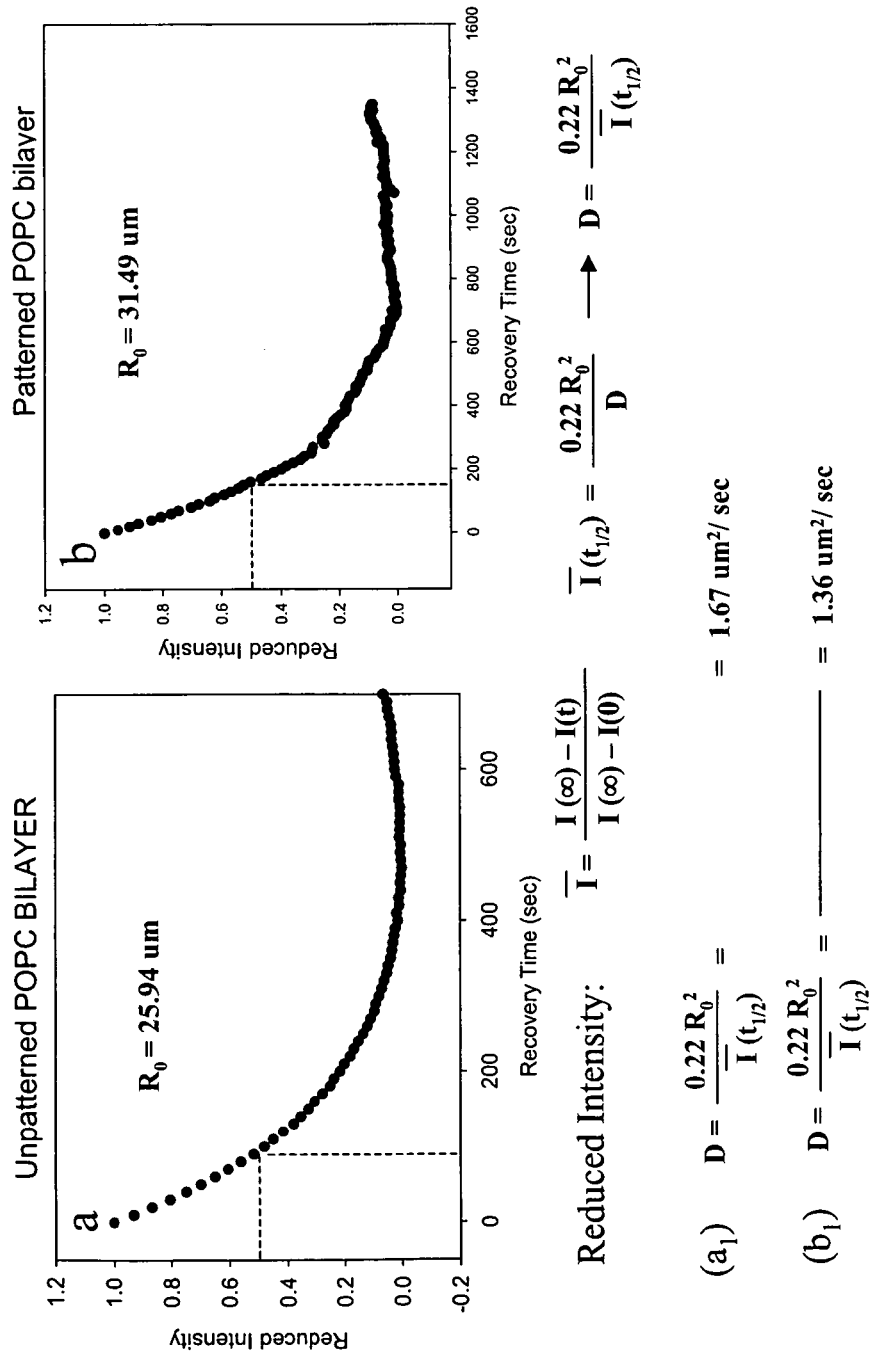
FIG. 10: Displays graphs showing the fluidity of unexposed regions of a patterned lipid bilayer membrane as compared to the fluidity of a non-patterned membrane.

Evidence for the laterally defined removal of the lipidic molecules from the bilayer membrane due to UV exposure is seen from the data shown in FIG. 9. A representative fluorescence image of the UV-ozone treated samples is shown in FIG. 9. Transfer of the mask pattern into the bilayer architecture is clearly evident in the dark square regions of approximately 100 µm dimension corresponding to 100 µm UV-transparent areas of the mask. Such dark areas indicate regions devoid of fluorescence emission (i.e., regions lacking the fluorescent lipid molecules because of degradation by the UV). ATR-FTIR microscopy measurements (see, e.g., FIG. 2b for similar measurements) confirmed that these dark regions correspond not to bleached fluorophores, but that the lipid molecules had been removed from these areas below the detection limit of the spectrophotometer. Additionally, in FIG. 9 can be seen the creation and erasure of a photobleached area (i.e., the dark circular area in FIG. 9a as opposed to the dark square areas which are formed from the UV exposure). In contrast to the square formations created through the UV exposure which are stable and clearly delineated and localized, the round photobleached area diffused out over time. This, thus highlights the stability of the UV exposure created micro-patterns as well as the integrity of the base lipid bilayer membrane after exposure to the UV. In other words, the non-exposed areas still displayed lipid diffusion within the membrane (cf., FIG. 9a and FIG. 9d where the photobleached area has largely dispersed). The graphs and equations in FIG. 10 verify that membrane fluidity of areas not exposed to UV remains unaffected by such patterning (i.e., such unexposed areas of a patterned membrane show similar diffusion coefficients, etc. as photobleached areas of membranes that are not UV patterned). In FIG. 10, a semiquantitative assessment of the mobility of fluorophores within the membranes was made using microscopy-based fluorescence photobleach recovery measurements by adapting the circular spot photobleaching method. Specifically, a circular region of the fluorescent bilayer sample, ~30–50 µm diameter, was continuously illuminated at high power at the excitation wavelength for the fluorophore through a 60× objective for ~2 minutes. Such exposure bleached a dark spot on the bilayer caused by the photoexcitation of the fluorophore followed by an irreversible chemical transformation effected by its reaction with dissolved oxygen. After this intense and extended illumination, the objective was replaced by low power observation beam and a 10× or 20× objective to record wide-field images of the fluorescence recovery in the bleached area at 10 second intervals. The recovery results from the diffusion of active fluorophore-lipids from the unbleached background into the bleached spot. It has been previously established that the shape of the recovery curve depends on the size and uniformity of the bleached spot as well as the thermal diffusion coefficient of the fluorophore in the bilayer environment. See Axelrod, et al., Biophys. Journal 1976 6:1055–1069. Consequently, the recovery curves can be used to determine an estimate for the fluorophore diffusion constant, D, a measure of the fluidity of the bilayer environment and any fraction of lipids that are immobile. Soumpasis's model (see Soumpasis, Biophy. J. 1983, 41:95–97) can be used to estimate the diffusion coefficients for the fluorophore lipids. It should be noted that since the spots used in the approach were very large (50 µm diameter) allowing diffusion during the photobleach, the estimates derived are not quantitative and reflect both the measurement inaccuracies and any sample heterogeneities over the sampled area.

Figure 11:
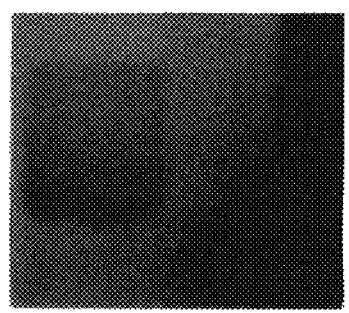
FIG. 11: Displays fluorescent images illustrating the extended stability of micro-patterns of emptied regions of a lipid bilayer membrane of the invention.
Figure 11:
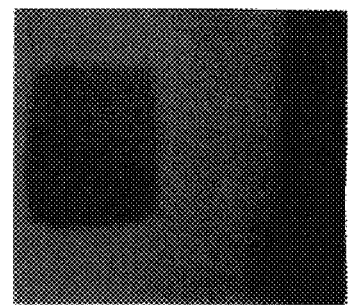

Time-lapse fluorescence images reveal that the holes created in bilayers herein do not heal and that their position on the substrate remains fixed for several days. See, e.g., FIG. 11. FIG. 11 illustrates an example of a hole/emptied area created in a lipid bilayer membrane through use of the current invention. The emptied area is clearly delineated at 1 hour and also after 96 hours, thus, showing stability of the created micro-patterning.

Thus, as can be seen from such illustration, the rapidity, reproducibility, and ease of introducing pre-defined arbitrary patterns within fluid bilayer membranes, combined with the possibilities of introducing and removing (see below) these patterns in real-time in a non-contact manner renders the UV-ozone photochemistry of the invention to be a very powerful alternative to the substrate structuring and stamping methods used previously to pattern fluid bilayers.

While typical embodiments herein utilize UV light in wavelengths of about 184 and 257 wavelengths, some embodiments of the invention comprise two and even multiphoton processes to create the required UV wavelengths at the site of patterning. Briefly, the process of multiphoton absorption processes for high spatial resolutions surpassing the diffraction limit relies on the non-linear optical properties of the material being imaged. In a typical measurement, a high-intensity beam of light, such as produced by a Ti:Sapphire or an Nd: YAG laser, is impinged on a material. By carefully selecting the pulse energy and durations, intensity threshold required for multiphoton absorptions is met in a small central core of the Gaussian beam. In this manner, apertureless imaging at high resolutions is afforded. Specifically, three and four photon absorptions using a high-intensity YAG (1064/3, 266 nm) and/or Ti:Sapphire lasers (790/3, 264 and 790/4, 197 nm) are used to carry out highly localized lipid oxidation. The success of the approach optionally depends on the ability of these multiphoton excitations to initiate and sustain photochemical lipid oxidation such as occurs using the diffuse light. Optional advantages to such method include, e.g., elimination of the need to use deep UV radiation which could possibly limit the applicability of the approach to simple in vitro systems; and use of the method to create patterns of voids (and hence secondary functions) in very high-densities and of nanometer length scales approaching and possibly below the diffraction-limit of UV light, etc.

Refunctionalization

As illustrated above, in some embodiments, the current invention comprises methods to create micro-patterning of lipid bilayer membranes wherein stable holes/emptied areas are created at specific localized regions in the lipid membrane or wherein islands of lipid bilayer surrounded by emptied areas are created, etc. However, in yet other embodiments, such created emptied areas are optionally "refunctionalized." Thus, the emptied areas created in the bilayer membrane are optionally "refilled" with desired material/components. Yet another advantage of the current invention is that such refill material optionally comprises any one of a large number of compositions and compounds. For example, in some embodiments, as illustrated in more detail below, the emptied areas can be refunctionalized with areas of lipid bilayer membranes (i.e., "secondary" membranes are refunctionalized into a "primary" membrane). Such secondary membranes used in refunctionalization can be of the same type as the general background lipid membrane (i.e., the primary membrane in which the emptied areas were created) or they can be of a different type of membrane. For example, the secondary membrane added to the emptied area can optionally comprise such differences from the background membrane as: different types of lipid molecules, different ratios of lipid molecules, different types and/or amounts of proteins within or on the membrane, different diffusion coefficients, presence/absence of polymerizable lipids, etc. In such embodiments, the refunctionalized lipid membrane area is optionally added to the general lipid membrane background (i.e., the membrane in which the emptied areas were UV created) in the form of, e.g., lipid rafts, lipid vesicles, or the like.

Lipid Rafts

Figure 12:
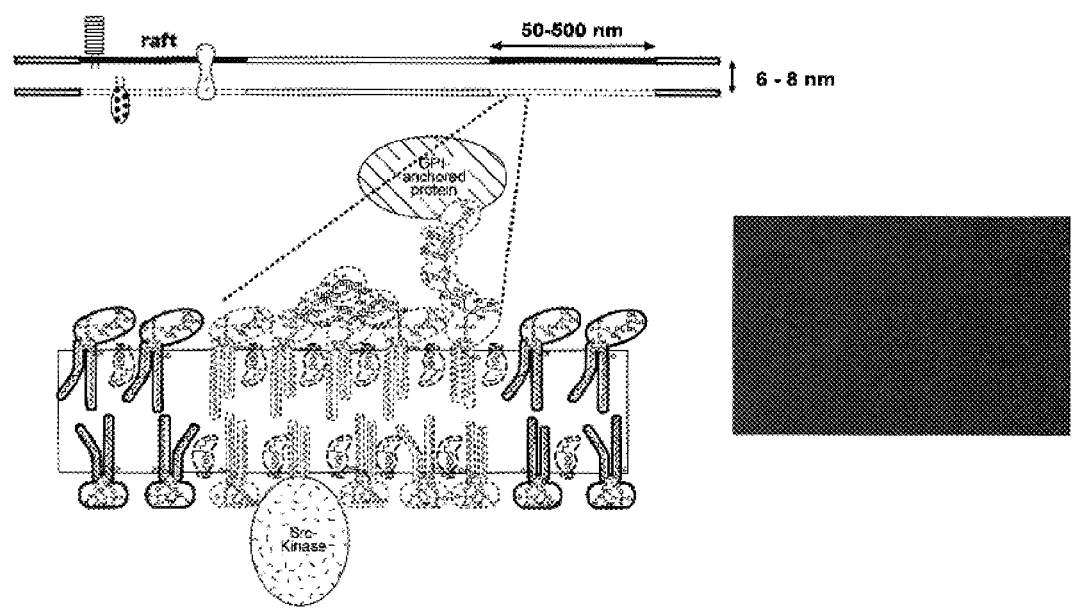
FIG. 12: Gives a schematic diagram of a typical lipid raft and a fluorescent image of refunctionalized lipid rafts within a patterned bilayer.
Figure 13:
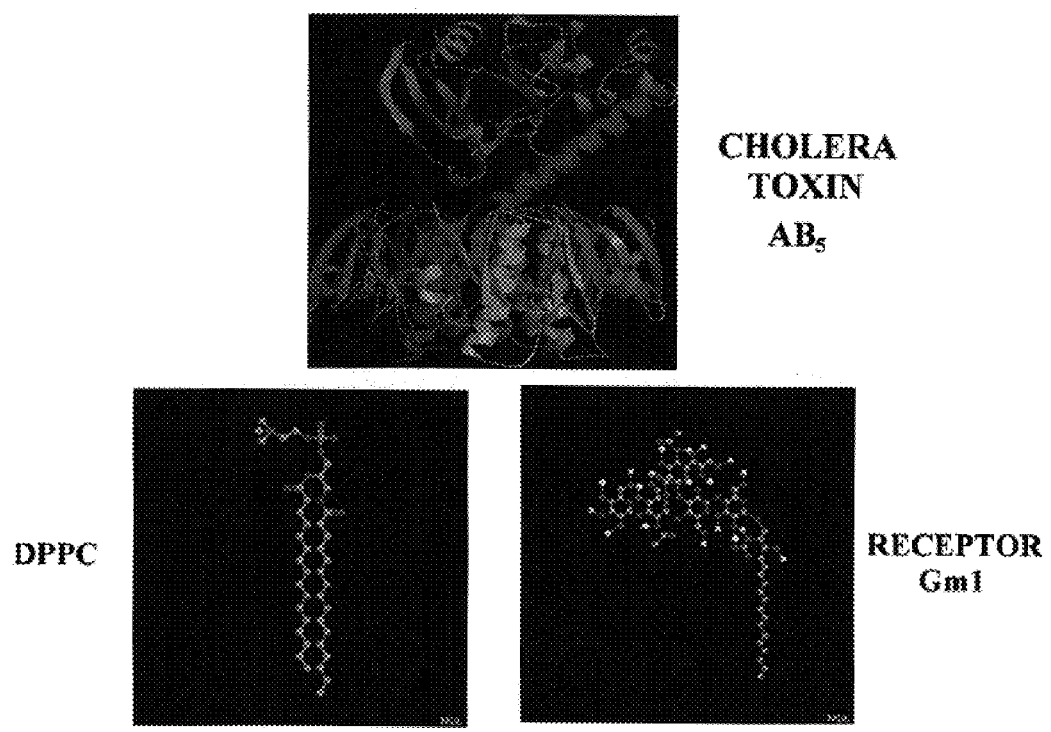
FIG. 13: Displays schematic diagrams of cholera toxin, Gm1 and DPPC.

For example, in some embodiments refunctionalization with a secondary lipid membrane (e.g., one containing specific proteins of interest to construct a protein array or the like) comprises use of one or more lipid raft. Lipid rafts are lipid micro-environments typically enriched in cholesterol and sphingolipids and typically about 50 nanometers in diameter. See, e.g., FIG. 12 which shows a schematic illustration of such and an epifluorescence image showing presence of lipid raft domains in a bilayer background (green corresponds to lipid rafts and red to the background bilayer). The schematic illustration in FIG. 12 is adapted from Simons et al., *Nature* 387:569–572 (1997). Such rafts usually comprise longer and more saturated lipid tails, and are thicker and less fluid and display slower diffusion coefficients than non-raft lipid membranes. In natural lipid bilayer membranes (and in constructed/modified/etc. membranes herein), sphingolipids, a major constituent of rafts, with their saturated acyl chains in extended configurations and large polysaccharide head-groups, allow for cholesterol to be tightly intercalated in their intermolecular free volume. As a result, the sphingolipid-cholesterol mixture phase separates from other unsaturated lipids in the membrane. Therefore, lipid raft microphases comprise a notably denser local molecular environment, and thus form distinct liquid-ordered regions (i.e., lipid rafts) dispersed in the liquid-disordered matrix of other unsaturated lipids (e.g., the lipid bilayer membrane, such as a primary lipid bilayer membrane). Lipid raft domains also can apparently preferentially include or exclude proteins. Typical examples of integral proteins, cytoplasmic proteins, and membrane receptor proteins that are preferentially included in lipid rafts include, e.g., GPI anchored proteins, SRC kinases, and gangliosides. The partitioning of particular components into raft domains is believed to be facilitated by the preferential packing of their membrane anchors with constituents in the lipid rafts, e.g., sphingolipids. Such proteins in lipid rafts can facilitate signaling functions thus rendering the rafts functional substructures within a biological membrane (e.g., both within natural membranes with naturally occurring lipid rafts and also within the micro-array membranes of the current invention). For example, Gm1 ganglioside serves as a native receptor for many bacterial proteins of the AB5 family (e.g., cholera-toxin). See, FIG. 13 for structure of cholera toxin, Gm1 and DPPC. AB5 proteins bind to up to five Gm1 molecules within the signaling domain (e.g., raft) before endocytosis occurs. Refunctionalization with lipid rafts herein is also useful in comprehensive studies aimed at determining the formation mechanisms and structure/dynamics/functions of lipid rafts. Thus, the current invention can be used to create micro-arrays of lipid rafts in a lipid membrane and to be used in spatially-resolved and time-resolved measurements to study formation, structure and function of lipid rafts. Such lipid rafts are optionally isolated from, e.g., cell surfaces, cell vesicles, etc. or are optionally purchased from any number of commercial suppliers. See, e.g. Dietrich et al., (2001) *Biophysical J.* 80:1417–1428 and van Meer, (2002) *Science* 296:855–856. Addition of such lipid rafts to micro-patterned primary lipid bilayers results in congregation of one or more rafts within the emptied non-lipid areas of the primary membrane. As explained in greater detail below, such lipid rafts are optionally vastly different in lateral lipid diffusion coefficients than the primary lipid membrane.

In some embodiments herein, various probes can be used for visualization or tracking (especially when lipid rafts are used for refunctionalization) that offer selective partitioning into a particular phase (e.g., into a lipid raft as opposed to a different type of bilayer membrane). Probes such as diI and diffusion of extraneous membrane-incorporated probes (e.g., fluorescent fatty acids) can reveal diffusion, etc. of lipid rafts and the like (as well as diffusion for non-lipid raft bilayers as well). As explained, the composition of phospholipid, sphingolipid, and cholesterol that facilitate the formation of stable rafts can be systematically varied in different uses (e.g., in order to manipulate diffusion coefficients, etc.). Additionally, ambient aqueous phase parameters can also be tailored herein (e.g., pH, temperature, ionic strength, etc.).

Figure 14:
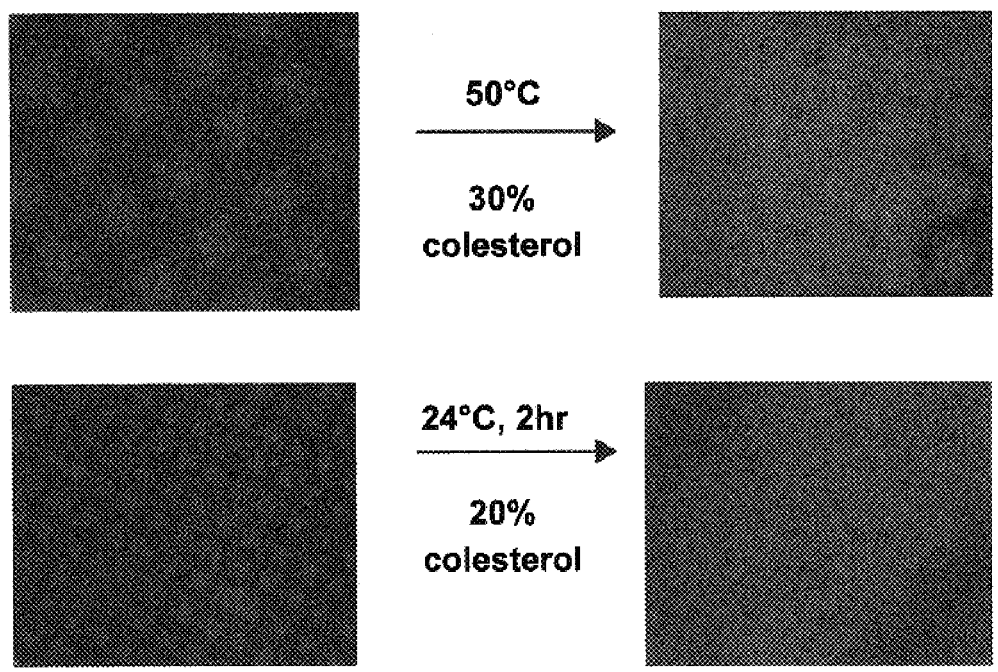
FIG. 14: Displays fluorescent images showing the effect of variable parameters on lipid raft stability within a patterned bilayer.

As will be apparent from discussion herein, various parameters are optionally manipulated in the embodiments to influence the stability, etc. of lipid rafts. For example, FIG. 14 reveals significant correlations between temperature, size of lipid raft-separated domains, cholesterol concentration, and the life-time for which the imposed phase-separated configuration is stable. Various parameters to change such stability can include, e.g., replacement of POPC in the matrix phase with POPC and cholesterol mixtures and POPC and sphingolipid mixtures. FIG. 14 shows examples of temperature time, cholesterol concentration and domain size effects on the stability of engineered lipid raft domains.

At 30 mol % cholesterol, the green raft domains are stable for several hours at room temperature, but diffuse away when temperature is elevated, etc. Raft compositions were roughly 37% POPC, 28% spingomyelin, 2% Gm1 and variable cholesterol. See FIG. 14. Green NBD-DHPE was used as the fluorescent probe. The rafts were put into a patterned background layer of 99% POPC and 1 mol % Texas-red-DHPE. Additional changes where POPC in the matrix phase is replaced with a stiffer lipid (higher transition temperature lipids, e.g., DMPC glycero-3-phosphoethanolamine (Marina Blue-DHPE) can also be carried out. NBD-DHPE and TR-DHPE cab be used as FRET partners primarily in such measurements, but newly available BODIPY pairs can also optionally be utilized.

Lipid Vesicles

In other embodiments, refunctionalization with a secondary lipid membrane (e.g., one comprising specific proteins of interest, etc.) is achieved through use of one or more lipid vesicle. Construction and use of lipid vesicles is well known to those. of skill in the art. Their use in refunctionalization of emptied areas in lipid membranes is similar to that of the previously described lipid rafts. For example, lipid vesicles containing such components of interest as specific proteins, are optionally constructed or purchased and used to refunctionalize the micro-patterned primary membrane.

As previously stated, lipid-free regions within a membrane pattern can be refilled by subsequent exposure to "secondary" phospholipid vesicles or the like. When the same lipids are used as secondary vesicles as are within the primary lipid bilayer, the membrane pattern can be gradually erased at a rate determined by the lateral diffusivity of the probe-lipid molecules across juxtaposed features. On the other hand, the addition of different lipid-types provides an important tool to systematically manipulate bilayer composition (controlled insertion, dilution, and localization of desired lipids) and design non-equilibrium phase-separated 2D lipid mixtures. Their approach to equilibrium via mixing can be monitored and long-lived metastable states for forming functional arrays of proteins and lipid rafts can be designed.

Figure 15:
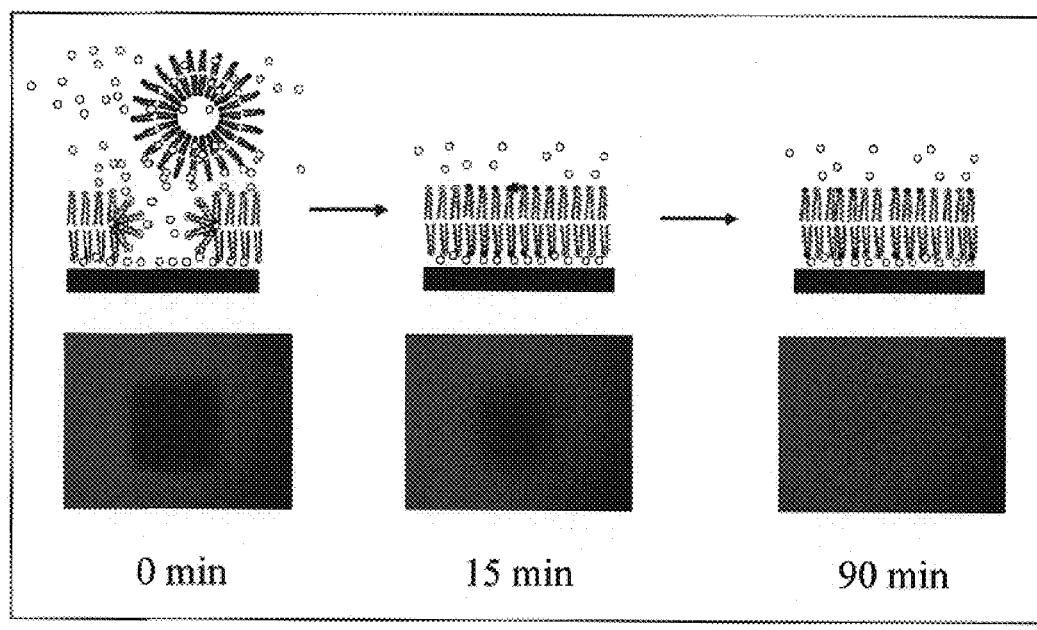
FIG. 15: Illustrates refunctionalization of emptied areas in a micro-patterned primary lipid bilayer membrane with secondary lipid bilayers of similar lipid composition.
Figure 16:
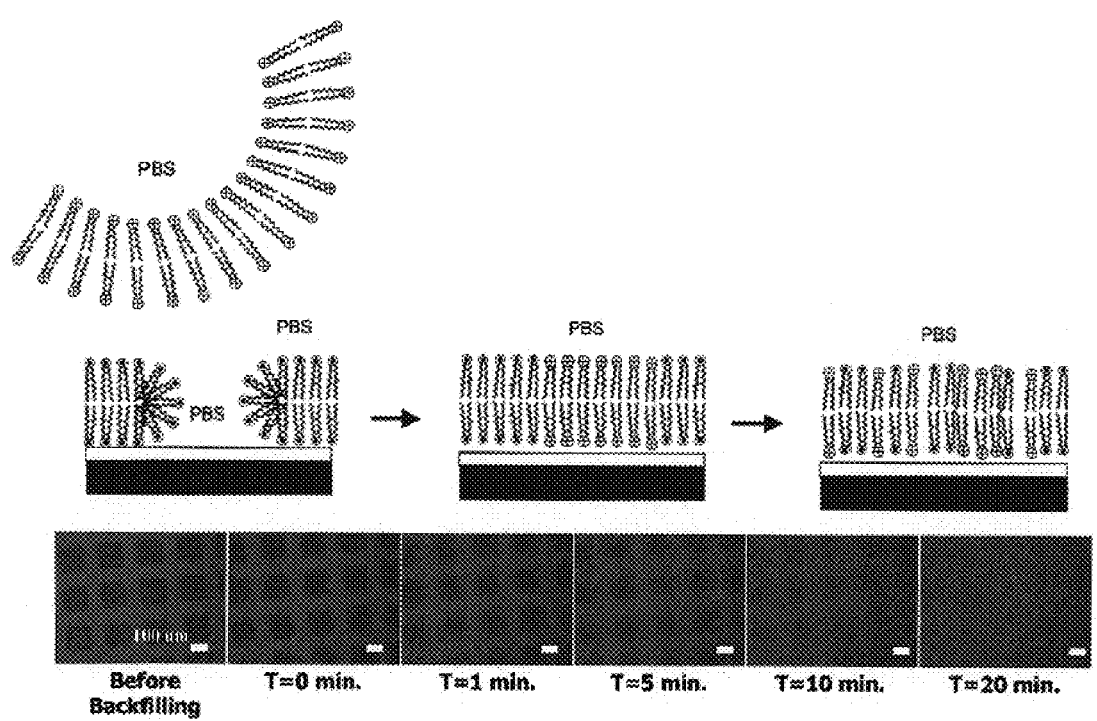
FIG. 16, Illustrates refunctionalization of emptied areas in a micro-patterned primary lipid bilayer membrane with secondary lipid bilayers of similar lipid composition.

FIGS. 15 and 16 illustrate concepts of refunctionalization. In one illustration, patterned membrane samples were exposed to vesicles of similar lipids (with no fluorescent probe-labeled lipids). The lipid was egg-PC and the initial patterned bilayer was doped with 1 mol % Texas-Red DHPE. The time-lapse images in FIG. 15 and 16 reveal that several minutes after the incubation, the initial non-fluorescent square voids began to acquire fluorescence from the background. The images reveal that the initial pattern was quickly transformed to a circular morphology, consistent with random Brownian motion of the labeled-lipids, which in several minutes led to the complete homogenization of the Texas-Red intensity across the entire sample surface thus eliminating the pattern. The time required for completely erasing the pattern was comparable to that required for fluorescence recovery in FRAP measurements, and large arrays of patterns could be simultaneously erased. It is thought that the incoming secondary vesicles must rapidly fuse with the surface at the unoccupied regions of the pattern forming non-fluorescent bilayer and become contiguous with the existing fluorescent bilayer through a bilayer-bilayer fusion, leading to a rate-determining thermal diffusion step. See, FIGS. 15 and 16.

Figure 17:
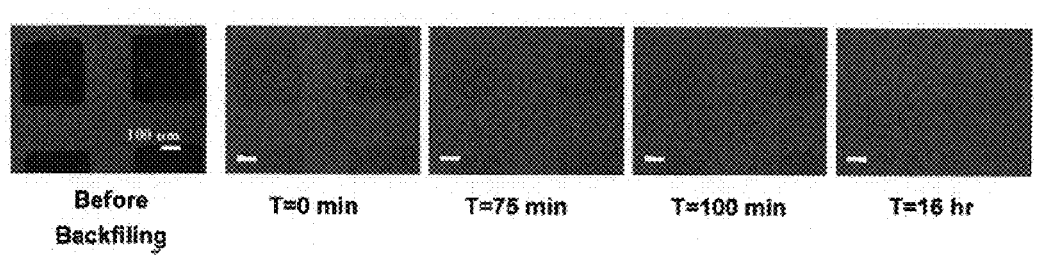
FIG. 17: Illustrate stability of refunctionalization (or backfilling) areas in a micropatterned bilayer membrane over time.

To further extend this strategy by introducing secondary lipids and lipid-mixtures of significantly different translational mobilities, stiffer (or high transition temperature) lipids, such as dimyristoyl snl-glycero phosphocholine or DMPC) phospholipid vesicles were used as sources of secondary lipids. When incubated with patterned samples of POPC, the DMPC vesicles occupied the lipid-free regions, but took a significantly longer time (~20 hours) to "erase" the fluorescently visible pattern (see FIG. 17) of primary egg-PC bilayer as is seen in FIG. 16. This is in comparison to 20 minutes for egg-PC for a 100×100 sq. μm void). This can be understood based on markedly different fluidity of the two phospholipids and preference of the TR-DHPE probe-lipid for the more fluid egg-PC phase. C.f., FIGS. 16 and 17.

Figure 18:
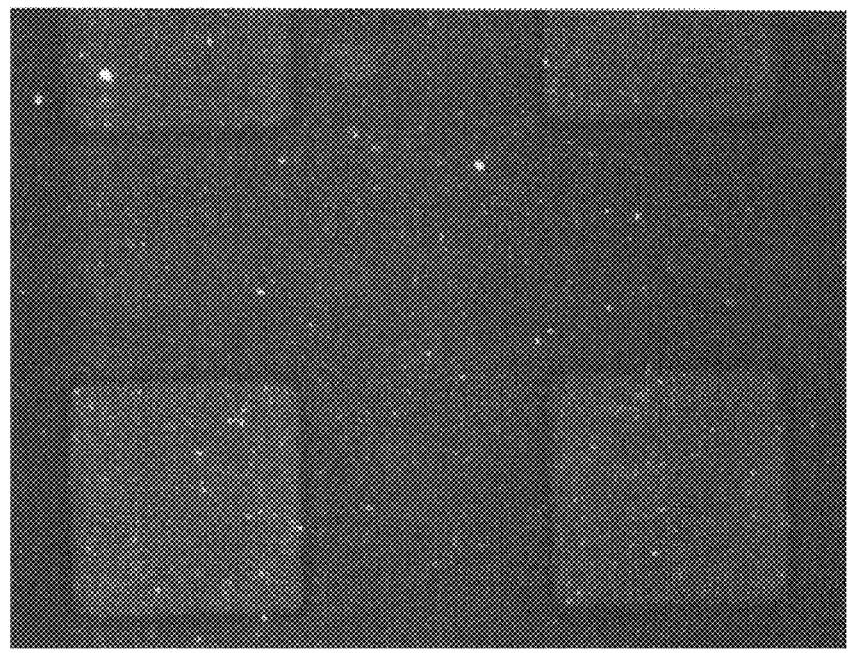
FIG. 18: Shows a two-color epifluorescence image of a FITC streptavidin microarray within a Texas-Red labeled fluid POPC bilayer.

To illustrate the potentially useful feature of the membrane lithography process (i.e., the UV patterning) herein is to provide a means to design functional microarrays within a membrane background. Regions of DMPC lipids doped with 1–10% biotin-DHPE were refunctionalized within the patterns created in a POPC bilayer. By simply exposing the fresh, unequilibrated mixed lipid surface (within 40 minutes) to labeled streptavidin (FITC-streptavidin), 2D microarrays of streptavidin were created which can be used for further functionalization. The epifluorescence image in FIG. 18 shows the formation of a FITC-streptavidin layer, almost exclusively within the unmixed boxes, which were stable for several days. More specifically, FIG. 18 shows a two-color (false colors) epifluorescence image of a FITC-streptavidin microarray within a Texas-Red labeled fluid POPC bilayer. The heterogeneous bilayer pattern was obtained by membrane photolithography of a Texas-Red-DHPE doped POPC bilayer followed by secondary backfilling (or refunctionalization) using vesicles composed of 10% Biotin-DHPE and 90% DMPC. The sample was then incubated with FITC-streptavidin for 10 minutes. In another illustration, when the secondary vesicles contained a lipid-mixture believed to represent typical composition of lipid rafts (e.g., 37% POPC, 30% cholesterol, 28% sphingomyelin, 2% GM1 [Ganglioside (Brain, Ovine-Ammonium Salt)], and 3% NBD-PE [1-Oleoyl-2-[6-[(7-nitro-2-1,3-benzoxadiazol-4-yl)amino]hexanoyl]-sn-Glycero-3-Phosphoethanolamine]), no diffusion of labeled species (NBD-PE or Texas Red-DHPE) occurred across the patterned features for several days. This observation illustrates that lipid raft-like aggregates can be engineered at pre-defined locations even in non-biological sizes and shapes within a fluid sBLM background.

In some embodiments herein, the composition of the secondary lipid bilayer membrane is also optionally controlled so that, e.g., the diffusion coefficient of the lipid of the secondary lipid bilayer membrane is different than that of the primary membrane and thus the refunctionalized areas are stable (to varying degrees depending upon, e.g., the amount of difference between the diffusion coefficients). Of course, it will be appreciated that the primary membrane is also optionally controllable in its diffusion coefficient. Thus, for example, a primary membrane of a predetermined or pre-selected diffusion rate is micro-patterned through use of the invention. Such micro-patterned primary membrane is then refunctionalized with, e.g., lipid vesicles derived and not modified from natural sources. See above for an illustration of refunctionalization of a micro-patterned primary membrane with lipid vesicles. It will be appreciated that, again, the refunctionalization of micro-patterned membranes optionally proceeds in any number of methods (e.g., refunctionalization of emptied areas with vesicles solutions in water or buffer wherein the lipids in the vesicles comprise the same lipids as those in the primary bilayer (either tagged with fluorescent probes or not), mixtures of two or more kinds of lipids, mixtures of lipids and cholesterol, etc.

Non-bilayer Refunctionalization

Not only are the emptied areas in the primary membrane capable of being refunctionalized with lipid bilayer membranes (i.e., "secondary" membranes), but such emptied areas can also optionally be refunctionalized with other components such as, but not limited to, proteins (i.e., ones not in a lipid membrane context), cells (either bound to one or more protein within a refunctionalized area or not), beads (such as latex, glass, or metal, any of which are optionally bilayer coated), and non-biological moieties (e.g., nanoparticles, glass beads, latex beads, coated beads, membrane compatible amphiphilic polymers, nanocrystals, colloids, quantum-dot materials, metals, metal beads, polymerizable precursor molecules, various non-biological polymers, catalysts, etc.). Basically, any moiety which can recognize the hydrophilic emptied area in the lipid bilayer and/or any moiety which can recognize (and optionally bind to or associate with) any underlying substrate, compound, moiety, etc. which is exposed through the emptied area is optionally utilized to refunctionalize any micro-patterned emptied area herein. For example, as explained below in greater detail, addition of various select proteins (i.e., those not within a lipid bilayer context) is optionally used in the refunctionalization of micro-patterned primary membranes. Additionally, nanoparticles (e.g., of various metals, etc. such as gold) are also optionally used to refunctionalize the emptied areas.

Figure 19:
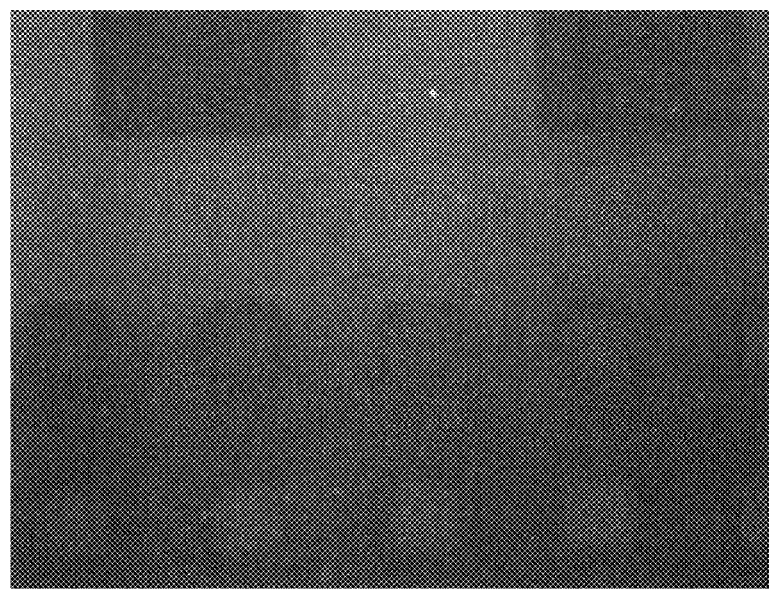
FIG. 19: Illustrate refunctionalization (or backfilling) of emptied areas in a patterned bilayer with a non-bilayer component (protein A) and human IgG antibodies.

An example of refunctionalization with a non-bilayer component is seen in FIG. 19. In FIG. 19, a patterned bilayer with lipid-free square regions were refunctionalized by first incubating the patterned bilayer with 10 microgram/ml solution of protein A in PBS buffer at 37 C. It was speculated that the protein A would occupy the lipid-free regions within the patterned bilayer. As can be seen from the figure, the protein A did indeed localized into the lipid free areas. Confirmation of such is given by fluorescent antibody binding specific for the protein. The antibody binding was done by incubating the sample with Alexa labeled human IgG, also at 37 C for 3 hours. The antibody had a strong preference for protein A and was resistant to attachment to the membrane surface. The green fluorescence observed in the figure is almost exclusively in the square lipid free areas. The resultant architecture composed of discrete and optically defined arrays of dynamic lipid regions and static, but functional, protein/antibody regions elaborates the application of the micropatterning protocol. It illustrates new opportunities in designing hybrid micro-arrays where both a pattern (here the square lipid free areas) and the background can be used as distinctly different functional areas. Such devices can optionally find applications in multiplexing protein and membrane arrays on single chip (a biphasic protein and membrane array).

Multi-component Refunctionalization

In typical embodiments herein, the components used to refunctionalized the various emptied areas in the primary membrane (e.g., the secondary membranes, proteins, etc.) are specifically arranged spatially within the primary membrane. In other words, specific components are used to refunctionalized specific emptied areas in the primary membrane, while other specific components are used to refunctionalize other specific emptied areas in the primary membrane. Thus, for example, a first type of secondary membrane (e.g., containing a specific mutation of a receptor protein) is used to refunctionalize a first set of specific emptied areas on the primary membrane, while a second (and optionally third, fourth, fifth, etc.) secondary membrane (e.g., each containing a different specific mutation of a receptor protein) are used to refunctionalized other specific emptied areas on the primary membrane. Of course, use of particular examples herein should not be construed as limiting on the invention. Those of skill in the art will quickly appreciate the adaptability of this concept and its application to, e.g., myriad screening application, assay application, etc.

Specific spatial refunctionalization is optionally accomplished in several ways. In one typical embodiment, a single UV mask is used to create a first pattern of emptied areas on a primary lipid bilayer membrane. The resulting emptied area(s) are refunctionalized with a first component (e.g., a secondary lipid membrane comprising a specific protein). The same UV mask is then rotated/shifted so that its UV-transparent areas are above different locations on the primary membrane. The primary membrane is then once again exposed to the appropriate UV light, resulting in a second pattern of emptied areas on the primary lipid bilayer membrane. Such second pattern areas are then optionally refunctionalized with a second component (e.g., a different secondary lipid membrane comprising a different specific protein or a non-biological catalytic moiety, etc.). Such steps are optionally repeated for all variables (i.e., for all of the secondary components to be utilized).

In yet other typical embodiments, a similar refunctionalization method takes place, except that instead of rotating/shifting the UV mask, differently patterned UV masks are used. The use of different UV masks allows for more complex and intricate micro-patterning on the primary lipid membrane. However, the basic concept remains the same: a determined number of emptied areas are created through use of a first UV-mask then refunctionalized in the primary membrane, a new UV mask is used to create a new set of determined emptied areas in the primary membrane which are, in turn, refunctionalized, etc. It will be appreciated, that in some embodiments herein, different emptied areas within the primary membrane are refunctionalized with different types or classes of components. For example, some areas are optionally refunctionalized with secondary lipid bilayers, while other areas are refunctionalized with such components as bare proteins or non-biological moieties, etc.

Furthermore, multiple layers of array complexity can be constructed in some embodiments herein through patterning of secondary membranes (or other refunctionalization constituents) which are themselves patterned within a primary membrane. In other words, a secondary membrane area can optionally refunctionalize an emptied area within a primary membrane; another round of UV-patterning can create an emptied area within the secondary membrane or refunctionalization component, which can also be refunctionalized with a tertiary refunctionalization component. Yet further rounds of patterning and optional refunctionalization can also be performed. Again, those of skill in the art will be able to visualize and appreciate various permutations on this theme (e.g., multiple rounds of patterning within specific areas to allow laying down of a finely patterned, complex array).

In the discussions of the various refunctionalizations herein it will be appreciated that both the primary lipid bilayer and the component (e.g., the secondary lipid bilayer, non-biological moiety, etc.) used to refunctionalize the micro-pattern are optionally of concern. In other words, in some embodiments, a primary lipid bilayer can be viewed as "mortar" surrounding "bricks" of interest in place (i.e., the refunctionalized areas). However, in other embodiments, the primary lipid bilayer is also of interest, either instead of, or in addition to, the refunctionalized areas. For example, in some embodiments, the primary bilayer area is optionally of interest in, e.g., measurement of such things as comparative binding and the like.

Additionally, it will be appreciated that in other embodiments herein, the UV-opaque masks are optionally utilized to create micro-patterns comprising spatially stable "islands" of lipid bilayer membranes. While in some typical embodiments, the resulting micro-pattern comprises a number of emptied hole arrays in a lipid bilayer, in other typical embodiments, the resulting micro-pattern comprises a number of distinct isolated lipid bilayer membranes surrounded by emptied areas. The UV-opaque mask used to construct such "island" arrays, thus, is a reverse or negative image of the type of UV-opaque mask used to construct the "hole" arrays (e.g., the mask is optionally a series of UV-opaque squares surrounded by UV-transparent grids, thus, resulting in bilayer "islands" surrounded by emptied grid areas, as opposed to a mask optionally comprising a series of UV-transparent squares surrounded by UV-opaque grids which results in emptied "holes" surrounded by lipid bilayer grid areas).

Stabilization of Refunctionalized Areas

In various embodiments herein, it is important and/or useful for the refunctionalization component added to the emptied area to not move (e.g., for the refunctionalization component to not diffuse into the primary membrane or change spatial location in the primary membrane). For example, in construction of typical micro-arrays and libraries it is desirous to have spatially stable components in order to perform the necessary screenings, etc. Such concerns are addressed by the current invention in several manners depending upon, e.g., the type of component used to refunctionalize the emptied areas in the primary membrane.

In cases wherein emptied areas in the primary membrane are refunctionalized with secondary lipid bilayer membranes (whether or not such secondary membranes comprise proteins, etc.) the refunctionalization component is optionally stabilized in the emptied area through one or more of several methods. In some embodiments the secondary lipid membrane used to refunctionalize the emptied area can comprise one or more polymerizable lipid. Polymerizable lipids are well known to those in the art and numerous examples of such are commercially available (e.g., from Avanti Polar Lipids, Alabaster, Ala., see, e.g., www.avantilipids.com and the references cited therein). Examples of possibly used polymerizable lipids include, but are not limited to, e.g., various diacetylene phospholipids, various phosphatidylcholine lipids, and other similar lipids. The polymerizable lipids used in refunctionalization of emptied areas create cross-linkages between themselves, thus preventing their diffusion out into the rest of the primary lipid membrane and also keeping lipids from diffusing into the refunctionalization area from other areas of the primary lipid membrane. A stable non-diffusing refunctionalization area is thus created through use of polymerizable lipids.

In yet other embodiments herein, secondary lipid membrane refunctionalization areas are stabilized through careful selection of varying diffusion coefficients. Thus, for example, a secondary lipid membrane to be used in refunctionalization of an emptied area is optionally comprised of a lipid bilayer membrane which has a different diffusion coefficient than the primary lipid bilayer membrane in which it is to be placed. Thus, stabilization of primary/secondary lipid bilayer areas is optionally controlled through modification/selection of diffusion coefficients of the respective bilayers. Since it is often found that the headgroup of specific lipids determines the lateral diffusion coefficient, incorporation of different lipids with different headgroups in either the primary and/or the secondary lipid bilayer is optionally used to control diffusion coefficients in such bilayers. It will be appreciated that diffusion coefficients of any or all of the various bilayers in a system are selected/chosen/constructed, thus, allowing for greater control of stability of interfaces between primary and secondary areas. For example, in some embodiments, it can be desirous to have secondary lipid areas which slowly diffuse into/with the primary lipid area, thus, allowing measurements over a time course of, e.g., membrane-bound protein activity in differing lipid environments, etc. Other embodiments comprise wherein the interfaces between the primary and secondary lipid bilayer areas are constant and little or no diffusion occurs.

In other embodiments herein which comprise non-bilayer refunctionalization components (e.g., non-biological moieties, etc.), the refunctionalization component is typically stable. In other words, such components typically do not diffuse spatially over or through the micro-patterned construct. This is typically due to the non-integration between such refunctionalization components and the primary lipid bilayer. Also, non-bilayer refunctionalization components such as free-proteins (e.g., various immunoglobulins such as IgG, etc.) optionally localize to emptied areas in a micro-patterned bilayer as well. Soluble proteins especially are optionally used to localize within non-lipid emptied areas, as are proteins or other moieties which bind to or associate with any substrate which is accessible via an emptied/open area in the micro-patterned bilayer.

Examples of Refunctionalization

As explained above, the lipid free emptied areas within the primary lipid bilayer membrane can be refunctionalized by subsequent exposure to numerous components, such as lipid vesicles (e.g., those comprising the same lipids as the primary membrane as well as those comprising different types of lipids than the primary membrane), protein solutions, and even non-biological molecules (e.g., polymers and colloids). This refunctionalization provides an important tool to engineer structural, compositional, and functional patterns within the membrane architecture. To illustrate refunctionalization, a micro-patterned primary lipid bilayer membrane comprising stable emptied areas within an egg-phosphatidylcholine primary lipid membrane was exposed to pure egg-phosphatidylcholine vesicles. In other words, the vesicles were not doped with fluorescent dye molecules and hence would not produce a fluorescence under the appropriate conditions, while the primary lipid membrane was doped with fluorescent molecules and thus would produce a fluorescence under the appropriate conditions. In embodiments wherein refunctionalization is carried out with various lipid bilayers or membranes, such bilayers are typically characterized as secondary lipid bilayers (i.e., as opposed to the primary background lipid bilayer). In embodiments wherein refunctionalization involves non-bilayer material, such materials are typically labeled as "refunctionalization components" or "refunctionalization materials," while in other embodiments, such non-bilayer materials are optionally labeled as secondary refunctionalization components or materials.

The time lapse images in, e.g., FIG. 15 reveal that within several seconds after the incubation began, the initial unoccupied square regions (i.e., the emptied regions) began to be filled in by the fluorescent dye (Texas red DHPE) from the background (i.e., from the fluorescently doped primary membrane). After 90 minutes, lipid diffusion had totally erased the micro-patternization of the lipid bilayer membrane. The images show that the initial square (i.e., the emptied area) was quickly transformed to a circle which in several minutes progressed to a complete homogenization of the Texas red intensity across the entire sample surface and an elimination of the grid pattern. It is to be appreciated that this progression followed a complex set of mechanistic events. First, the new incoming vesicles fused at the emptied regions of the micro-pattern, thus, forming non-fluorescent refunctionalized bilayer areas within the primary membrane (which was fluorescent). Second, the incoming vesicles became contiguous with the existing fluorescent primary bilayer through bilayer-bilayer fusion. Third, the various lipid components experienced lateral lipid diffusion through and between the primary and secondary membranes.

The transition in, e.g., FIG. 15 from the square to circle for.the fluorescence morphology appears to be driven by line tension once the new lipid molecules make the bilayer contiguous. Such refunctionalization involving lateral lipid diffusion of the secondary membrane into the primary membrane areas (and vice versa) is optionally utilized in various embodiments of the current invention, e.g., to create specific lipid membranes wherein components (e.g., proteins, specific lipids, etc.) are equally dispersed throughout a membrane. For example, a primary lipid membrane can be micro-patterned as described herein (e.g., a series of specific emptied areas are created). The micro-patterned primary membrane can then be exposed to a secondary membrane (e.g., as in FIG. 16) that comprises a lipid composition that allows diffusion between the primary and secondary membranes. The proteins, lipids, etc. in the secondary membrane are thus diffused out into the primary membrane. This equaling out can be utilized to create tailored primary membranes comprising specific ratios of components (e.g., components from the secondary membranes) and can also be used to study the mechanisms and dynamics of the diffusion itself (e.g., through tracing of the diffusion of such things as specific markers/fluorescent moieties in the primary membrane, the secondary membrane, or both). As mentioned previously, however, in many embodiments it is desirous not to have diffusion between the primary and secondary membranes. Several methods of the current invention are therefore optionally utilized to prevent such intermingling. See above.

As another example of refunctionalization of (supported) micro-patterned emptied (lipid free) areas, free protein, i.e., protein that is not bound within or upon a lipid bilayer, is optionally targeted to emptied areas in a micro-patterned membrane. For example, a sample lipid bilayer membrane is optionally micro-patterned (as described herein) to produce a micro-patterned lipid bilayer membrane. Such membrane can then be incubated with a solution of a protein (e.g., protein A, etc.). In various embodiments, the incubation time is optionally varied depending upon, e.g., the specific nature of the membrane components, the specific nature of the refunctionalization parameters (e.g., number, size, pattern of the micro-array), or the specific component used in the refunctionalization. It is expected that a soluble protein will occupy the lipid-free regions in the micro-patterned lipid bilayer, since such proteins are expected to deposit on the hydrophilic surface exposed through the emptied hole areas in the micro-patterned array. Such expectations of refunctionalization can be confirmed through anti-protein antibody screening. The refunctionalized lipid membrane can be incubated with, e.g., labeled IgG antibodies specific for the protein used to refunctionalize the areas. Additionally, the antibodies used are optionally resistant to attachment to the membrane surface (e.g., the primary micro-patterned membrane) and are optionally fluorescently labeled to aid in tracking. Another embodiment herein comprises wherein such free proteins (or optionally proteins within a secondary lipid bilayer) are sequestered within emptied areas of a micro-patterned bilayer and which can act as cell receptors and/or tethers. For example, various immunological molecules (e.g., co-stimulatory molecules or the like) are optionally used to activate/bind various immunologically important cells (e.g., T-cells, B-cells, etc.).

The resultant architecture produced by such protein:antibody refunctionalization (i.e., composed of discrete and optically defined arrays of dynamic lipid regions and static, but functional, protein/antibody regions) elaborates the breadth of possible applications of the current micro-patterning invention. Thus, new opportunities in designing hybrid micro-arrays are possible where both the pattern (i.e., the emptied micro-patterned squares) and the background (i.e., the primary lipid membrane) can be used as distinctly different functional areas. Such opportunities can find applications in such procedures as, e.g., multiplexing protein and membrane arrays on a single chip (i.e., thus producing a biphasic protein and membrane array).

Figure 20:
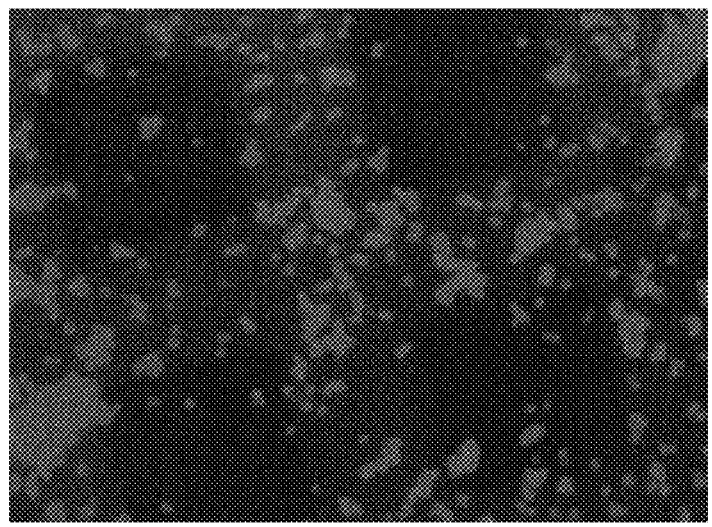
FIG. 20: Illustrates preferential incorporation of bilayer coated glass beads into lipid areas of a micro-patterned primary lipid bilayer membrane.
Figure 21:
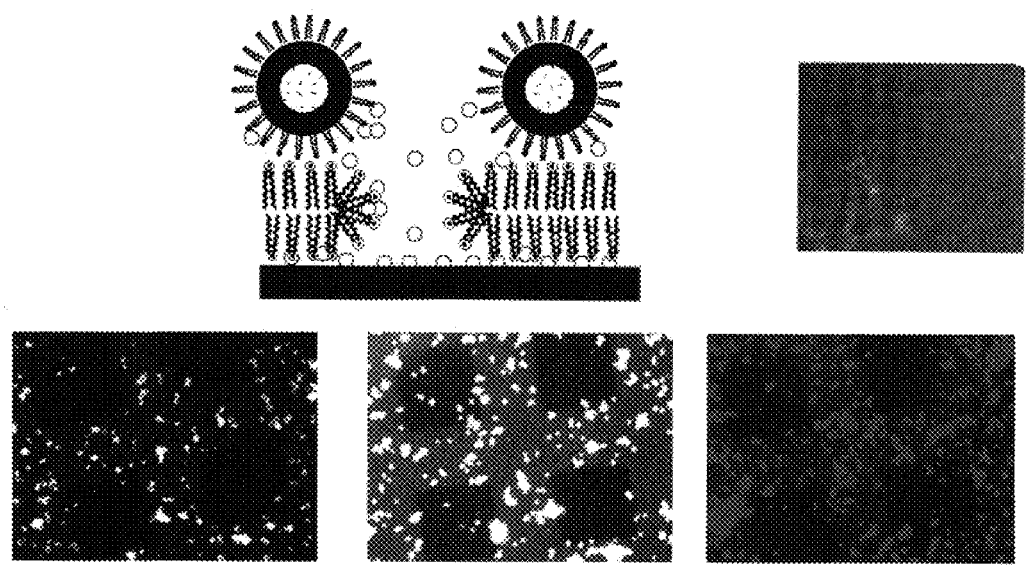
FIG. 21: Displays a schematic diagram and fluorescent images showing amplification of membrane patterning through use of bilayer coated beads.

Another example of refunctionalization of micro-patterned lipid membranes can be seen from the following illustration. Glass micro-spheres of 5 micrometer diameter were coated with a bilayer lipid membrane of the same composition as a primary bilayer membrane on the surface of a coverslip (or, e.g., a silicon wafer, etc.). The bilayers were composed of egg-PC with 1% Texas-red DHPE lipid. The bilayers were formed on the glass beads by incubation with vesicle solution under ultrasonic conditions. The beads were then introduced onto the patterned bilayer surface using PBS buffer as a transfer medium. As can be seen in FIG. 20, the lipid coated beads show a clear preference for the bilayer regions of the micro-patterned membrane (i.e., the fluorescence from the beads is clustered in the primary lipid membrane areas of the membrane as opposed to the emptied areas). Such specific targeted addition to selected areas of a micro-patterned membrane illustrates the versatility of the current methods. Such targeting of components to the non-emptied areas in a micro-patterned membrane is optionally used for, e.g., novel methods in sorting beads based upon their lipidic composition. FIG. 21 shows another example of bilayer coated beads interacting with specific areas upon a patterned membrane of the invention. FIG. 21 also depicts a schematic representation of interaction between the bilayer coated beads and a patterned membrane of the invention.

Figure 22A:
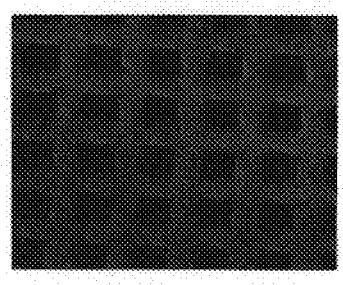
FIG. 22: Displays epifluorescence images of engineered rafts in a fluid lipid bilayer.
Figure 22B:
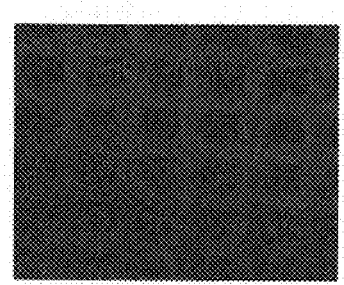
Figure 22C:
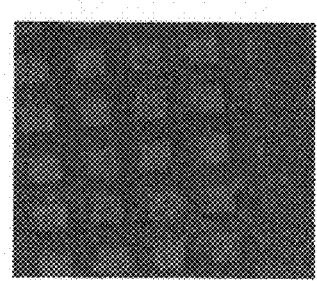

Yet another example of refunctionalization can be seen in FIG. 22. FIG. 22A shows epifluorescence images of engineered rafts in a patterned fluid lipid bilayer. Fluid lipid bilayers were prepared composed of POPC (1-Palmitoyl-2-Oleoyl-sn-Glycero-3-Phosphocholine) and 1 mol % Texas red DHPE (1,2-dihexadecanoyl-sn-glycero-3-phosphoethanolamine, triethylammonium salt). Using membrane lithographic approaches described herein and micro-contact printing, stable patterns of POPC incorporating 20×20 µm holes within the membrane architecture were created. Retention of membrane fluidity was confirmed using fluorescence recovery after photobleaching measurements. As shown in FIG. 22B, the membrane patterns were subsequently exposed for 10 minutes to a 50 microliter PBS solution of "raft" vesicles which were composed of: 37% POPC ($4.867 \times 10^{-7}$ moles), 30% cholesterol ($3.95 \times 10^{-7}$ moles), 28% spingomyelin ($3.68 \times 10^{-7}$ moles), 2% GM1 (Ganglioside (Brain, Ovine-Ammonium Salt)) ($2.63 \times 10^{-8}$ moles), 3% NBDPE (1-Oleoyl-2-[6-[(7-nitro-2-1,3-benzoxadiazol-4-yl)amino]hexanoyl]-sn-Glycero-3-Phospho ethanolamine) ($3.945 \times 10^{-8}$ moles). FIG. 22B shows the formation of designed rafts (green regions) that were stable for several days. FIG. 22C shows the addition of 2 µl FITC labeled CTB (Cholera toxin) ($4.3 \times 10^{-9}$ moles) to assess the localization of recognition function within raft microdomains.

Thus, FIG. 22 displays again, the ability to engineer membrane micro-domains, e.g., rafts enriched in sphingomyelin and cholesterol, within a fluid bilayer membrane by combining membrane patterning and backfilling or refunctionalization approaches. The metastable kinetic phases such as are created in the example (and in some other embodiments) are resistant to spontaneous mixing. Such resistance is presumably due to high activation energy barriers (e.g., at room temperature) and allows the creation of designed signaling and other regions in a microarray format. Of course, it will be appreciated that the theory or mechanism of such action should not be taken as limiting.

The stability of such micrometer scale phase-separated "raft" domains sharply differs from spontaneous mixing behavior observed for fluid lipid mixtures (see above) and further confirms their liquid-ordered character. It will be appreciated that this, and other examples herein, illustrate numerous possibilities of other optional embodiments and uses. For example, dynamics of cholesterol from the fluid phase to the sphingomyelin rich phase are optionally followed using similar constructions of the invention. Additionally, relations between the size of engineered raft domains and their stability in a fluid matrix can be followed through similar constructions of the invention. "Melting" of raft domains (e.g., green-NBD labeled) as a function of the properties of the aqueous medium in which the bilayers exist (e.g., ionic strength, temperature, etc.) are also optionally followed. Also, the relaxation of rafts upon preferential depletion of cholesterol (e.g., using methyl-β-cyclodextrin) from engineered regions can be examined with similar constructions of the current invention.

Kits, Reagents and Systems

The methods, etc. of the present invention are optionally provided to a user as a system or kit. As used throughout, the term "kit" should be understood to include examples of "systems" as well unless otherwise noted. For example, a kit of the invention optionally contains one or more primary lipid bilayer membrane (or components to construct such), UV-mask(s), refunctionalization components with, e.g., appropriate buffers, fluorescent moieties, etc. Most kits also typically contain one or more UV light source of the appropriate wavelength(s), and supports/holding devices or modules for proper placement of the lipid bilayer membranes, the UV masks, and the UV light source. The kit typically further comprises, one or more additional reagents, e.g., substrates/supports for lipid bilayer membranes, labels, appropriate buffers, tubes and/or other accessories, reagents for collecting/storing refunctionalization components, buffers, cover slips, etc. The kit optionally further comprises an instruction set or user manual detailing preferred methods of using the kit components for creation of micro-patterned lipid bilayer membranes and their refunctionalization as well as any specific intended used (e.g., for drug screening, genomic screening, etc.). Additionally, some kits can optionally comprise instruction information on proper selection and construction and/or purchase of appropriate membranes and refunctionalization components based upon user parameters. It will be appreciated that different kits will optionally comprise different instruction sets.

When used according to the instructions, the kit can be used, e.g., for construction of one or more micro-patterned lipid bilayer, and/or for refunctionalization and optional use of such constructed micro-patterned membranes. Such micro-patterned membranes (and optional refunctionalized micro-patterned membranes) are optionally utilized for any purpose described herein, e.g., for construction of protein libraries or protein arrays, or the like. Of course, it will be appreciated that use of the invention is not limited by particular usage embodiments detailed herein.

In other aspects, the current invention comprises a system or kit for construction of one or more patterned, modified, or chimeric lipid bilayer membrane. Such systems/kits typically and optionally comprise: one or more source of adjustable UV light, a source of one or more primary lipid bilayer membrane, one or more UV opaque mask that can be positioned between the UV light and the lipid bilayer membrane (and which comprises one or more UV transparent area), and one or more module for controllably positioning the lipid bilayer membrane in relation to the UV opaque mask and the UV light. In other embodiments, such systems optionally comprise a source of buffer(s) for the lipid bilayers and/or a device which selectably controls the UV light (e.g., a timer, etc.). Additionally, such systems optionally comprise one or more device for controllably positioning the UV mask in relation to the UV light and the lipid bilayer membrane. Yet other embodiments comprise wherein the system comprises one or more source of one or more secondary lipid bilayer membrane and/or one or more other refunctionalization component (e.g., proteins, non-biological moieties, etc. as described above). Further embodiments comprise devices/modules for replacement, alteration, shifting, or exchange of different masks between the UV light and the primary lipid membrane (e.g., for production of different micro-patterns on the primary membrane).

In an additional aspect, the present invention provides system kits embodying the methods, compositions, systems and apparatus described herein. System kits of the invention optionally comprise one or more of the following: (1) an apparatus, system, system component or apparatus component (e.g., substrates/supports for lipid bilayer membranes; holding/placement devices for the membranes, UV masks, UV sources, etc.; timers; water/solution baths; temperature regulators; etc.); (2) instructions for practicing methods described herein, and/or for operating the apparatus or apparatus components herein. In a further aspect, the present invention provides for the use of any apparatus, apparatus component, composition or kit herein, for the practice of any method herein, and/or for the use of any apparatus or kit to practice any method herein.

Additionally, the various kits herein can include appropriate packaging/storage material, containers for holding the components of the kit, instructional materials for practicing the methods herein, preservative components (e.g., for buffers, lipid bilayers, etc.) and/or the like.

While the current invention optionally comprises a number of systems or kits, recitation of specific exemplary kits/systems herein, should not be construed as limiting. Various kits can comprise, e.g., construction of one or more patterned lipid bilayer membrane (e.g., as opposed to a refunctionalized membrane). In some embodiments, such systems or kits can comprise: one or more source of an adjustable UV light, a source of one or more primary lipid bilayer membrane, one or more UV-opaque mask (comprising one or more UV transparent area) that can be positioned between the UV light and the primary lipid bilayer membrane and one or more module for controllably positioning the lipid bilayer in relation to the UV opaque mask and the UV light.

Other embodiments can optionally comprise systems or kits for construction of one or more modified or chimeric lipid bilayer membrane (e.g., as opposed to a non-refunctionalized patterned membrane). Such systems or kits can comprise, e.g., one or more source of adjustable UV light, a source of one or more primary lipid bilayer membrane, one or more source of one or more secondary refunctionalization component, one or more UV-opaque mask that comprises one or more UV transparent area and that can be positioned between the UV light and the primary lipid bilayer membrane, and one or more module for controllably positioning the lipid bilayer membrane in relation to the UV opaque mask and the UV light. The refunctionalization component(s) in such systems/kits can optionally comprise, e.g., one or more secondary lipid bilayer membrane or one or more non-lipid bilayer membrane material (e.g., a cell, a protein, a glass bead, a latex bead, a bilayer coated bead, a membrane compatible amphiphilic polymer, a nanocrystal, a colloid, a quantum-dot material, a metal, a metal bead, a polymerizable precursor molecule or the like). In other embodiments, the systems or kits optionally comprise one or more source of one or more lipid bilayer membrane buffer (e.g., water, PBS, etc.). Also, in other embodiments, the systems/kits optionally comprise a timer device which selectably controls the UV light (e.g., controls the duration, intensity, etc. of the UV light). Additionally, other optional embodiments comprise one or more device for controllably positioning the UV mask in relation to the UV light and the lipid bilayer membrane.

As explained in more detail below, numerous kits/systems of the invention comprise material for specific uses of patterned/refunctionalized membranes of the uses, but do not necessarily comprise methods or materials to actually construct the needed patterned membranes. In other words, the kits are for specific end uses of the patterned/refunctionalized membranes not for the construction of such bilayers.

Yet other embodiments comprise one or more packaging materials, instructions for using the systems/kits to produce one or more patterned lipid bilayer membrane, modified lipid bilayer membrane, or chimeric lipid bilayer membrane, or one or more containers for holding one or more component of the system/kit, e.g., one or more packaging materials (e.g., carton, transport stabilizers, etc.), one or more container for holding one or more component of the system/kit (e.g., one or more lipid bilayer membrane buffer, one or more module for controllably positioning the UV mask in relation to the UV light and the lipid bilayer membrane, etc.). Other embodiments also optionally comprise controllable incubation devices and/or the like appropriate for refunctionalization or any refunctionalization component into the micro-patterned array. As mentioned previously, it will be appreciated that typically each different kit can optionally comprise specific instructions for creation/use/ etc. of the lipid membranes herein.

Exemplary Kits

While it will be appreciated that the current invention comprises myriad embodiments of systems/kits/micro-patterned bilayers, etc. (and, again, specific examples herein should not be construed as limiting), certain examples include, e.g., systems/kits comprising environmental monitoring systems or kits for detecting or classifying one or more environmental moiety. In such exemplary systems/kits one or more refunctionalization component typically binds to or otherwise indicates the presence of the one or more environmental moiety (which optionally comprises one or more of, e.g., a bacteria, a bacterial toxin, a virus, a prion, a fungus, a fungal toxin, a chemical agent, etc.). Of course, in other embodiments, components in the primary membrane can bind to, or otherwise indicate, such presence. Examples of such environmental moieties optionally. include one or more of (or portions of (e.g., such as surface antigens/markers)), e.g.,: *Bacillus anthracis, Clostridium botulinum, Clostridium botulinum* toxin, *Yersinia pestis, Variola* major, *Francisella tularensis*, Hemorrhagic fever, a Filovirus, an Arenoviruses, Ebola virus, Marburg virus, Lassa virus, Machupo virus, a Hanta virus, *Coxiella burnetii*, a brucellosis causing bacterium, epsilon toxin of *Clostridium perfringens*, a *Salmonella* species, *Escherichia coli* 0157:H7, *Shigella, Burkholderia mallei, Burkholderia pseudomallei, Chlamydia psittaci*, ricin toxin, Staphylococcal enterotoxin B, *Rickettsia prowazekii*, a viral encephalitis virus, an alphavirus, Venezuelan equine encephalitis virus, Eastern equine encephalitis virus, Western equine encephalitis virus, a flavivirus, St. Louis encephalitis virus, *Vibrio cholerae, Vibrio cholerae* toxin, *Cryptosporidium parvum*, Nipah virus, distilled mustard, Lewisite, mustard gas, nitrogen mustard, phosgene oxime, ethyldicholoarsine, Lewisite 1 (L-1), Lewisite 1 (L-2), Lewisite 1 (L-3), methyldichloroarsine, mustard/Lewisite, phenodichloroarsine, sesqui mustard, arsine, cyanogen chloride, hydrogen chloride, hydrogen cyanide, chlorine, diphosgene, cyanide, nitrogen oxide, perfluororisobutylene, phosgene, red phosphorous, sulfur trioxide-chlorosulfonic acid, teflon and perfluororisobutylene, titanium tetrachloride, zinc oxide, Agent 15, BZ, canniboids, fentanyls, LSD, phenothiazines, cyclohexyl sarin, GE, sarin, soman, tabun, VE, VG, V-gas, VM, VX, bromobenzylcyanide, chloroacetophenone, chloropicrin, CN in benzene and carbon tetrachloride, CN in chloroform, CN and chloropicrin in chloroform, CR, CS, adamsite, diphenylchloroarsine, diphenylcyanoarsine, or a fusarium toxin. The binding/indicating component in such system/kits optionally comprises: an antibody against the environmental moiety, a specific protein which selectively binds the environmental moiety, a specific membrane protein which selectively binds the environmental moiety, a specific membrane lipid which selectively binds the environmental moiety, or a specific chemical element or compound that selectively binds the environmental moiety. Such system/kits are optionally used for, e.g., detection of environmental pollution, food-borne contamination, accidental or intentional release of pathogenic agents and/or potentially harmful chemicals, etc. Such kits for detecting or classifying one or more environmental moiety, optionally comprise one or more patterned lipid bilayer comprising a micro-array for detecting or classifying the environmental moieties (e.g., wherein the refunctionalization component(s), and sometimes also or alternatively, the primary bilayer binds to or otherwise indicates the presence of the environmental moieties) and one or more of, e.g., a container for containing the lipid bilayer, packaging material, or instructions for using the lipid bilayer for environmental monitoring.

Other exemplary system/kits of the current invention can comprise diagnostic kits for detecting or identifying a pathogen(s) in an organism. In such system/kits the one or more refunctionalization component (and optionally and or alternatively the primary lipid membrane) binds to or otherwise indicates a presence of the one or more pathogen or of one or more pathogen-related moiety (e.g., one or more of, e.g., a bacteria, a virus, a prion, a fungus, an infectious parasite, etc.). In such systems/kits, the one or more pathogen-related moiety can optionally comprise one or more of, e.g., an antibody of the organism against the one or more pathogen, a non-organism byproduct of the one or more pathogen, or a moiety produced by the organism in response to the one or more pathogen, etc. Additionally, kits for detecting or identifying pathogens in an organism, can comprise a lipid bilayer (e.g., a patterned array for detecting or identifying pathogens in an organism wherein the refunctionalization component (and optionally and/or alternatively the primary lipid bilayer) bind to or otherwise indicate the presence of the pathogens/pathogen-related moieties) and one or more of, e.g., a container for containing the lipid bilayer, packaging material, and/or instructions for using such lipid bilayer arrays for detecting or identifying the one or more pathogen.

Yet another exemplary system/kit of the invention can comprise a system or kit for detecting or identifying one or more nucleic acid sequence in one or more genome. In such kits, the refunctionalization component (and optionally or alternatively the primary lipid bilayer) binds to or otherwise indicates the presence of the one or more nucleic acid sequence. Such one or more nucleic acid sequence optionally can indicate a presence of one or more disease (e.g., a congenital disease) in an organism which comprises the one or more genome. Additionally, the one or more nucleic acid sequence can optionally comprise a plurality of nucleic acid sequences and binding of the one or more nucleic acid sequence thus can identify one or more organism comprising such genome of the one or more nucleic acid (e.g., thus detecting the presence of a specific organismal genome in a mixture of different organisms). The current invention can also comprise kits for detecting or identifying specific nucleic acid(s) in one or more genome. Such kits can comprise a lipid bilayer array for detecting or identifying the nucleic acid(s) and one or more of, e.g., a container for containing the lipid bilayer, packaging material, or instructions for using the lipid bilayer for detecting or identifying the one or more nucleic acid.

Still other exemplary system/kits of the invention can optionally comprise drug profiling systems or kits for detecting or identifying one or more drug within an organism. In such options, the secondary refunctionalization component (and optionally and/or alternatively the primary lipid bilayer areas) binds to or otherwise indicates a presence (or prior presence, e.g., based upon such things as metabolites of the drug(s) in question, etc.) of the one or more drug within the organism. Such systems/kits can optionally be tuned to detect the presence/prior presence of one or more of any desired drug product (e.g., as in illegal narcotics, legally prescribed pharmaceuticals, etc.). For example, such systems/kits can optionally detect, e.g., one or more of: a cannaboid, cocaine, a barbiturate, methaqualone, sopor, parest, quaalude, mecquin, a benzodiazepine, chloral hydrate, phencyclidine, LSD, mescaline, peyote, psilocybin, DMY, DET, psilocyn, an amphetamine, an amphetamine derivative, heroin, codeine, morphine, an opiate, meperidine, hydromorphone, methadone, methamphetamines, phenmetrazine, etc. In typical embodiment such detection is performed on a human subject (but other organisms are also optionally screened for drug presence, e.g., horses, cattle, insects, fish, amphibians, plants, etc.). Such systems/kits also can optionally be used to screen various sample formats (e.g., blood, saliva, hair, skin, tissue, or mucus, of the organism or any combination thereof). The invention, thus, can comprise kits for detecting or identifying one or more drug within an organism. Such kits can comprise a patterned lipid bilayer array for detecting or identifying the drug(s) and one or more of, e.g., a container for containing the lipid bilayer, packaging material, or instructions for using the lipid bilayer for detecting or identifying the one or more drug, etc.

Another exemplary system/kit of the invention comprises a system or kit for identifying the effect or efficacy of one or more putative therapeutic or preventative drug on one or more organism (e.g., a drug testing system/kit). In such situations, the one or more refunctionalization component (and optionally and/or alternatively the primary lipid bilayer areas) binds to or otherwise indicates the effect or efficacy of the putative drug. The secondary component optionally comprises one or more moiety from the organism that is capable of interacting with one or more infectious agent or one or more product of one or more infectious agent (e.g., a waste product or shed moiety from an infectious agent or disease state (e.g., cancer, etc.). Thus, the one or more putative drug optionally binds to or alters the one or more infectious agent. Alternatively, the one or more putative drug binds to or alters the one or more moiety of the organism. It will be appreciated that such kits are also amenable to drug screening for non-infectious diseases/disease states such as some types of cancers, congenital diseases, etc. In some systems/kits herein, the one or more refunctionalization component comprises one or more secondary lipid bilayer membrane, one or more non-lipid bilayer material, or one or more of, e.g., a cell, a protein, a glass bead, a latex bead, a bilayer coated bead, a membrane compatible amphiphilic polymer, a nanocrystal, a colloid, a quantum-dot material, a metal, a metal bead, a polymerizable precursor molecule, etc. The invention thus can comprises kits for identifying the effect or efficacy of one or more therapeutic or preventative drug on one or more organism. Such kits can comprise a patterned lipid bilayer micro-array for identifying the effect or efficacy of the one or more drug and one or more of a container for containing the lipid bilayer, packaging material, or instructions for using the lipid bilayer for identifying the effect or efficacy of the one or more drug.

It will be appreciated that the invention, thus, comprises numerous embodiments of kits/systems intended for specific purposes (e.g., various screenings, etc.). The above exemplary embodiments should not be construed as limiting.

It will be appreciated that the current invention also comprises the actual patterned lipid bilayer membranes (optionally refunctionalized) contained within the above exemplary kits. Additionally, however, it should be noted, that such claimed membranes should not be construed as limiting other membranes which fall within the claimed invention.

Exemplary Uses of Micro-patterned Lipid Bilayer Membranes

The patterned lipid bilayers constructed through the current invention (both those that are refunctionalized with various components and those that are not) are useful in myriad applications. For example, the current invention is optionally useful in such arenas as: materials synthesis, catalyst discovery, chemical and biological sensor microarrays, massively-parallel genomics, drug screening, and proteomics research. The patterned membranes herein can be used for construction of screening devices for early detection of disease in an organism (e.g., by binding/interaction of a protein or lipid or the like that is arrayed on a patterned membrane of the invention and an indicator of the disease in the organism such as a protein from an infectious agent such as a bacterial pathogen or a cancer cell or the like). Screening and discovery of therapeutic/prophylactic compounds or drugs can be carried out in a similar manner. Other examples of use include, e.g., use of the controlled production of potent oxidants (e.g., singlet molecular oxygen and ozone) created in the micropatterning herein in the vicinity of artificial membranes of controlled compositions to provide chemical strategies for mapping roles in various membrane ruptures such as occur in bacterial killing. While certain exemplary uses are listed throughout, recitation of such different uses herein should not be construed as limiting.

The current invention offers significant opportunities to introduce functional substructures within a lipid bilayer matrix and produce novel compositional and structural membrane micro-arrays. For example, the use of this technique can create membrane-receptor micro-arrays for development of biosensor or chemsensor array, e.g., stochastic and ion-channel switch biosensor arrays. Additionally, the current invention also finds application in construction of other membrane-protein micro-arrays, micro-arrays used for biosensors, drug screening and proteomics, as well as micro-arrays to track, e.g., host-pathogen interactions. Study of cellular adhesion, e.g., as in inflammation and wound healing, can also be examined/screened through use of the various patterned membranes and methods herein. The current invention also optionally allows engineering of specific membrane composition (e.g., as involving fluidity, structure, etc.), and the creation of milieus for combinatorial synthesis of new materials (e.g., combinatorial nanotechnology material synthesis). The current invention also allows creation of dynamical assemblies of bio-colloids at membrane surfaces. It will be appreciated that the versatility of the invention allows for multiplexing of various activities within a single membrane, e.g., both chemical and biological detection/screening upon a single membrane construct, etc.

The constructs and methods herein involving patterned bilayers are applicable to a wide range of uses. For example, the current invention can be used for the biophysical characterization dynamical processes in membranes. Such approach allows juxtaposition of two distinct membrane environments whose approach to equilibrium can thus be probed. Also, the current invention allows for the creation of membrane-mimetic tools such as can be used for life science and environmental research in drug screening and discovery, membrane, membrane/protein, and membrane associated/protein microarrays, as well as membrane-based biosensors, proteomic platforms, high throughput screening, protein separation, etc. Various more detailed descriptions of several of these embodiments are described elsewhere herein. Again, it should be noted that specific recitation of particular usage embodiments herein should not be taken as limiting upon the current invention unless specifically stated so. The invention also provides materials applications. For example, the invention can provide spatially localized reaction chambers for parallel chemistries within the holes or the membranes, resist material with low-defects for subsequent metallization within the membrane holes, etc.

Figure 23:
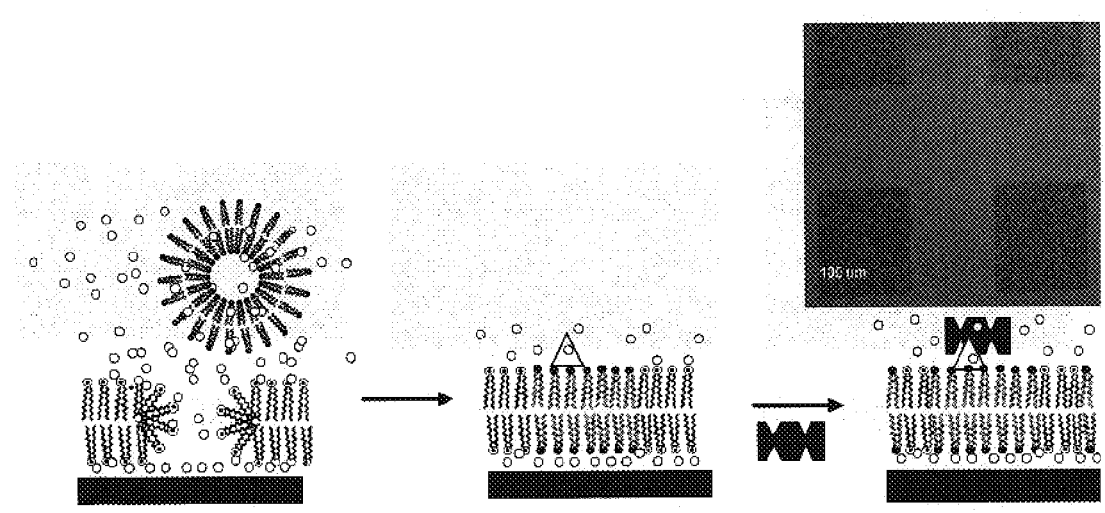
FIG. 23: Displays schematic diagrams and a fluorescent image showing selective protein localization in refunctionalized areas due to binding to moieties within such areas.

As a more specific example, the constructs and methods of the current invention can be used for high throughput assays for 2D protein crystallization. The ability to use the refunctionalized bilayers herein to prompt 2D crystallization of proteins leads to use of the invention in assaying crystallization habits of proteins in a high throughput manner. Specific regions of samples can be created that vary in the amount of biotinylated lipids or the membrane phase that surrounds them, thereby assaying the dependence of crystal structure on the concentration of the binding moiety (e.g., biotin) and the nature and fluidity of the surrounding lipid phase. For example, FIG. 23 shows a biotinylated lipid (represented by a triangle in the figure) within a refunctionalized area of a patterned bilayer. Streptavidin which binds with biotin (and which is represented with a incised rectangle in the figure), thus, binds to the biotin forming a complex. Because the biotinylated lipids are within a refunctionalized area, the streptavidin which binds to them will be localized to the same area. Thus, FIG. 23 shows a false-color epifluorescence image in red, green, and two-color channels for a FITC-streptavidin microarray within a Texas-red labeled fluid POPC bilayer. The heterogeneous bilayer pattern was created through UV patterning as described herein followed by refunctionalization with vesicles composed of 1% Biotin-DHPE and 99% DMPC. The bilayers in the figure were then incubated with FTFC-streptavidin for 10 minutes.

Yet another exemplary use of patterned bilayers of the invention involves cell trapping/capture/adhesion by membranes and/or membrane components. For example, use of patterned membranes herein can allow antibody mediated cell capture and optional activation. In some embodiments, membrane patterns composed of alternating features of lipids (e.g., POPC) and lipid+psg1-1 receptor antibodies can be created. PSGL-1 antibody can be tethered via a biotin-lipid-streptavidin-biotin-PGSL-1 sandwich. Neutrophils can then be rolled or flowed across the surface of such patterned membranes. The neutrophils can then be captured by domains within the patterned membrane that contain the antibodies and any activation of the neutrophils can be detected. See below as well.

Visualization/Tracking of Patterned Membranes

As explained above, the patterned lipid membrane arrays of the invention can optionally comprise refunctionalization with numerous moieties depending upon, e.g., the specific needs of the array. In some typical arrays herein, the refunctionalized areas comprise specific proteins (e.g., typically, but not exclusively, membrane bound and/or membrane associated proteins) or specific lipids or lipid structures. Specific events such as binding of other moieties (e.g., binding of one or more proteins being screened to one or more proteins or the like in a specific area on the microarray) can be detected and monitored in a number of ways. The detection/monitoring methods listed herein should not be construed as limiting. The literature is replete with examples of reaction/binding/etc. monitoring formats and the like, that are applicable, amenable, and capable of being used with the current invention by those of skill in the art.

For example, in some embodiments, reactions/bindings and the like are optionally monitored through use of, e.g., optical wave guides, surface plasmon resonance, fluorescence, radiation, etc. Surface plasmon resonance (SPR) (e.g., Biacore AB, www.biacore.com) monitors interactions of moieties through measurement of the mass concentration of the molecules close to a surface (such as the micro-patterned lipid bilayers of the invention) and is optionally adapted to use with the current invention and is optionally contained within kits/systems, etc. herein (e.g., see, above). Thus, one of the moieties that is involved in an interaction is optionally attached to or associated with a refunctionalized area and/or, in some embodiments, with a primary lipid bilayer area. The molecule to be interacted with such moiety is then, e.g., washed or incubated with the membrane surface. Any interaction is measured by a local concentration change and an SPR response (which is directly proportional to the mass of the molecules that interact with the surface of the membrane). The SPR measured comes from reflected light from a conducting film between two media of different refractive index (e.g., the micro-patterned membrane and a supporting substrate of the appropriate composition such as metal coated glass or the like). The SPR, thus, causes a decrease in the intensity of reflected light at specific angles.

The concentration and refractive index change when, e.g., a molecule being screened and a moiety on the micro-patterned array interact, thus, an SPR response can be detected. Additionally, interactions with different refunctionalization areas and/or primary bilayer areas (e.g., comprising different proteins, etc.) are capable of being individually monitored. Such responses can be plotted over a time course to determine the progress and kinetics of any interaction.

In other embodiments, the interaction, etc. of various moieties (e.g., a molecule being screened for and another molecule bound to the micro-patterned lipid bilayer which interacts with such molecule) is monitored through, e.g., fluorescence or radiation. For example, fluorescently labeled molecules on the membrane can optionally bind to other molecules in the buffer, etc., thus causing a decrease, loss, or change in fluorescence. Alternatively, fluorescently labeled molecules in the buffer, etc. can bind to moieties on the micro-patterned bilayer, thus, fluorescing when bound (e.g., thus showing interaction between molecules since the fluorescent molecule was not rinsed away, etc.). Again, each refunctionalization area and/or primary bilayer area is optionally individually monitored (e.g., via different fluorescences, etc.), thus, allowing separate individual examination of the different moieties in each refunctionalization area and within the primary bilayer areas. Monitoring of molecular interactions via fluorescence (and also radioactive markers) is quite well known to those of skill in the art and different combinations of fluorophores, techniques, ions, etc. are optionally adapted for use with the methods and micro-patterned membranes herein. See, e.g., Haugland (2002) *Handbook of Fluorescent Probes and Research Chemicals* Published by Molecular Probes, Inc., Eugene, Oreg.

Other means of visualization or tracking of the various constructs and methods herein can include, e.g., various optical and vibrational imaging techniques such as epifluorescence imaging at high magnification, fluorescence-microscopy (FM), Fourier-transform infrared microscopy (FT-IRM), imaging ellipsometry (IE), optical waveguide light spectroscopy (OWLS), total internal reflection illumination condition (TIRF), attenuated total reflection configuration FTIR (ATR-FTIR), etc. As mentioned above, FRET (Forster resonance energy transfer) and FRAP (fluorescence recovery after photobleaching) are also useful in visualization of the constructs and methods herein. Those of skill in the art will be quite familiar with numerous other means of visualization that are capable of use herein. Some such other means can be found in, e.g., Overney, et al., *Langmuir* 10:12–81–88 (1994); Frisbie, et al., *Science*, 265:2071 (1994); Singh, et al., *Biophys. J.* 60:1401–1410 (1991); and Salome, et al., *Eur. Biophys. J.*, 27:391–402 (1998).

Additional techniques optionally utilized to study/track membrane structure and assembly, interaction between various moieties, and even refunctionalization can include, e.g., atomic force microscopy (AFM, including functional group measurements) and fluorescence detection and imaging (see, above). Current state-of-the-art scanning probe microscopy (SPM) techniques can easily visualize nanometer scale features (and domains) based either on angstrom-level morphological differences or on the differences in surface chemical composition. SPM, which is based on lateral force microscopy (LFM) is especially successful in studying domains in lipid membranes, and is optionally used to visualize lipid bilayer membranes and micro-arrays herein. See, e.g., Overney, et al. (1994) *Langmuir* 10:1281–1288 and Frisbie, et al. (1994) *Science* 265:2071. Scanning confocal microscopy also provides opportunity to study/track the heterogeneity of lipid membranes and micro-arrays by using optically-labeled lipid components. Techniques such as fluorescence recovery after photobleaching (FRAP) can characterize the diffusion of various membrane components. See, above and Salome, et al., (1998) *Eur. Biophys. J.* 27:391–402. Additionally, high-speed single molecule level imaging at total internal reflection illumination condition provides the ability to follow individual molecular trajectories of molecules diffusing around membranes (provided that the molecule bearing the optical label diffuses far enough). Visualization means for analysis of patterned membranes herein are also optionally augmented with the FTIR suite of spectroscopy and microscopy tools for chemical identification, conformational characterization of lipids, and protein-lipid bindings, etc.

FRET measurements using TIR illumination are also optionally used in visualization of various embodiments herein. In such cases, the juxtaposed membrane phases will be labeled with fluorescence donor and acceptor probes (e.g., NBD-DHPE (530/550) can be a donor and TR-DHPE can serve as an acceptor). Illumination can occur by an Ar-ion laser and FRET signals can be captured using a high-speed, high-sensitivity Roper Cascade CCD or the like. FRET signal at the onset of refunctionalization, etc., when two adjacent membrane phases share the diffusive front, will confirm their contiguity. As the mixing proceeds, the FRET signals will achieve a homogeneous distribution. Such measurements can be used to corroborate epifluorescence measurements. To correctly capture the formation of lipid rafts, appropriate selection of fluorescence labels can be of importance. A wide range of amphiphilic dyes are commercially available. These are typically composed of a fluorophore that localizes either in the head-group region or within the tail anchor of a phospholipid molecule. Some visualization have relied on the use of NBD-PE which has a preference for the raft-like dense membrane environments and expulsion of Texas-red PE which has a preference for the fluid phase (e.g., of the patterned primary lipid bilayer). Other embodiments can optionally use BODIPY FL C-5-Ganglioside Gm1 (Molecular Probes, Eugene, Oreg.) which targets raft compositions. Other probes for the condensed phase that can be optionally used include, e.g., C18DiI, DiA, and DPH. To allow multicolor imaging, Marina Blue 1,2-dihexadecanoyl-sn-glycero-3-phosphoethanolamine (Marina Blue-DHPE) can be used. NBD-DHPE and TR-DHPE can be used as FRET partners primarily, but newly available BODIPY pairs could optionally be used as well.

Figure 24:
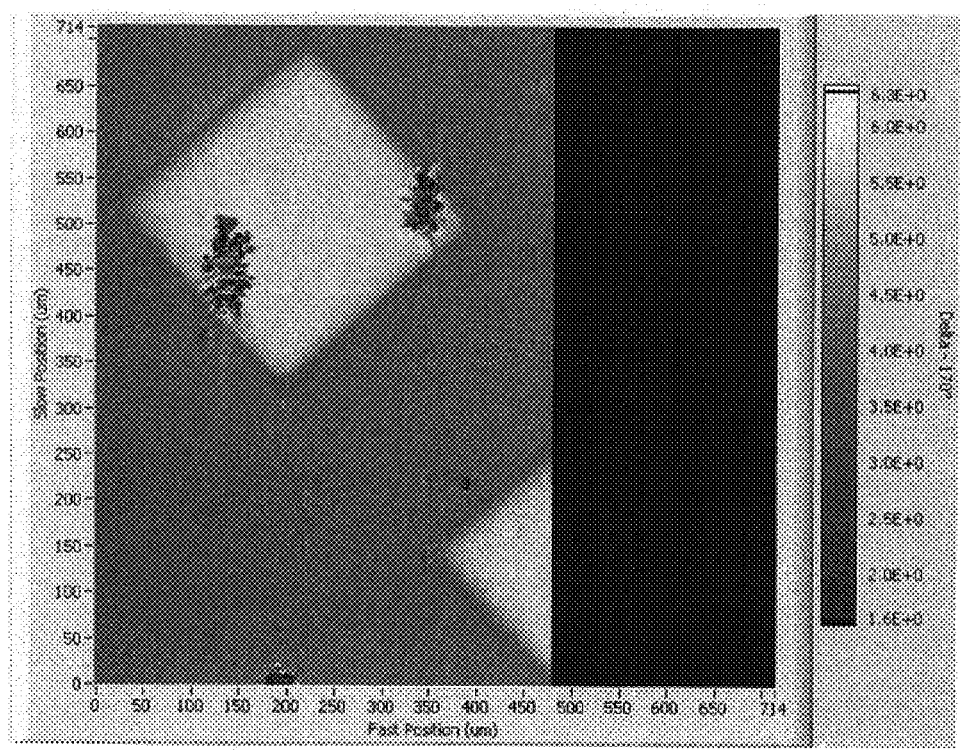
FIG. 24: Displays an ellipsometric imaging of a label-free (fluorophore-free) patterned bilayer of the invention.

It will be noted that the fluorophores used in the methods and constructs herein are used only for the purposes of visualization. In other words, the fluorophores used (if at all) do not create the patterning, etc. herein. Fluorophore free systems show similar patterning as do those systems which use fluorophore visualization. For example, FIG. 24 shows a label-free ellipsometric imaging of membrane topography. In the figure, a POPC bilayer was patterned through use of the current invention on Si wafers with 250 um holes. Bright areas in the figure reveal the absence of a bilayer and dark areas reveal a uniform bilayer. The smudged area within the figure is a unrelated particle within the aqueous phase above the bilayer used to focus the sample in the ellipsometer.

Exemplary Uses and Interactions/Associations of Patterned Membranes

In the various embodiments herein, the screenings and other monitorings, optionally comprise any of a number of different interactions or reactions. Again, listing of particular interactions/reactions herein should not be construed as limiting. For example, the patterned (and optionally refunctionalized) membranes herein can optionally be used in screenings and the like wherein the interactions between molecules (e.g., a molecule within the micro-patterned membrane and a molecule within a test sample) can involve, e.g., enzymatic reactions such as for oxidases, reductases, peroxidases, and the like. Also such interactions can optionally involve, e.g., antibody/antigen interactions, protein/ligand interactions, enzyme/substrate interactions, charged particle/charged particle interactions, nucleic acid/nucleic acid interactions (including antisense interactions), nucleic acid/protein interactions, lipid/lipid interactions, lipid/protein interactions, lipid/enzyme interactions, lipid/sugar interactions, lipid/detergent interactions, steroid/steroid receptor interactions, toxin/detoxification agent interactions, interactions involving ribozymes, and interactions involving polymers, metal, inorganic catalysts and the like with an organic molecule or bio-molecule or inorganic molecule. Organic/organic interactions, organic/inorganic interactions, and inorganic/inorganic interactions between different moieties are also involved in various optional embodiments of the invention herein.

Thus, using such monitoring systems, but not being limited to such monitoring systems, the current invention is optionally utilized for such actions as construction of biosensor arrays. For example, the current invention is optionally used to detect and monitor binding of such things as cholera toxin to membrane-incorporated ganglioside GM1 (a glycolipid) receptors which undergo biospecific aggregation when recognized by their pentavalent protein partner, cholera (see, e.g., Fishman, et al., (1993) Adv. Lip. Res. 25:165–187). The cholera protein appears to undergo a secondary self-assembly to form structured aggregates of cholera protein. These assembly processes are complex by nature and involve the co-operative dynamics both of the proteins and/or glycolipids involved and the molecules of the bilayer membranes. The emergence and stability of such temporal sub-structures that form to carry out particular functions is of growing importance in many fields of study. The current invention, therefore, can be used to aid in systematic studies to generate comprehensive fundamental understanding of the characteristic properties of such structures. In particular, the synergy and competitions involved in the protein-protein and lipid-protein interactions, the roles of functional external stimuli, and the life-times of such function-induced assemblies can be followed through use of the patterned arrays of the current invention. For example, micro-patterned bilayers comprising GM1 lipids (e.g., various mutations or versions of such in different refunctionalized areas or within areas of the primary lipid bilayer) could be exposed to cholera toxins and the reaction followed by, e.g., any of the monitoring methods herein, or other common reaction monitoring methods well known to those of skill in the art. As will be appreciated, other more complex formulations are also as applicable as such basic interactions.

The current invention is also optionally used to monitor and explore the dynamics of formation of lipid rafts in model membranes. Creation of micro-patterned membranes herein provides an opportunity to monitor spontaneous emergence of lipid raft areas as a phase-separated membrane state from an imposed non-equilibrium lipid mixture. For example, a supported lipid bilayer composed of phospholipids can be prepared and micro-patterned through use of the current invention. The "holes" in the micro-array can be of various sizes and in various number densities in such membrane (see, above). The holes are then optionally refunctionalized by spontaneous spreading of vesicles composed of sphingomyelin and cholesterol. Such an "imposed" or engineered membrane mixture will then evolve toward its lower free energy state aided by the mobility and diffusion characteristics of the two lipids. The mixing behavior can be monitored using time-lapse fluorescence, FRET, and infrared microscopic experiments to probe the raft formation in mixed component lipids. Such studies can be optionally carried out using systematically varied relative fractions of phospholipids, sphingomyelin, and cholesterol and systematically varied phospholipid fluidity. The relations between the chemical composition of lipid rafts and their emergent structures as revealed by their size, shape, fluctuations, stability, etc. are also optionally determined through use of the current invention. For example, through the patterning and refunctionalization of the micro-arrays, etc. of the invention, questions concerning the critical membrane matrix composition needed for phase separated raft domains to emerge; the relationships between the overall composition of the lipid mixture and those in the incipient raft microphases; the role of cholesterol in emergence/stabilization of rafts; the typical raft sizes and size distribution; the threshold size for a nanophase separated raft-domain; characteristic size and shape fluctuations in lipid rafts; selective leaching out of non-raft backgrounds using detergents (e.g., in DRMs) to better visualize rafts, can all be examined. Thus, in some embodiments, the micro-arrays and micro-patterning and refunctionalization techniques of the invention can be used to further study lipid rafts.

For example, sBLM models composed of phospholipid, glycolipid, and cholesterol in systematically varied concentrations can be prepared and fully characterized. The bilayers can then be micro-patterned and refunctionalized through use of the invention. The chemical structure of the incipient lipidic phase can be determined using FTIR in attenuated total reflection (ATR) mode. Lipid raft chemical composition can be assessed by functional-group imaging in AFM. ATR-FTIR measurements of detergent resistant BLM fragments on substrate surfaces can provide additional indirect measurement of raft chemical composition. To assist the FTIR measurements, deuterated lipids or sphingolipids can be employed. The structural properties of lipid rafts, including their topography (e.g., size, height, shape, and fluctuations) and frictional attributes can be assessed using AFM and fluorescence microscopy measurements. These measurements across the sample series can then be used to develop detailed correlation maps between raft structure and their chemical composition. Additionally, the micro-patterned bilayers of the invention can be used in determining the dynamical properties of lipid raft domains (e.g., lipid diffusion coefficient) and the relation to the overall membrane fluidity. Such measurements can optionally employ primarily FRAP measurements (see, above) in a semi-quantitative mode. Thus, by using selectively labeled phospholipid or sphingolipids (e.g., with Texas red, BODIPY, and NBD dyes), diffusion coefficients of the lipidic components in raft-containing bilayers (e.g., those micro-patterned bilayers of the invention) can be measured. Various factors can also be manipulated and their effect on lipid raft diffusion coefficients measured, thus, the composition of phospholipid, sphingolipid, and cholesterol that facilitate the formation of stable rafts can be systematically varied in various refunctionalization areas or on different membranes, etc. The ambient aqueous phase can also be tailored (e.g., pH, temperature, ionic strength, etc.). Real-time addition/depletion of lipids (e.g., Gm1 gangliosides) and cholesterol can also be carried out. Quantitative comparisons of mobilities thus derived with raft-free bilayers can also be carried out to allow inference of raft dynamical properties. Such constructions can help in addressing concerns such as the quantitative diffusion coefficients for lipids and their differences for lipid raft and non-raft domains; how raft micro-environments perturb the Brownian dynamics of lipid in membranes; whether mobility of raft domains requires concerted movement of raft constituents; how rafts respond to internal and external stimuli; whether cholesterol (in incubations subsequent to initial bilayer formation) partitions preferentially into rafts; whether cholesterol depletion leads to raft disassembly, etc.

Furthermore, use of micro-patterned bilayers of the invention can help in determination of functional consequences of lipid raft structure and dynamics. For example, a bilayer can be patterned and the resulting holes can be refunctionalized with lipid raft structures of various compositions (e.g., specific types of raft within specific refunctionalization areas, etc.). For example, analysis of Gm1-cholera interactions (e.g., done with Gm1-decorated bilayers wherein Gm1 comprises a physiologically relevant concentration, e.g., 0.1–10% and cholesterol and other sphingolipids) can be performed with micro-arrays of the current invention. In some embodiments, preferential partitioning into rafts can be characterized with fluorescence probe studies using labeled Gm1. Gm1's recognition of cholera toxin can then be tested by incubating the samples with probe-labeled cholera enterotoxin (e.g., B5 subunits) using fluorescence resonance energy transfer (FRET), AFM, and ATR-FTIR. Such procedures can optionally address, e.g., the extent of Gm1 preference for lipid raft domains, whether raft microstructure is essential for Gm1-cholera toxin binding, the correlations between raft properties (both structural and dynamic) and the Gm1-cholera binding, etc.

Additionally, use of the current invention can be used to create detailed "phase diagrams" for fluid bilayer lipid membranes. Thus, micro-patterning lipid bilayers followed by insertion of refunctionalization constituents, allows creation of synthetic model membranes in a full range of chemical compositions and structural complexities. This allows mapping of a phase diagram depicting the membrane fluidity as a function of its composition (e.g., fraction of cholesterol) and temperature.

Furthermore, the current invention can also be used to develop a more comprehensive understanding of membrane-mediated clustering of extraneous proteins. Through use of Gm1 (the membrane bound receptor-ligand) and cholera toxin (its water soluble protein partner) in micro-arrays of the invention, the effects of membrane fluidity on the aggregation of Gm1 and of cholera toxin in molecularly engineered model membranes can be studied.

Also, signaling domains (or functional rafts) are optionally engineered within a phospholipid bilayer at geometrically defined locations through use of the current invention. Sphingolipid and cholesterol-rich lipids (which are the main constituents of lipidic rafts) are optionally incorporated within membrane patterns, thus, creating platform membrane models where the signaling functions occur at predefined locations and offer addressability. Functional consequences of raft structure and dynamics can be assessed using recognition property of raft-bound Gm1 gangliosides for cholera toxin proteins.

Nucleation and growth of inorganic materials under the control of the fluidity of the bio-membrane environment are also optionally carried out through use of the current invention, thus offering routes to engineer two-dimensional crystal habits through the control of diffusion and the growth process. The current invention can optionally provide means to examine the crystallization pathway and optionally an in-situ characterization of critical nucleation sites. The invention also optionally provides a matrix to design 2D crystals of prototypical calcite and silica beads (colloidal crystals) and the exploration/characterization/use of membrane dynamics to direct the assembly of nanoparticles.

Furthermore, the current invention and its products are optionally used to, e.g., detect presence or absence of a protein or toxin or chemical compound based upon their interaction with a moiety or moieties in an arrayed pattern of the invention. Thus, a wide range of possible proteins/toxins/chemicals/moieties/etc. can be screened for simultaneously or sequentially. The differentiation between different compounds/proteins/etc. is also optionally included into micro-patterns of the invention (e.g., as in differentiating between different subtypes of bacterial antigens and the like). Such screenings are useful in numerous situations such as bioterrorism detection, environmental monitoring, diagnostic disease screening, screening for the presence of pathogenic contamination (e.g., in foodstuffs contaminated with *E. coli* strains, fusarium, etc.) For example, in a hazardous release context (either intentional or accidental), micro-patterned arrays of the invention can be used in field settings to detect and to type specific released agents such as viruses, bacteria, chemical agents, etc. Such detection could optionally be through detection of specific typing surface antigens on the pathogens by specific antibodies localized within specific regions of the micro-patterned membranes of the invention. Thus, a certain specific region of the micro-patterned bilayer can indicate the presence of (and also determine the type of), e.g., a bioterrorism agent, pathogen, etc. The detection of specific binding is optionally through any of the monitoring methods mentioned herein (e.g., fluorescence, SPR, etc.) or through other commonly known binding monitoring methods well known to those of skill in the art.

In yet other embodiments, the micro-patterns of the invention can optionally be used to perform, e.g., competitive binding assays and the like to be used, e.g., in drug screening. For example, putative drug candidates are optionally screened for their ability to prevent or inhibit infection as measured by, e.g., binding to cell surface proteins (e.g., ones in refunctionalized areas in the micro-patterned bilayers). In other situations, depending upon the specific compounds, etc. being examined, the putative drug itself is optionally monitored for binding to moieties in the micro-array (e.g., as in when a drug would bind to a cell receptor and thus prevent infection by a pathogen). Thus, different refunctionalization areas within a membrane can comprise different biding/screening moieties, etc. As is true in many embodiments herein, the micro-patterned bilayers of the invention are quite beneficial in screening and other actions because the proteins, moieties, etc. in the micro-arrays are within a natural or naturalistic milieu similar to an in vivo setting. Other types of bioscreenings and bioassays for drug screening are well known to those of skill in the art and are adaptable to use with the methods and micro-patterned bilayers of the invention.

Other common embodiments of the invention include micro-patterned bilayers that are capable of use in screenings with antibodies. It will be appreciated that many permutations are possible in such regard. For example, antibodies are optionally washed in a buffer over micro-arrays of the invention, thus, binding to specific localized moieties within the micro-array. Additionally, antibodies are optionally specifically localized within the micro-arrays (e.g., by being bound to specific refunctionalized areas, by being localized as "free" proteins in lipid-free areas in the array, etc.). Such screenings can optionally be used for, e.g., diagnostic screening for diseases, antigen screening, antigen typing, screening of antigen libraries (including recombined antigen libraries), etc.

As mentioned previously, the invention is also useful in studies of various cell-cell and membrane-membrane interactions. For example, cell binding as involved in immunological settings (e.g., co-stimulatory molecules, etc.) is optionally studied through the current invention. Thus, an array of various types or variations of cell markers and the like can optionally be arrayed through the current invention (e.g., in different refunctionalization areas), and their interactions with various cells (e.g., T-cells, B-cells, etc.) tracked by incubating the appropriate cells under the correct conditions with the micro-arrays. Interaction is optionally tracked through any number of means (e.g., see above).

Other useful assays involving the current invention comprise assays such as those mentioned and briefly described above in the Kits section. For example, detecting/classifying environmental moieties, detecting/identifying pathogens (e.g., within an organism), detecting/identifying nucleic acid sequences (e.g., within organisms or within libraries, recombinant libraries, etc.), detecting/identifying drugs (e.g., within an organism or within a sample), identifying effect/efficacy of therapeutic/preventative agents on an organism (e.g., as measured by such putative agents' effects on such actions as cell binding, etc.).

Also, the current invention is optionally utilized in such actions as the study of membrane structure, dynamics and assembly (e.g., apoptosis, endocytosis, electroporosis, lipid and/or protein diffusion or fusion, protein-recognition, etc.); modeling of membrane-mediated biophysical processes (such as protein-membrane interactions such as involved in clustering and membrane-membrane interactions such as in fusions or synapses, etc.); and the study of non-linear processes in diffusive-reactive systems (such as crystallization). For example, specific membrane compositions can be tailored through patterning and refunctionalization of membranes herein. The specific composition can be substantially homogenous (e.g., as components diffuse into and out of refunctionalization areas) or substantially heterogeneous (e.g., in embodiments wherein the refunctionalization components are designed not to diffuse into the primary bilayer). Other membrane structure and dynamic actions are also optionally followed via use of refunctionalized micro-patterned membranes of the invention. For example, lipid rafts are found to important in numerous biological processes/actions (see, e.g., Anderson et al., (2002) *Science* 296: 1821–25, Anderson et al. (2000) *Nature Immunology* 1(2): 156–162, etc.). Thus, construction of lipid membranes through refunctionalization with specific lipid rafts (and optionally specific proteins within such rafts) allows broadened study opportunities (e.g., comparison of action between different and/or changed lipid rafts, etc.).

As described previously, creation of micro-patterned lipid bilayers and refunctionalization with various types of secondary lipid bilayers are optionally used in a variety of applications. For example, lateral lipid and protein diffusion in lipid membranes is optionally analyzed through inclusion of specific markers (e.g., fluorescently labeled lipids and/or fluorescently labeled proteins) either within the secondary lipid bilayer used in refunctionalization and/or within the primary lipid bilayer. Additionally, such diffusion of refunctionalized micro-patterned areas is optionally modified through selection of primary lipid bilayers and secondary lipid bilayers of varying lipid diffusion coefficients, which influences the speed, character, etc. of the mingling of the different bilayers.

Typical uses for many micro-patterned/refunctionalized lipid bilayer membranes as described herein also include their use in a myriad of protein arrays and protein libraries. Thus, biphasic arrays of functional membranes and proteins on single substrates are conveniently produced. Such arrays and libraries are especially useful since the native-like surface of the lipid membrane allows for more natural conformations, etc. of many proteins and lipids, etc. Such naturalness is especially true of typical membrane-bound and membrane-associated proteins to be used in protein arrays and protein libraries. Uses for protein micro-arrays (and, indeed, for myriad micro-array structures and configurations) such as are constructed through use of the current invention, are well known to those of skill in the pertinent art.

Other uses of micro-patterned membranes of the invention can comprise, e.g., involvement in determination of structure of bio-molecules (e.g., proteins). For example, x-ray crystallography utilizes crystallized molecules to determine their structure. However, construction of such crystals is quite problematic with membrane bound or membrane associated proteins. Micro-patterned membranes of the current invention are optionally used to grow crystals of such membrane proteins at the well-defined two dimensional matrices in the micro-patterned membranes of the invention.

In yet other embodiments, the current invention is also optionally used to monitor membrane facilitated selective transport. For example, channels (e.g., ion channels) composed of membrane proteins or membrane protein complexes can be selectively refunctionalized within micro-patterned arrays of the invention. Thus, such ion channel biosensors can optionally be used for, e.g., drug screening bio-assays/kits and the like (see, above). For example, different permutations of channels are optionally localized within specific refunctionalization areas on a micro-patterned lipid bilayer. Various compounds (e.g., putative inhibitors, facilitators, modulators, etc.) are then interacted with the micro-patterned bilayer and the activity of the different ion channels is monitored. Monitoring is optionally performed through any of the methods described above, or other available monitoring methods available to those of skill in the art. For example, ion channel monitoring through impedance measuring (e.g., see, www.ambri.com) is optionally used within the current invention to monitor ion channel activity in the micro-patterned membranes herein.

In yet other embodiments of the current invention, the micro-patterned membranes (and, e.g., kits/systems comprising such, methods for making such, and methods for utilizing such) are optionally used in combinatorial synthesis of materials/compounds. For example, non-refunctionalized emptied areas within a micro-patterned membrane can be used to selectively "grow" or construct specific constructs (e.g., pure crystals of membrane proteins, etc.).

In typical constructions and methods herein, various bilayer and refunctionalization components are created and/or manipulated. The following section details a number of common protocols and materials used in such creations/manipulations. Of course, those of skill in the art will be familiar with other possible means of creation of, e.g., supported lipid bilayers, fluorescent membranes, etc., which are also amenable to use with the current invention. Thus, specific recitation of protocols used, etc. should not be taken as limiting unless stated to be so.

Materials: 1,2-dimyristoyl-sn-glycero-3-phosphocholine (DMPC), 1 1-palmitoyl-2-oleoyl-sn-glycero-3-phosphocholine (POPC), and GM1 ganglioside (Brain, Ovine-Ammonium Salt) for use in the current invention can be obtained from Avanti Polar Lipids (Alabaster, Ala.). Texas Red® 1,2-dihexadeconoyl-sn-glycero-3-phosphoethanolamine triethylammonium salt (TR-DHPE), N-(7-nitrobenz-2-oxa-1, 3-diazol-4-yl)-1,2-dihexadecanoyl-sn-glycero-3-phospho ethanolamine, triethylammonium salt (NBD-DHPE), N-(biotinoyl)-1,2-dihexadecanoyl-sn-gylcero-3-phosphoethanolamine, triethyl ammonium salt (biotin-DHPE), Marina Blue® 1,2-dihexadecanoyl-sn-glycero-3-phosphoethanolamine (Marina Blue®-DHPE), and Fluorescein labeled streptavidin (FITC-streptavidin) can be obtained from, e.g., Molecular Probes (Eugene, Oreg.). All lipids are typically suspended and stored in chloroform or chloroform/alcohol mixture in a freezer (−20° C.) until use. Cholesterol and sphingomyelin can be obtained from Sigma-Aldrich (Milwaukee, Wis.). Hydrogen peroxide (30% v/v) and sulfuric acid can be purchased from J. T. Baker (Phillipsburg, N.J.) and Fisher Chemicals (Fairlawn, N.J.), respectively, and used as received. All organic solvents are typically of HPLC grade. All chemicals are generally used without further purification. Organic-free deionized water of high-resistivity (>16.0 mΩ-cm) used herein can be obtained by processing water through a Milli-Q Plus Water system (Model ZD40-11595, Bedford, Mass.) consisting of a reverse osmosis de-ionization cartridge and an ion exchange/carbon purification system. Phosphate buffered saline (PBS, PH=7.2, 154 mM NaCl, 1.54 mM KH2PO4, and 2.71 mM Na2HPO4) is obtainable from Gibco-Life technology (Rockville, Md.) and used as buffer. Corning glass coverslips (No. 11/2, 22 mm2, Fisher HealthCare, Houston, Tex.) are typically used as substrates unless noted otherwise. Silicon substrates with native oxide overlayers (Silicon Sense, Nashua, N.H.) are generally used in control experiments.

Formation of Supported Lipid Bilayers: Supported POPC bilayers used herein are typically formed using previously reported vesicle fusion and rupture methods. See, e.g., Groves, et al., *Langmuir*, 14:3347 (1998). Briefly, small unilamellar vesicles (SUVs) are prepared using vesicle extrusion methods. See, e.g., Mayer, et al., *Biochim. Biophys. Acta*, 858:161–168 (1986). Typically, a desired amount of lipid or lipid mixtures suspended in chloroform or chloroform/methanol mixture is mixed in a glass vial. The solvent(s) is then evaporated under a stream of nitrogen and subsequently evacuated for at Millipore water and kept at 4° C. overnight. The total lipid concentration is usually 2 mg/ml. The hydrated aqueous solution is then sonicated and passed through a Avanti Mini-Extruder (Avanti, Alabaster, Ala.) using 0.1 um polycarbonate membrane filters (Avanti, Alabaster, Ala.) for 21 times at a desired temperature (usually at least 10° C. above the transition temperature for the lipids). The SUV solutions are stored at 4° C. until use. Substrates are typically prepared for bilayer depositions by immersing silicon and Corning coverglass substrates for a period of 5–10 minutes. in a freshly prepared 4:1 v/v mixture of sulfuric acid and hydrogen peroxide) maintained at ~90° C. The samples are then withdrawn using teflon tweezers, rinsed immediately with, copious amount of deionized water, and stored under water. Cleaned substrates are typically used within 1–2 hours of the pretreatment. Bilayer samples are prepared by placing a clean substrate surface over an ~80 ul SUV drop placed at the bottom of a crystallization well. The sample are allowed to incubate for approximately 5 minutes to ensure equilibrium coverage. The well is then filled with buffer solution, transferred to a large reservoir of buffer, and the coverslips shaken gently to remove excess vesicles. The sBLM samples prepared in this way are then stored in water or PBS buffer for further use in UV lithography (i.e., the UV patterning herein) and characterization.

UV Illumination of Supported Bilayers: Spatially-directed deep UV illumination of supported bilayers herein can be achieved using a physical mask and a deep UV grid-lamp as illustrated in the figures and specification herein. The mask displaying patterns of, e.g., chrome over quartz substrate can be obtained from sources such as Photoscience, Inc (Torrance, Calif.). UV radiation can be produced using a medium-pressure Hg-discharge grid lamp (UVP, Inc., Upland, Calif.) in a quartz envelope, and maintained in a closed chamber in a chemical hood. While still under buffer, the masks are gently lowered onto the bilayer samples placed in a crystallization dish filled with PBS. The sample system is then carefully placed in a UV/ozone-generating environment such that the coverslips are about 5–7 mm away from the light source. The exposure period is typically approximately 10–20 min. unless noted otherwise. The amount of buffer (or water) on the sample surface is optimized to ensure that the samples remain submerged during the entire illumination process while allowing the lamp-sample distance to be as small as possible (5–7 mm, etc.). During the illumination process, the sample temperature is often noted to slightly increase from 25° C. to 31° C. Following the exposure, samples are typically immersed in a large buffer bath, the mask separated from the substrate surface, and stored in buffer (or water) for further characterization.

Epifluorescence Microscopy: Nikon eclipse TE2000-S inverted fluorescence microscopes (Technical Instruments, Burlingame, Calif.) can be equipped with an ORCA-ER (Model LB 10-232, Hamamatsu Corporation, Bridgewater, N.J.) or Retige-1300 CCD camera (Technical Instruments, Burlingame, Calif.), and a low power mercury arc lamp as the light source, can be used to visualize all florescent samples. Data acquisition can be by simple PCI (Compix, Inc., Cranberry Township, Pa.) software augmented with a quantitative dynamic intensity analysis module. Excitation and emission filters are often in two separate filter wheels. Fluorescence images taken with the Texas Red filter set are assigned the color red, while images taken with FITC filter are assigned the color green. Semiquantitative assessment of the mobility of fluorophores within the membranes can be made using microscopy-based fluorescence photobleach recovery measurements by adapting the circular spot photobleaching method. See, e.g., Axelrod, et al., Biophys. J. 6:1055–1069 (1976). Specifically, a circular region of the fluorescent bilayer sample, ~30–50 um diameter, can be illuminated at high power continuously at the excitation wavelength for the fluorophore through a 60× objective for ~2 minutes. Such exposure bleaches a dark spot on the bilayer caused by the photoexcitation of the fluorophore followed by an irreversible chemical transformation effected by its reaction with dissolved oxygen. After this intense and extended illumination, the objective is replaced by low power observation beam and a 10× or 20× objective to record wide-field images of the fluorescence recovery in the bleached area at every 10 second interval. The recovery results from the diffusion of active fluorophore-lipids from the unbleached background into the bleached spot. It has been previously established that the shape of the recovery curve depends on the size and uniformity of the bleached spot as well as the thermal diffusion coefficient of the fluorophore in the bilayer environment. See Axelrod, supra. Consequently, the recovery curves can be used to get an estimate for the fluorophore diffusion constant, D, a measure of the fluidity of the bilayer environment and any fraction of lipids that are immobile. Soumpasis's model (see Soumpasis, Biophy. J. 41:95–97 (1983)) can be used to estimate the diffusion coefficients for the fluorophore lipids. It should be noted that since the spots used in the adaptation of the approaches herein are very large (50 um diameter) allowing diffusion during the photobleach, the estimates derived herein typically are not quantitative and reflect both the measurement inaccuracies and any sample heterogeneities over the sampled area.

Attenuated Total Reflection Fourier Transform Infrared (ATR-FTIR) microscopy: ATR-FTIR spectra can be recorded using a Bruker Equinox 55 Fourier transform infrared spectrophotometer equipped with a horizontal ATR accessory (Spectra-Tech, Inc., Shelton, Conn.) and DTGS detector (Bruker, Göttingen, Germany). The spectra are typically obtained at a 2 cm-1 resolution for 400 scans using a Blackman Harris 3 term apodization. The spectrometer is purged with dry and carbon dioxide free air. 45° Si or Ge trapezoids, mounted in a boat configuration to allow liquid ambients, are typically used as internal reflection elements (IRE). The number of active internal reflections in the IRE is typically N=11. Before use, the IREs are cleaned by a brief exposure to UV radiation followed by extensive rinsing in Millipore water. For a precise determination of peak positions, the interferrograms are zero-filled to increase the point density by a factor of 4. The data analysis is typically performed using Grams 32 (Galactic Industries, Salem, N.H.) software. Single bilayers are deposited by exposing the IRE elements to the vesicle spreading solution for a period of 5–10 min. The spreading solution is then exchanged with Millipore water by rinsing the IRE surface with water for several minutes to remove the excess vesicles while ensuring that the surface is always buried under the buffer. The bilayer coated samples are subsequently exposed to UV radiation using low pressure Hg pencil lamps (UVP, Inc) encapsulated in a quartz tube.

Imaging Ellipsometry: Label-free imaging of topographic contrasts in patterned sBLMs can be carried out using a commercial Imaging Null-Ellipsometer (Nanofilm Technologie, Gottingen, Germany). Details of the application of the technique are previously reported in literature. Briefly, the technique depends on the measurements of spatial variations in sample refractive index caused by the presence of topographic contrasts in the bilayer phase. The sBLM surface is illuminated with a p-polarized (parallel) incident beam (540 nm) at ~53°. The monolayer uncovered surface reflects little light and appears as a dark background in the microscope where as monolayer covered regions appear illuminated. As a result, a map of the bilayer distribution at the surface is acquired. The technique affords a resolution of ~2–4 μm. The images obtained are captured, e.g., into a personal computer using an image acquisition board (DT3155A, Data Translation, Calif.).

Epifluorescence Measurements: Typical epifluorescence emission images shown in the figures herein reveal high-contrast fluorescent patterns in UV illuminated sBLM samples. The sBLMs samples are typically formed by the rupture and fusion of POPC vesicles doped with 1 mol % fluorescent probe, namely Texas-Red-DHPE. In the figures herein, patterns comprising dark features, devoid of fluorescence emission separated by bright and homogeneous fluorescent background, correspond to the exposed and protected areas of the sample surface. Prior to patterning, the samples display uniformly red fluorescence comparable to the protected areas of the patterned samples, suggesting that patterning conditions did not noticeably alter the protected parts of the bilayers. A comparison of the bright-field image of a photomask and an epifluorescence image of the patterned bilayer shows that the sizes and shapes of the fluorescence-patterns are generally comparable replicas of mask-pattern. While sharp edges are evident, a rounding-off at the corners visible clearly in 100× magnifications-and is consistently observed. Occasionally, the features show enlargement or reduction which is thought to be due to off-parallel alignment between the mask and the sample surfaces. For a given lamp, the efficiency of the UV photochemistry in creating the relief pattern in bilayers, and the resulting definition of the patterns, depends upon, e.g., the distance between the lamp and the sample and that between the mask and the sample. Optimal results are typically obtained when the sample and mask are placed in a soft, direct contact with a distance of ~7 mm from the lamp. Examples presented in the figures herein illustrate the applicability of the approach for producing repeated patterns of arbitrary shapes, sizes, and densities at predetermined locations on a sample surface. With the present invention it is possible to produce feature sizes as small as 2 um, separated by 4 um distance, covering the entire sample surface (e.g., 22×22 mm 2 coverglass) which are limited by the size of the mask or the substrate itself. As explained elsewhere, however, limitations on feature size for bilayer patterning herein are optionally limited by a combination of the diffraction limit of the UV light, the attendant photochemical lipid oxidation, and any spreading of the residual bilayer at the edges. Repeating the measurements through use of various fluorophores (e.g., Texas-red, NBD, and BODIPY labeled DHPE lipids) and several phospholipids and their mixtures including DPPC, DMPC, DLPC, POPC, and egg-PC confirms that the pattern formation using UV illumination is independent of the nature of the fluorophores and the phase state of the lipids used. The features are stable with respect to their sizes and positions on the substrate surface while under aqueous buffer solutions for several days, indicating long-term stability: the bilayer does not reconfigure significantly over time and the position of the bilayer pattern on the substrate surface remains fixed. Reproducible patterns are derived when the exposure period is at least 15 minutes. in a typical illumination geometry.

Imaging Fluorescence Photobleach Recovery: Selected frames (t=0s, 3 min, 5 min, and 9 min) from a time-lapse sequence of images obtained during microscopy-based fluorescence photobleach recovery measurements are shown in the figures herein. Immediately following the photobleaching, a relatively sharp circular feature indicating bleached fluorophores is typically seen. As a function of time, the spot is observed to gradually recover, ultimately leading to uniform, lowered intensity across the image window. This behavior is qualitatively indicative of the translational mobility of the fluorophore, presumably by thermal diffusion, within a contiguous bilayer medium. The observed behavior is consistent with the presence of fluid bilayers in the protected regions. Such-fluidity of the bilayer is observed to persist uniformly in all areas of the residual bilayer including in the close-proximity of the etched regions. An example of typical fluorescence recovery profiles and the characteristic recovery time measured is also shown in the figures herein. Using the Soumpasis model (see above), this value is estimated at ~2.0 (+/−0.2) um2/sec for a POPC bilayer pattern by averaging D over four different positions on the sample surface. Before the sample is patterned, the average diffusional rate is comparable at 1.8 (+/−0.2) um2/second. This value is in good general correspondence with the values ranging from 0.5–5 um2/sec reported previously. See, e.g., Hovis, et al., Langmuir 17:3400–3405 (2001). Such confirms that the lipid bilayer in the UV-protected areas retain its fluidity.

Figure 25:
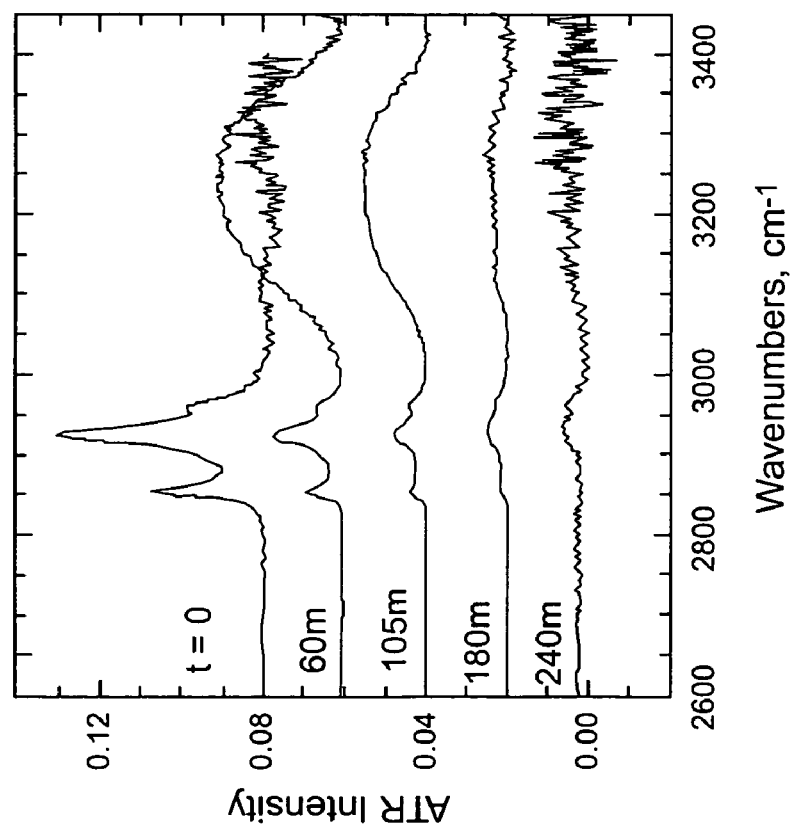
FIG. 25: Displays an in situ FTIR spectroscopy indicating that "holes" in patterned bilayers do not contain lipid structures.

Fourier-Transform Infrared Spectroscopy: In some embodiments of the invention, attenuated total reflection Fourier transform infrared (ATR-FTIR) spectra were obtained for sBLMs prepared on Si IRE element. The solid trace represents the spectrum obtained for the as-prepared samples and the dashed trace for the sample that had been exposed to UV radiation for an extended duration (~90 min). The spectrum for the un-illuminated bilayer (solid red trace) revealed three overlapping peaks with peak-maxima at 2852, 2923, and 2964 cm-1 in the 2800–3000 cm-1 region. These peaks can be straightforwardly assigned to the methylene and methyl C—H stretching mode absorptions. Precise position and width of these peaks can be used to assess the chain conformational structure. It should be noted that the observed peaks for the methylene C—H symmetric and antisym peaks are intermediate to the values for a fully ordered and maximally disordered acyl chains again confirming the fluid nature of the bilayers. In the spectrum for the UV illuminated samples, (gray dashed trace) no such absorptions are observed above the noise level indicating the absence of acyl chains. See FIG. 25 which shows that lipid molecules in UV illuminated regions dissociate leaving behind water-filled holes (i.e., without lipids).

Example Embodiment of use of Micro-Patterned Lipid Bilayers

As an illustration of various concepts herein, the following specific embodiment utilizes patterned lipid bilayers of the invention as screening/research tools. As stated above, surface patterning of nucleotides and proteins using standard photolithographic techniques in the solid state is leading to new high through-put approaches in a host of technologies, including sensor microarrays, massively-parallel genomics, drug screening, and proteomics research. Extending this strategy to cell membrane-mediated functions that depend on cooperative dynamics and wet environments has been a particular challenge. Development of a lipid based microarray platform, as detailed herein, enables parallel and high throughput chemical and biophysical analysis of cell membranes and membrane proteins (e.g., receptor-ligand binding, signal transduction, host-pathogen interactions, cell adhesion, and inflammation). The high-density arrays of spatially and geometrically defined voids within wet, fluid phospholipid bilayers on solid supports, which voids are optionally subsequently back-filled with desired lipid-mixtures that can remain phase-separated, provide functional membrane microenvironments within the phospholipid matrix. See, above.

The methods of the invention can optionally be used for the development of a platform technology for high throughput assessment of macromolecular assembly and cell adhesion. Thus, supported membrane microarrays displaying lipid-probes, molecules, and molecular patterns that provide the substrate for leukocyte binding and adhesion and signaling molecule assembly relevant to inflammatory effector function optionally can be created through use of the current invention. For example, specific applications of such can include the following. First, the nature and role of oxidative lipid modification during neutrophil-membrane encounter and microbicidal response can optionally be investigated. Specifically, microarrays displaying cis-parinaric acid, a naturally occurring fluorescent lipid-probe, are optionally created in systematically varied supported bilayer compositions. Upon exposure to activated neutrophils, the quantitative diminution and loss of parinaric acid fluorescence, upon myeloperoxidase-induced hypochlorous acid formation, can be used to develop detailed correlations between membrane composition, lipid degradation, and extent of HOCl penetration within the membrane medium. Second, systematic examination of macromolecular patterns of adhesion and G-protein signaling receptors, such as expressed in endothelium, within membrane raft-like microenvironments and their collective dynamics during neutrophil proinflammatory response can optionally be probed. The lipid microarray assays of the invention can provide the parallelization, throughput, and sensitivity for discovery of small molecules capable of disrupting exhuberant leukocyte inflammatory response.

The overall structure of the instant embodiment is that the development of lipid bilayer based functional microarray platforms can enable parallel and high throughput biochemical and biophysical analysis of a diverse set of cell functions including membrane receptor-ligand binding, cell adhesion, signal transduction, host-pathogen interactions, and oxidase activity. Specifically, a patterned bilayer construct that displays well-defined arrays of lipid-probes, molecules, and molecular patterns can be developed. A unique feature of patterned bilayers is their intrinsic fluidity that retains biomimetic properties including receptor diffusivity, cooperative in-plane and inter-membrane cooperativity, and flexibility for receptor-ligand assembly. These properties are minimum requirements for macromolecular assembly and formation of signaling complexes. that attend leukocyte inflammatory response. Moreover, the invention can be developed into a parallel geometry enabling high-throughput assays of cell adhesion and function. For example, three exemplary embodiments can include, e.g., the following.

First: development of a measurement platform. A high-density array of biomimetic membrane domains displaying recombinant cell adhesion molecules and acyl-chain linked function-reporting fluorophores can optionally be constructed and characterized through use of the current invention. The invention can provide a biomimetic substrate for leukocyte adhesion and allow optical readout of responses relevant to inflammatory effector function.

Second, patterned membrane domains can be used to study the spontaneous supramolecular self-assembly of receptor complexes and neutrophil adhesion in a high throughput manner. The concentrations and combinations of specific adhesion and G-protein coupled receptors in the membrane microarrays can be systemically varied to capture molecular mechanisms governing inflammatory processes at the leukocyte-endothelial interface.

Third, the functional analysis capacity of a construct through focus on the oxidants produced during the innate inflammatory/immune response can be demonstrated. Specifically, characterization in parallel assays of the lateral and transverse extent of membrane penetration by neutrophil-derived oxidants and their relation to the membrane compositions can optionally be performed through use of the current embodiment of the invention. Addressing this can optionally yield strategies for regulating pro- and anti-inflammatory redox signaling pathways.

Thus, in some aspects herein, the invention comprises, a modified lipid bilayer that has a primary lipid bilayer and one or more secondary lipid bilayer, and wherein one or more region of the secondary lipid bilayer is controllably localized within the primary lipid bilayer. Such modified lipid bilayers typically do not have any physical barrier that separates the primary lipid bilayer and the one or more secondary lipid bilayer. Also, the one or more secondary lipid bilayer comprises one or more molecule that adheres or recruits PMN to the secondary lipid bilayer. The one or more molecule in the secondary lipid bilayer regions can optionally comprise one or more of a selectin, an integrin, or a member of the Ig superfamily.

Other aspects of the current invention comprise methods for monitoring PMN adhesion or recruitment. Such methods comprise providing at least a first modified lipid bilayer as described above; providing one or more source of PMN; interacting the modified lipid bilayer with the PMN; and, measuring one or more resulting parameter to determine the interaction of the PMN and the modified lipid bilayer. Such modified lipid bilayers typically comprises a plurality of secondary lipid bilayer regions. Also, substantially each member of the plurality of secondary lipid bilayer regions typically comprises one or more molecule involved in PMN adhesion or recruitment. In many embodiments, the one or more molecule involved in PMN adhesion or recruitment comprises a plurality of molecules. In many other embodiments, substantially all members of the regions of secondary lipid bilayers comprise a different member of the plurality of molecules involved in recruitment or adhesion. Other embodiments comprise wherein the PMN and/or the secondary lipid bilayer are exposed to one or more compound (e.g., a chemokine or a cytokine or the like, etc.) prior to the interaction of the modified lipid bilayer and the PMN. In other embodiments, measurement of the interaction of the modified lipid bilayer and the PMN comprises quantification of fluorescence and/or quantification of a change in fluorescence of one or more molecule within one or more secondary lipid bilayer. Other embodiments include wherein such measuring comprises quantification of fluorescence and/or quantification of a change in fluorescence of one or more molecule on a side of the secondary lipid bilayer that is opposite a side that is exposed to the PMN.

The compelling aspect of this embodiment of the invention is the development and application of a novel lipid microarray for the parallel and high throughput analysis of leukocyte response as they engage mobile lipid tethered ligands within defined membrane patterned domains. This "lab on a chip" platform embodiment extends current technology by incorporating greater molecular specificity and mobility necessary to support native leukocyte receptor signaling complex assembly, while allowing rapid and parallel detection on a single cell basis over thousands of domains with sub-second dynamics of detection. Thus, this embodiment can be suitable for discovery of small molecules capable of disrupting exhuberant leukocyte inflammatory response over the course of adhesion, signaling, and oxidative response.

Figure 26:
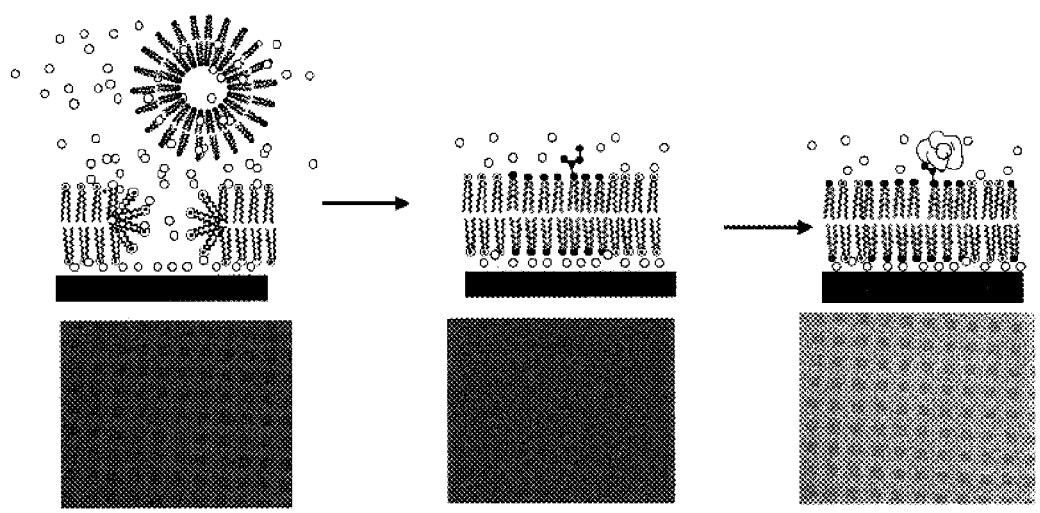
FIG. 26: Gives schematic diagrams and fluorescent images showing localization of cholera toxin within refunctionalized areas of a patterned bilayer due to binding with moieties localized in such areas.

As detailed previously, the current invention shows development of a wet lithographic tool for micro-patterning supported membranes. Such patterned holes in a lipid bilayer membrane are optionally refunctionalized with various components. FIG. 26 shows a cartoon depiction and fluorescence images showing incorporation of stable membrane domains incorporating protein binding lipid ligands (Gm1) and their binding to the protein partner (Cholera Toxin B subunits) at defined locations.

Macromolecular Assembly during Neutrophil Inflammatory Response

Figure 27:
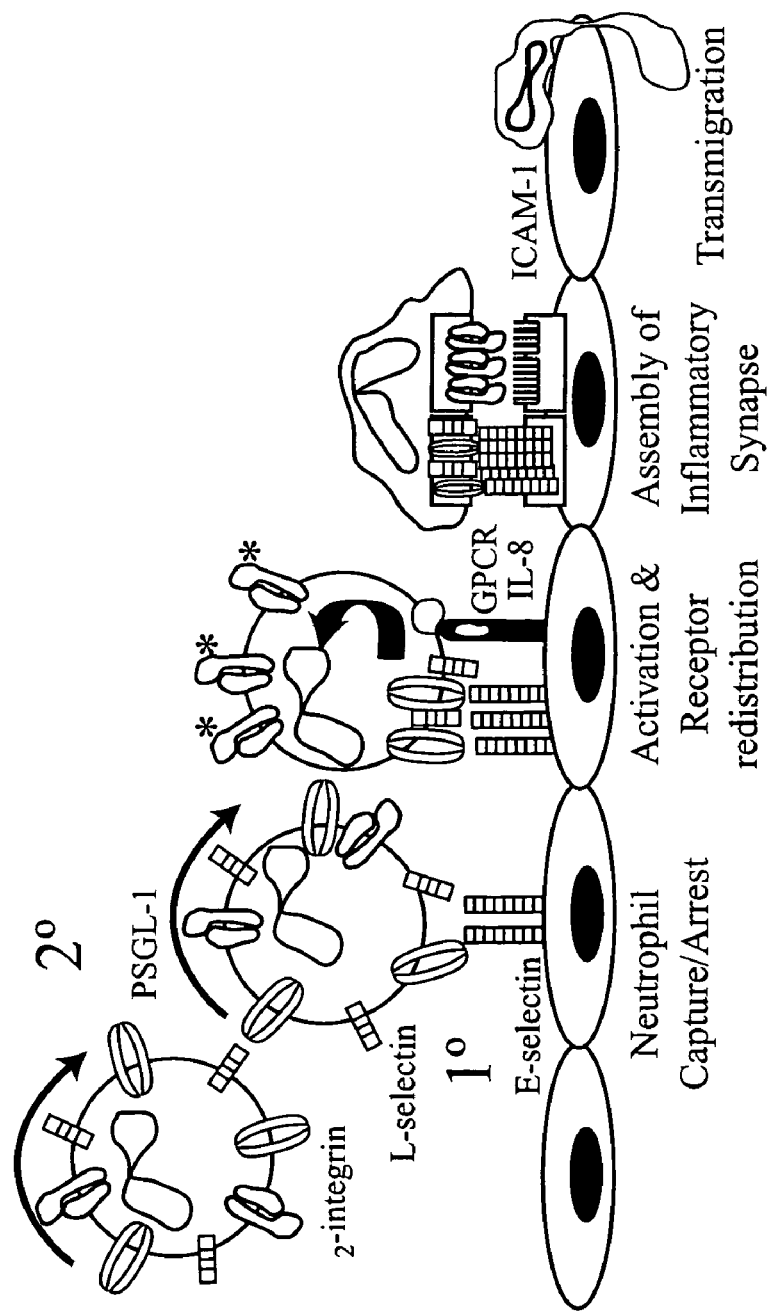
FIG. 27: Gives a schematic diagram of neutrophil capture/arrest and signaling.

Leukocyte recruitment is necessary for host defense against infection and for normal wound healing as exemplified in two classes of leukocyte adhesion receptor deficiency disease in which leukocytes lack expression of β2-integrins or fucosylated glycoprotein ligands recognized by selectins. These distinct genotypes share a common clinical profile of recurrent infections and impaired wound healing. From this it is clear that diminished recruitment of neutrophils (a.k.a. PMN or polymorphonuclear neutrophils, the most common leukocyte in blood) has a profound effect on the normal inflammatory response. Leukocyte recruitment in inflamed vessels is a multi-step recognition process that involves coordinate expression and ligation of at least three families of adhesion molecules: selectins, integrins, and the immunoglobulin gene super-family. See, e.g., FIG. 27. Pro-inflammatory cytokines, such as interleukin-8 (IL-8) or tumor necrosis factor (TNF-α), are released in response to a variety of noxious stimuli (e.g. burns, sepsis, cardio-bypass graft surgery, etc.). These stimulate the endothelium to upregulate E-selectin and P-selectin, which tether leukocytes and facilitate rolling and allow engagement of chemokines presented within the glycocalyx during immunosurveillance. Ligation of chemokines such as IL-8 to GPCRs induces PMN activation and assembly of adhesion complexes. See, e.g., Lum et al, *J. Biol. Chem.* 277:20660–20670 (2002). Integrins are the gatekeepers of leukocyte recruitment, as they require cell activation to adopt a ligand-binding conformation and supporting leukocyte arrest. FIG. 27 shows the multistep process of neutrophil capture and signaling of CD18-dependent arrest through assembly of the inflammatory synapse. Activated $\beta_2$-integrins (CD18) bind to ICAMs upregulated on inflamed endothelium and form adhesion complexes necessary for optimal degranulation and superoxide function.

Figure 28:
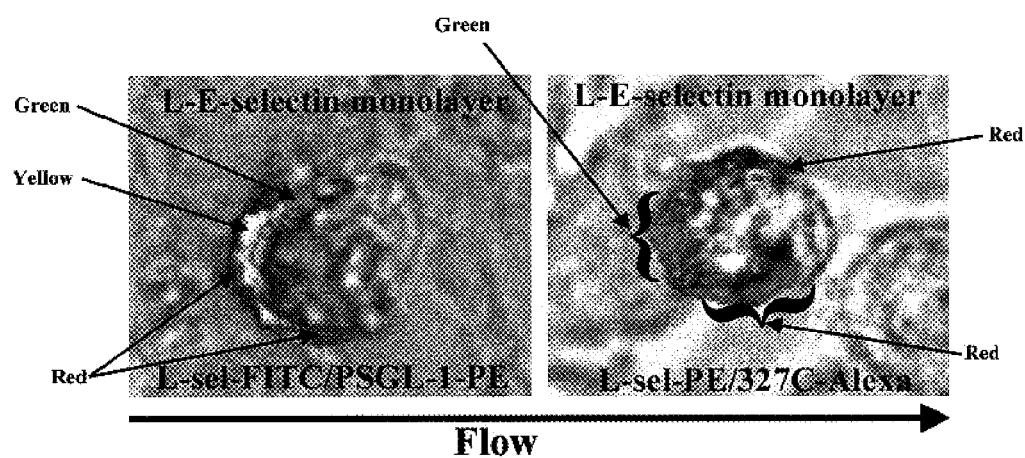
FIG. 28: Displays an image illustrating redistribution of L-selectin and PSGL-1 on PMNs fixed just after rolling in shear flow on a cell monolayer.

The primary mechanism of PMN activation on inflamed endothelium involves ligation of chemokines presented on the endothelium. The inventors have discovered a second mechanism that involves signal transduction through binding of selectins while PMNs tether in shear flow. They have recently reported that PMN rolling on a monolayer of cells co-expressing E-selectin and ICAM-1 in a parallel plate flow chamber led to PMN activation and cell arrest via activated CD18. Signaling of integrin function involved a conformational shift in CD18 and formation of clusters at the intercellular contact region. FIG. 28 illustrates redistribution of L-selectin and PSGL-1 on PMNs fixed just after rolling in shear flow on a cell monolayer expressing E-selectin in shear in the parallel plate flow chamber. FIG. 28 shows that PMN rolling on a monolayer expressing E-selectin results in co-localization of L-selectin, PSGL-1 and active CD18 (327C-Alexa) as PMNs tether in shear flow. Yellow fluorescence depicts regions on the trailing edge of a rolling PMN in which L-selectin and PSGL-1 are co-localized during ligation be E-selectin. Assembly of this complex required the presence of shear stress, but not chemotactic stimulation. However, these distinct signaling processes are synergistic since the combination potentiated the extent of clustering and PMN transmigration across human umbilical vein endothelial cells (HUVEC) stimulated with low dose IL-1. Macromolecular assembly and signaling involved MAP kinases as it was inhibited with small molecule antagonists of p38 and p42/44. In the context of PMN recruitment during inflammation, the current data supports a model by which PMN tethering on E-selectin in shear flow is synergistic with chemotactic stimulation in activation of CD18 within a region that is denoted as the inflammatory synapse. Current work helps shed light on the molecular mechanisms of this mechano-transduction and the significance to subsequent priming of PMN proinflammatory response as examined above.

Functional Analysis of the Neutrophil Inflammatory Response

Figure 29:
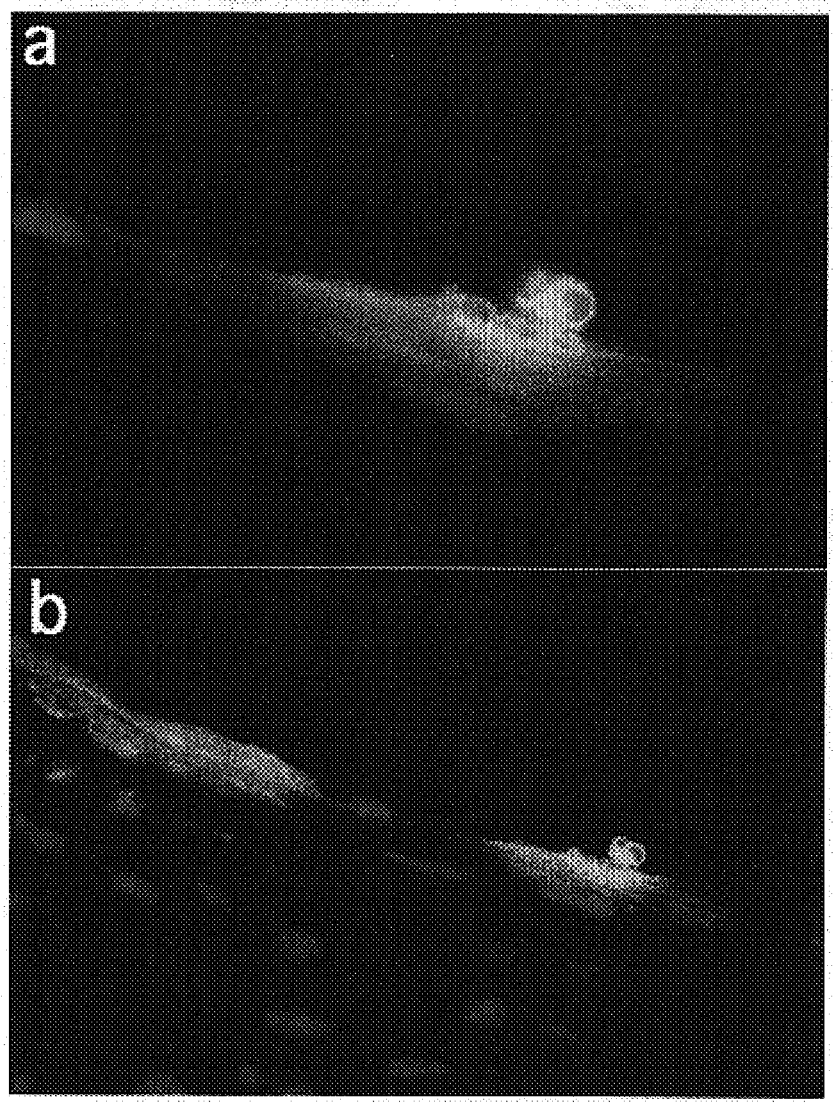
FIG. 29: Displays PMN during acute inflammatory processes binding to the surface of vascular endothelial cells

An important aspect of the function of neutrophils is the killing of invading microorganisms (i.e., host defense). This is achieved by activation of an NADPH-oxidase, which reduces diatomic oxygen to superoxide ($O_2^{\cdot-}$), which undergoes spontaneous or enzymatic dismutation to form hydrogen peroxide ($H_2O_2$). The $H_2O_2$ then reacts with the highly abundant hemoprotein, myeloperoxidase (MPO) to form hypochlorous acid (HOCl) via oxidation of chloride ($Cl^-$). In fact, MPO is secreted from activated PMN during acute inflammatory processes where it binds avidly to the surface of vascular endothelial cells. See, FIG. 29 and Eiserich et al., Science 296:2391–2394, 2002. The importance of the neutrophil NADPH oxidase in host defense is underscored by the fact that individuals with Chronic Granulomatous Disease (CGD), (deficiency in functional NADPH oxidase) suffer recurrent and severe infection. Nitric. oxide is another species that contributes to alterations in redox state within the contact region of phagocytes during host immune response. See, e.g., Eiserich, et al., Nature 391:393–397, (1998). FIG. 29 displays an activated neutrophil adherent to the endothelium of a rat blood vessel. The green stain shows myeloperoxidase immunoreactivity, not only in the neutrophil itself, but also in and around endothelial cells.

Thus, bacterial killing and inappropriate tissue injury results from generation of a potent cocktail of oxidants within neutrophil phagosomes and at the site of membrane contact. Additionally, oxidants produced by PMN are emerging as important signaling molecules; both pro- and anti-inflammatory. An emerging model for PMN activation and oxide production involves activation via 2 stimuli. The first is required to activate PMN $\beta_2$ integrins (i.e. GPCR stimuli such as IL-8, or selectin ligation), followed by a second $\beta_2$ integrin-mediated signal that is transduced following engagement to ICAM-1. The requirement for this dual signal for PMN generation of $O_2^-$ appears to serve as a key regulatory mechanism to limit $O_2^-$ production to a tissue environment where chemokine, or some other stimulus, is co-localized with endothelial cells bearing up-regulated ICAM-1. In conclusion, sequential exposure of PMNs to priming agents activates the microbicidal arsenal, and PMN-mediated endothelial damage as the result of two events, namely, endothelial activation and expression of chemokines and adhesion molecules and PMN ligation of CAM and oxidase assembly. This mechanism can optionally explain PMN mediated damage to many tissues that express ICAM-1 and chemokines and also in part why inhibitors of oxidase assembly or integrin activation are potent anti-inflammatory agents. In fact, synthetic enzymes of SOD or allosteric inhibitors of integrin-ligand binding, offer novel therapeutic approaches for the management of various inflammatory diseases where these radicals have been postulated to play a role. Assembly of signaling complexes leading to oxidation products can optionally be studied on neutrophils captured within patterned membrane domains of the invention.

Development and Characterization of Functionalized Membrane Microarrays for Cell Adhesion and Function Measurement platforms can optionally be constructed by adapting the UV membrane photolithography patterning herein or micro-contact printing methods (e.g., see above). The general process begins with the formation of supported, phospholipid bilayers e.g., POPC) displaying an array of lipid-free voids. The void-areas are subsequently backfilled or refunctionalized using selective-area rupture and spreading of secondary liposomes to create an array of functional micro-domains. The secondary liposomes can be synthetically prepared using standard vesicle preparation methods or can be derived from cell lysates. The former proteo-lipidic mixtures contain pre-defined concentrations of acyl-chain derivatized, recombinant Fc domains of relevant adhesion molecules including E-selectin, ICAM-1, and chemokines and other phospholipids, sphingolipids, and cholesterol. Stable isolation of these micro-domains from the background lipid bilayer can be achieved by controlling fluidity disparity between the background microphase and the domains. The micro-arrays can be designed and maintained wet and continuously submerged in a buffer medium.

Typical patterns can optionally comprise 100×100 μm² square topographies separated by 100 μm background primary bilayer areas, but smaller features and complex separation geometries can be easily implemented using appropriate lithographic masks. See above. Using multiple cycles of patterning and refunctionalization, domains of distinctly different chemical compositions can be engineered. Alternatively, micro-capillary injection approaches adapting commercial robotic spotters can also be used to prepare microarrays in single steps. Preliminary characterization is optionally through epifluorescence imaging. Any cross-contamination across microdomains can be tested using fluorescent antibodies specific to different receptors. Thus, such steps can provide a robust protocol for routine preparation of well-characterized membrane microarrays.

Macromolecular Assembly

Figure 30:
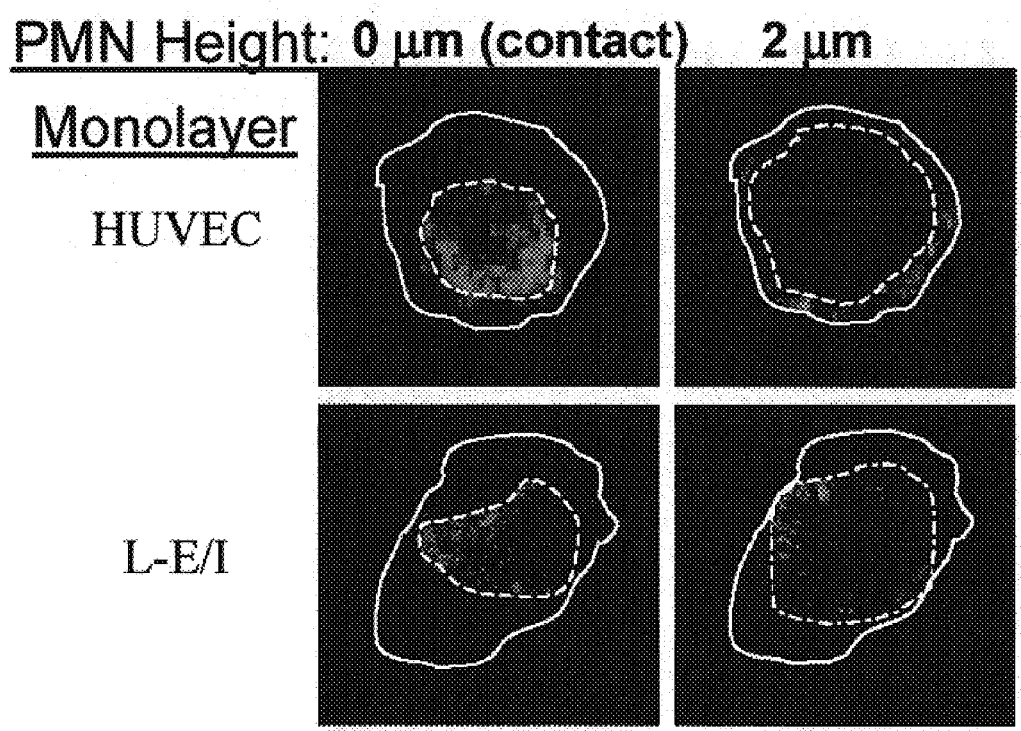
FIG. 30: Displays PMN cells sheared across IL-1 stimulated HUVEC.

Neutrophil CD11a and CD11b bind ICAM-1 at the first and third domains, respectively. For optimum stimulation and emigration at inflammatory sites, tethered neutrophils apparently must be activated locally rather than systemically in the circulation. Activation may occur as a result of several separate mechanisms including surface bound IL-8, or through tethering on E-selectin. FIG. 30 depicts an experiment in which PMNs were sheared across IL-1 stimulated HUVEC or L-E/I cells, then labeled for active CD18 with 327C-Alexa and imaged on a confocal microscope. FIG. 30 shows confocal imaging of active CD18 (327-C-Alexa) for plane of contact of PMN adherent to IL-1 stimulated HUVEC or L-cells expressing E-selectin and ICAM-1. It is clear that CD18 is redistributed upon contact with the monolayer substrate, as intense labeling is concentrated at the contact region. Thus, the current invention can be utilized to incorporate vascular ligands E-selectin and ICAM-1 and chemokine (i.e. IL-8) into the membrane domains to synthesize the biomimetic microarray. Two sources of these molecules can optionally be accessed: recombinant human IgG forms of E-selectin, ICAM-1, and IL-8 are commercially available (e.g., R&D Systems, Minn.). These can be covalently attached to lipids via a heterobifunctional cross-linker with an extended spacer arm that reacts with primary amines and sulfhydryl groups incorporated on the lipid (i.e. LC-SPDP Succinimidyl6-(3-[2-pyridyldithio]-propionamido hexanoate). Native proteins can also be incorporated by either fusing vesicles that are loaded with the respective receptors via a reconstitution procedure, or via a transfer directly from a micellar solution to the pre-formed lipid bilayer at the solid support. All the individual preparation steps and the various resulting patterned domains can be characterized by surface plasmon spectroscopy, contact angle measurements, IR spectroscopy, and fluorescence microscopy or the like.

Adhesion and Activation of PMNs to Membrane Domains

Some embodiments of the current invention can be used to determine activation of β2 integrin and subsequent adhesion to ICAM-1 as direct measures of PMN stimulation.

PMN isolated from freshly collected human blood samples remain unactivated and can be injected ($1\times10^5$/ml) into a parallel plate flow chamber assembled over a microarray of the invention. This will facilitate rapid distribution between 1–3 PMN onto each membrane domain at defined flow rate and shear stress. Thus, PMN activation can be measured by detection of 3 parameters. First, assembly of the inflammatory synapse in terms of co-clustering of L-selectin and PSGL-1 on PMN by domain resident E-selectin (i.e. FIG. 28) can be assessed. Second, activation of CD18 using 327C-Alexa fluorescence on clusters within the adhesive contact region of the bound and activated PMN (i.e. FIG. 30) can be measured. Finally, PMN capture on the E/I resident domains in terms of adhesion strength and stability can be assessed. Adhesion strength can be determined by increasing shear stress in discrete steps from that used to introduce PMN suspension up to high venous levels, 0.1–5.0 dyn/cm. Each domain can be analyzed for receptor fluorescence and PMN adhesion using an inverted Nikon fluorescence microscope and a motorized stage to address each domain. These studies can, thus, allow determination of PMN activation on E-selectin in the presence and absence of IL-8 and concentration dependence using the lab-on-a-chip format of the patterned lipid bilayers herein.

Detection of Oxidant Production in Activated PMN

It is now relatively well established that the differential priming effects of extracellular ligands leads to the activation of PMN which manifests as either intracellular or extracellular release of reactive oxygen species. Thus, in yet other embodiments of the current invention, the intracellular production of oxidants by activated PMNs ex-vivo adherent to the membrane domains of the microarray can be investigated through microarrays of the invention. Specifically, use of 2',7'-dichlorofluorescein diacetate (DCFH) as an intracellular probe can be used. See, e.g., Soh, et al., Cardiovasc. Res., 57(3):804–15 (2003). PMNs can be preincubated with the acetylated-DCFH, which is membrane permeable. Deacetylases within the cell can rapidly remove acetyl groups on the probe, thus, trapping the probe within the confines of intracellular space and allowing it to serve as a dosimeter of intracellular oxidant production. PMN can be preincubated with the probe that has been described, for detecting respiratory burst activity by flow cytometry in PMN suspension. Analyses can be carried out on a Nikon inverted microscope using a spinning disc filter system to excite and detect specific colors. Green fluorescence from DCFH can be detected in the green channel. Initial studies indicate that PMNs incubated with DCFH reports on peroxidase activity to react with $H_2O_2$. The high throughput assessment of small molecule inhibition of adhesive and catalytic component of PMN adhesion and oxidase assembly, as well as lipid-soluble antioxidants and scavengers of reactive oxygen species can also be evaluated.

Second, extracellular oxidant production can be assessed by exploiting the intramembrane oxidation of cis-paranaric acid incorporated to the membrane domains/areas. It is thought that PMN-derived oxidants play a redox-based signaling function in adjacent endothelial cells. Oxidants released within the PMN inflammatory synapse are thought to diffuse through the lipid membrane from the extracellular to intracellular space. The diffusivity of the oxidants across lipid bilayers is a function of the oxidants' half-life and presumably the nature of the lipid membrane. The composition of the membrane can be varied by modulating the degree of lipid unsaturation, proteins and controlled addition of cholesterol. By using these two complimentary approaches, the intracellular and extracellular oxidant production and diffusion across lipid bilayers can optionally be independently and/or simultaneously defined.

While the foregoing invention has been described in some detail for purposes of clarity and understanding, it will be clear to one skilled in the art from a reading of this disclosure that various changes in form and detail can be made without departing from the true scope of the invention. For example, all the techniques, apparatus, bilayer, kits, etc. described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method of constructing one or more modified lipid bilayers, the method comprising:
   i) providing at least a first primary lipid bilayer;
   ii) providing one or more sources of a UV light;
   iii) providing one or more patterned UV-opaque masks between the source of UV light and the primary lipid bilayer, which patterned UV mask comprises one or more UV-transparent areas at one or more specific locations in the UV mask;
   iv) creating in the primary lipid bilayer, one or more non-lipid areas beneath the one or more UV transparent areas of the UV-opaque mask, by exposing the primary lipid bilayer to UV light through the one or more patterned UV-opaque masks, thereby constructing one or more patterned lipid bilayers, which patterned lipid bilayer comprises the one or more non-lipid areas which spatially correspond to the one or more UV-transparent areas in the UV mask;
   v) providing at least a first secondary lipid bilayer; and,
   vi) contacting the one or more patterned lipid bilayers with the at least first secondary lipid bilayer, which at least first secondary lipid bilayer localizes within the one or more non-lipid areas in the patterned lipid bilayer.

2. The method of claim 1, wherein the UV mask comprises a plurality of UV masks and wherein the at least first secondary lipid bilayer comprises a plurality of secondary lipid bilayers.

3. The method of claim 2, wherein substantially each member of the plurality of UV masks comprises a different pattern, and wherein substantially each member of the plurality of secondary lipid bilayers comprises a different secondary lipid bilayer; further comprising:
   vii) sequentially repeating steps ii–vi for substantially all members of the plurality of UV masks and for substantially all members of the plurality of secondary lipid bilayers, thereby creating one or more modified primary lipid bilayers containing a plurality of different secondary lipid bilayers.

4. The method of claim 1 or 3, wherein the first primary lipid bilayer is selected from the group consisting of: a supported lipid bilayer, a tethered lipid bilayer, a polymer-cushioned lipid bilayer, a lipid bilayer comprising proteins in a proteo-lipidic mixture, and a hybrid lipid bilayer comprising an outer lipid layer and an inner self-assembled monolayer.

5. The method of claim 1 or 3, wherein the first primary lipid bilayer comprises a planar lipid bilayer.

6. The method of claim 1 or 3, wherein the first primary lipid bilayer comprises a non-planar lipid bilayer.

7. The method of claim 6, wherein the non-planar lipid bilayer comprises a spherical lipid bilayer, a cylindrical lipid bilayer, or a selected three-dimensional lipid bilayer.

8. The method of claim 1 or 3, wherein the first lipid bilayer comprises a bilayer supported on a planar substrate or a bilayer supported on a non-planar substrate.

9. The method of claim 1 or 3, wherein the first primary lipid bilayer comprises a first lipid layer and at least a second lipid layer.

10. The method of claim 9, wherein the first layer and the second layer comprise substantially similar lipid profiles, identical lipid profiles, or different lipid profiles.

11. The method of claim 9, wherein at least one of the first or second layers comprises a synthetic lipid layer.

12. The method of claim 1 or 3, wherein the one or more sources of UV light comprise a tungsten-halogen lamp, a xenon-arc lamp, a mercury lamp, or an excimer laser.

13. The method of claim 1 or 3, wherein the one or more sources of UV light emit UV light of a wavelength from between about 184 nm to about 257 nm.

14. The method of claim 1 or 3, wherein the patterned UV-opaque mask comprises a plurality of UV-transparent areas.

15. The method of claim 14, wherein the patterned UV-opaque mask comprises from about 144 to about 2200 UV-transparent areas per square centimeter, from about 200 to about 1500 UV-transparent areas per square centimeter, or from about 500 to about 1000 UV-transparent areas per square centimeter.

16. The method of claim 1 or 3, wherein the UV-transparent area comprises one or more length or width dimensions of from about 5 millimeters to about 0.1 micrometers or less.

17. The method of claim 16, wherein the one or more length or width dimensions comprise from about 2 millimeters to about 0.5 micrometers or less; from about 1 millimeter to about 1 micrometer or less; from about 500 micrometers to about 5 micrometers or less; from about 250 micrometers to about 10 micrometers or less; from about 100 micrometers to about 15 micrometers or less; or from about 75 micrometers to about 25 micrometers or less.

18. The method of claim 1 or 3, wherein the at least first secondary lipid bilayer comprises one or more of: a lipid raft, a lipid-coated bead, a liposome, a lipid vesicle, a polymerizable lipid, or a proteo-liposome.

19. The method of claim 1 or 3, wherein the first secondary lipid bilayer and the first primary lipid bilayer comprise substantially similar lipid bilayers, identical lipid bilayers, or different lipid bilayers.

20. The method of claim 19, wherein the at least first secondary lipid bilayer comprises a different lipid profile than the lipid profile of the first primary lipid bilayer, wherein the at least first secondary lipid bilayer comprises a different amount of proteins than the first primary lipid bilayer, wherein the at least first secondary lipid bilayer comprises a different type of proteins than the first primary lipid bilayer, wherein the at least first secondary lipid bilayer comprises a different lipid diffusion coefficient than the first primary lipid bilayer, or wherein the at least first secondary lipid bilayer comprises a different amount of cholesterol than the first primary lipid bilayer.

21. The method of claim 1 or 3, wherein the one or more non-lipid areas are contiguous non-lipid areas.

22. A method of constructing one or more chimeric lipid bilayers, the method comprising:
 i) providing at least a first lipid bilayer;
 ii) providing one or more sources of UV light;
 iii) providing one or more patterned UV-opaque masks between the source of UV light and the at least first lipid bilayer, which patterned UV mask comprises one or more UV-transparent areas at one or more specific locations in the UV mask;
 iv) creating in the primary lipid bilayer, one or more non-lipid areas beneath the one or more UV transparent areas of the UV-opaque mask, by exposing the primary lipid bilayer to UV light through the one or more patterned UV-opaque masks, thereby constructing one or more patterned lipid bilayers, which patterned lipid bilayer comprises the one or more non-lipid areas which spatially correspond to the one or more UV-transparent areas in the UV mask;
 v) providing at least a first secondary material; and,
 vi) contacting the one or more patterned lipid bilayers with the at least first secondary material, which at least first secondary material localizes within the one or more non-lipid areas in the patterned lipid bilayer.

23. The method of claim 22, wherein the UV mask comprises a plurality of UV masks and wherein the at least first secondary material comprises a plurality of secondary materials.

24. The method of claim 23, wherein substantially each member of the plurality of UV masks comprises a different pattern, and wherein substantially each member of the plurality of secondary materials comprises a different secondary material; further comprising:
 vii) suquentially repeating steps ii–vi for substantially all members of the plurality of UV masks and for substantially all members of the plurality of secondary materials, thereby creating one or more chimeric lipid bilayers containing a plurality of different secondary materials.

25. The method of claim 22 or 24, wherein the first primary lipid bilayer is selected from the group consisting of: a supported lipid bilayer, a tethered lipid bilayer, a polymer-cushioned lipid bilayer, a lipid bilayer comprising proteins in a proteo-lipidic mixture, and a hybrid lipid bilayer comprising an outer lipid layer and an inner self-assembled monolayer.

26. The method of claim 22 or 24, wherein the first primary lipid bilayer comprises a planar lipid bilayer.

27. The method of claim 22 or 24, wherein the first primary lipid bilayer comprises a non-planar lipid bilayer.

28. The method of claim 27, wherein the non-planar lipid bilayer comprises a spherical lipid bilayer, a cylindrical lipid bilayer, or a selected three-dimensional lipid bilayer.

29. The method of claim 22 or 24, wherein the first lipid bilayer comprises a bilayer supported on a planar substrate or a bilayer supported on a non-planar substrate.

30. The method of claim 22 or 24, wherein the first primary lipid bilayer comprises a first lipid layer and at least a second lipid layer.

31. The method of claim 30, wherein the first layer and the second layer comprise substantially similar lipid profiles, identical lipid profiles, or different lipid profiles.

32. The method of claim 30, wherein at least one of the first layer or the second layer comprises a synthetic lipid layer.

33. The method of claim 22 or 24, wherein the one or more sources of UV light comprise a tungsten-halogen lamp, a xenon-arc lamp, a mercury lamp, or an excimer laser.

34. The method of claim 22 or 24, wherein the one or more sources of UV light emit UV light of a wavelength from between about 184 nm to about 257 nm.

35. The method of claim 22 or 24, wherein the patterned UV-opaque mask comprises a plurality of UV-transparent areas.

36. The method of claim 35, wherein the patterned UV-opaque mask comprises from about 144 to about 2200 UV-transparent areas per square centimeter, from about 200 to about 1500 UV-transparent areas per square centimeter, or from about 500 to about 1000 UV-transparent areas per square centimeter.

37. The method of claim 22 or 24, wherein the UV-transparent area comprises one or more length or width dimensions of from about 5 millimeters to about 0.1 micrometers or less.

38. The method of claim 37, wherein the one or more length or width dimensions comprise from about 2 millimeters to about 0.5 micrometers or less; from about 1 millimeter to about 1 micrometer or less; from about 500 micrometers to about 5 micrometers or less; from about 250 micrometers to about 10 micrometers or less; from about 100 micrometers to about 15 micrometers or less; or from about 75 micrometers to about 25 micrometers or less.

39. The method of claim 22 or 24, wherein the one or more non-lipid areas are contiguous non-lipid areas.

40. The method of claim 22 or 24, wherein the secondary material comprises one or more of: a cell, a protein, a glass bead, a latex bead, a bilayer coated bead, a membrane compatible amphiphilic polymer, a nanocrystal, a colloid, a quantum-dot material, a metal, a metal bead, or a polymerizable precursor molecule.

41. The method of claim 22 or 24, wherein the secondary material undergoes a spatially confined chemical reaction.

42. The method of claim 41, wherein the reaction comprises one or more of an electrochemical metal reduction, a polymerization, a protein-ligand reaction, or a cell-capture.

\* \* \* \* \*